US011260117B2

(12) United States Patent
Masternak et al.

(10) Patent No.: US 11,260,117 B2
(45) Date of Patent: Mar. 1, 2022

(54) ANTI-CD47 X ANTI-MESOTHELIN ANTIBODIES AND METHODS OF USE THEREOF

(71) Applicant: NovImmune SA, Geneva (CH)

(72) Inventors: Krzysztof Masternak, Mollens (CH); Nicolas Fischer, Geneva (CH)

(73) Assignee: NovImmune SA, Geneva (CH)

( * ) Notice: Subject to any disclaimer, the term of this patent is extended or adjusted under 35 U.S.C. 154(b) by 536 days.

(21) Appl. No.: 15/991,774

(22) Filed: May 29, 2018

(65) Prior Publication Data

US 2018/0339031 A1  Nov. 29, 2018

Related U.S. Application Data

(60) Provisional application No. 62/550,387, filed on Aug. 25, 2017, provisional application No. 62/511,669, filed on May 26, 2017.

(51) Int. Cl.
| | |
|---|---|
| *C07K 16/00* | (2006.01) |
| *A61K 39/00* | (2006.01) |
| *C07K 16/28* | (2006.01) |
| *C07K 16/30* | (2006.01) |
| *A61K 39/395* | (2006.01) |
| *C07K 16/46* | (2006.01) |
| *A61P 35/00* | (2006.01) |

(52) U.S. Cl.
CPC ...... *A61K 39/001168* (2018.08); *A61K 39/00* (2013.01); *A61K 39/001129* (2018.08); *A61K 39/39558* (2013.01); *A61P 35/00* (2018.01); *C07K 16/00* (2013.01); *C07K 16/2896* (2013.01); *C07K 16/30* (2013.01); *C07K 16/303* (2013.01); *C07K 16/468* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,676,980 A | 6/1987 | Segal et al. |
| 4,816,567 A | 3/1989 | Cabilly et al. |
| 5,013,556 A | 5/1991 | Woodle et al. |
| 5,030,719 A | 7/1991 | Umemoto et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,916,771 A | 6/1999 | Hori et al. |
| 5,939,598 A | 8/1999 | Kucherlapati et al. |
| 6,075,181 A | 6/2000 | Kucherlapati et al. |
| 6,150,584 A | 11/2000 | Kucherlapati et al. |
| 6,528,624 B1 | 3/2003 | Idusogie et al. |
| 2009/0191199 A1 | 7/2009 | Kanda et al. |
| 2012/0184716 A1 | 7/2012 | Fischer et al. |

FOREIGN PATENT DOCUMENTS

| | | | |
|---|---|---|---|
| WO | WO 91/00360 A1 | | 1/1991 |
| WO | WO 92/20373 A1 | | 11/1992 |
| WO | WO 93/08829 A1 | | 5/1993 |
| WO | WO 94/02602 A1 | | 2/1994 |
| WO | WO 94/11026 A2 | | 5/1994 |
| WO | WO 95/22618 A1 | | 8/1995 |
| WO | WO 96/27011 A1 | | 9/1996 |
| WO | WO 96/33735 A1 | | 10/1996 |
| WO | WO 96/34096 A1 | | 10/1996 |
| WO | WO 99/53049 A1 | | 10/1999 |
| WO | WO 2010/135558 A1 | | 11/2010 |
| WO | WO 2011/084255 A2 | | 7/2011 |
| WO | WO 2012/023053 A2 | | 2/2012 |
| WO | WO 2013/088259 A2 | | 6/2013 |
| WO | WO/2014/087248 | * | 6/2014 |
| WO | WO 2014/087248 A2 | | 6/2014 |

OTHER PUBLICATIONS

Almagro & Fransson, Frontiers in Bioscience 2008; 13:1619-33 (Year: 2008).*
Padlan (Advances in Protein Chemistry, 1996, 49:57-133) (Year: 1996).*
Berglund et al, Protein Science, 2008, 17:606-613 (Year: 2008).*
Corada (Blood, 2001; 97:1679-84) (Year: 2001).*
Kulkarni-Kale et al. Nucleic Acid Research, 2005, 33:W168-W171 (Year: 2006).*
Bobo, R.H. et al. (1994) "Convection-enhanced delivery of macromolecules in the brain" *Proc Natl Acad Sci USA*, 91:2076-2080.
Brodeur, B.R. et al., "Mouse-Human Myeloma Partners for the Production of Heterohybridomas" in *Monoclonal Antibody Production Techniques and Applications*. L.D. Schook (Ed.); New York: Marcel Dekker, Inc., 1987; pp. 51-63.
Brown, E.J. and W.A. Frazier (Mar. 2001) "Integrin-associated protein (CD47) and its ligands" *Trends Cell Biol*, 11(3): 130-135.
Bruce, M.P. et al. (2002) "Dialysis-bases bioreactor systems for the production of monoclonal antibodies—alternatives to ascites production in mice" *Journal of Immunological Methods*, 264:59-68.
Caron, P.C. et al. (Oct. 1992) "Engineered Humanized Dimeric Forms of IgG are More Effective Antibodies" *J Exp Med*, 176:1191-1195.
Chao, M.P. et al. (Feb. 15, 2011) "Therapeutic antibody targeting of CD47 eliminates human acute lymphoblastic leukemia" *Cancer Res*, 71(4): 1374-1384.
Chappell, S.A. et al. (Feb. 15, 2000) "A 9-nt segment of a cellular mRNA can function as an internal ribosome entry site (IRES) and when present in linked multiple copies greatly enhances IRES activity" *Proc Natl Acad Sci USA*, 97:1536-1541.

(Continued)

*Primary Examiner* — Meera Natarajan
(74) *Attorney, Agent, or Firm* — Cooley LLP; Cynthia A. Kozakiewicz; Ivor R. Elrifi

(57) ABSTRACT

The invention also relates to novel bispecific antibodies carrying a different specificity for each binding site of the immunoglobulin molecule, where one of the binding sites is specific for CD47 and the second is specific for mesothelin (MSLN).

18 Claims, 13 Drawing Sheets

Specification includes a Sequence Listing.

(56) References Cited

OTHER PUBLICATIONS

Cole, S.P.C. et al. (1985) "The EBV-Hybridoma Technique and Its Application to Human Lung Cancer" in *Monoclonal Antibodies and Cancer Therapy. Proceedings of the Roche-UCLA Symposium*, Park City Utah, Jan. 26-Feb. 2, 1985. R.A. Reisfeld and S. Sell.
Cote, R. et al. (Apr. 1983) "Generation of human monoclonal antibodies reactive with cellular antigens" *Proc Natl Acad Sci USA*, 80:2026-2030.
Davidson, B.L. et al. (Mar. 1993) "A model system for in vivo gene transfer into the central nervous system using an adenoviral vector" *Nat Genet*, 3:219-223.
Davis, J.H. et al. (2010) "SEEDbodies: fusion proteins based on strand-exchange engineered domain (SEED) $C_H3$ heterodimers in an Fc analogue platform for asymmetric binders or immunofusions and bispecific antibodies" *Protein Engineering, Design & Selection*.
Dheilly, E. et al. (Feb. 2017) "Selective Blockade of the Ubiquitous Checkpoint Receptor CD47 is Enabled by Dual-Targeting Bispecific Antibodies" *Mol Ther*, 25(2):523-533.
Epstein, D.A. et al. (Jun. 1985) "Biological activity of liposome-encapsulated murine interferon γ is mediated by a cell membrane receptor" *Proc Natl Acad Sci USA*, 82:3688-3692.
Fischer, N. et al. (Feb. 12, 2015) "Exploiting light chains for the scalable generation and platform purification of native human bispecific IgG" *Nature Communications*, 6:6113; doi: 10.1038/ncomms7113, 12 pages.
Fishwild, D.M. et al. (Jul. 1996) "High-avidity IgGK monoclonal antibodies from a novel strain of minilocus transgenic mice" *Nature Biotechnology*, 14:845-851.
Geller, A.I. et al. (1990) "Infection of cultured central nervous system neurons with a defective herpes simplex virus 1 vector results in stable expression of *Escherichia coli* β-galactosidase" *Proc Natl Acad Sci USA*, 87:1149-1153.
Geller, A.I. et al. (1993) "Long-term increases in neurotransmitter release from neuronal cells expressing a constitutively active adenylate cyclase from a herpes simplex virus type 1 vector" *Proc Natl Acad Sci USA*, 90:7603-7607.
Geller, A.I. et al. (1995) "An HSV-1 Vector Expressing Tyrosine Hydroxylase Causes Production and Release of L-DOPA from Cultured Rat Striatal Cells" *JNeurochem*, 64:487-496.
Goding, J.W. (1986) "Production of Monoclonal Antibodies", in *Monoclonal Antibodies: Principles and Application of Monoclonal Antibodies in Cell Biology, Biochemistry and Immunology*. 2nd Ed., Academic Press; pp. 59-103.
Gramer, M.J. et al. (2013) "Production of stable bispecific IgG1 by controlled Fab-arm exchange. Scalability from bench to large-scale manufacturing by application of standard approaches" *MAbs*, 5(6):962-973.
Gruber, M. et al. (1994) "Efficient Tumor Cell Lysis Mediated by a Bispecific Single Chain Antibody Expressed in *Escherichia coli*" *J Immunol*, 152:5368-5374.
Gunadekaran, K. et al. (Jun. 18, 2010) "Enhancing Antibody Fc Heterodimer Formation through Electrostatic Steering Effects" *J Biol Chem*, 285(25):19637-19646.
Hellen, C.U.T. and P. Sarnow (2001) "Internal ribosome entry sites in eukaryotic mRNA molecules" *Genes Dev*, 15:1593-1612.
Holliger, P. et al. (Jul. 1993) "'Diabodies': Small bivalent and bispecific antibody fragments" *Proc Natl Acad Sci USA*, 90:6444-6448.
Hoogenbom, H.R. and G. Winter, (1992) "By-passing Immunisation Human Antibodies from Synthetic Repertoires of Germline $V_H$ Gene Segments Rearranged in Vitro" *J Mol Biol*, 227:381-388.
Hwang, K.J. et al. (Jul. 1980) "Hepatic uptake and degradation of unilamellar sphingomyelin/cholesterol liposomes: A kinetic study" *Proc Natl Acad Sci USA*, 77:4030-4034.
Jaiswal, S. et al. (Jul. 2009) "CD47 is up-regulated on circulating hematopoietic stem cells and leukemia cells to avoid phagocytosis" *Cell*, 138(2):271-285.
Jansen, F.K. et al. (1982) "Immunotoxins: Hybrid Molecules Combining High Specificity and Potent Cytotoxicity" *Immunological Reviews*, 62:185-216.
Jones, P.T. et al. (May 1986) "Replacing the complementarity-determining regions in a human antibody with those from a mouse" *Nature*, 321:522-525.
Kaplitt, M.G. et al. (1994) "Long-term gene expression and phenotypic correction using adeno-associated virus vectors in the mammalian brain" *Nat Genet*, 8:148-154.
Killen, J.A. and J.M. Lindstrom (Nov. 1984) "Specific killing of lymphocytes that cause experimental autoimmune myasthenia gravis by ricin toxin-acetylcholine receptor conjugates" *J Immunol*, 133(5):2549-2553.
Klein, C. et al. (2012) "Progress in overcoming the chain association issue in bispecific heterodimeric IgG antibodies" *mAbs*, 4(6):653-663.
Köhler, G. and C. Milstein (1975) "Continuous cultures of fused cells secreting antibody of predefined specificity" *Nature*, 256:495-497.
Kontermann, R.E. et al. (Jul. 1997) "Complement recruitment using bispecific diabodies" *Nat Biotechnol*, 15(7):629-631.
Kosco-Vilbois, M. (Mar. 2017) "Targeting CD47 to involve macrophages and dentritic cells in a holistic anti-tumor immune response" Novimmune SA: Presented at ICI Boston [online]. Retrieved from the Internet: http://immune-checkpoint.com/wp-content/upload.
Kostelny, S.A. et al. (1992) "Formation of a Bispecific Antibody by the Use of Leucine Zippers" *J Immunol*, 148:1547-1553.
Kozbor, D. and J.C. Roder et al. (1983) "The production of monoclonal antibodies from human lymphocytes" *Immunol Today*, 4:72-79.
Kozbor, D. et al. (Dec. 1984) "A human hybrid myeloma for production of human monoclonal antibodies" *J Immunol*, 133:3001-3005.
Le Gal La Salle, G. et al. (1993) "An Adenovirus Vector for Gene Transfer into Neurons and Glia in the Brain" *Science*, 259:988-990.
Lonberg et al. (1994) "Antigen-specific human antibodies from mice comprising four distinct genetic modifications" *Nature* 368 856-859.
Lonberg, N. and D. Huszar (1995) "Human Antibodies from Transgenic Mice" *Intern Rev Immunol*, 13:65-93.
Majeti, R. al. (Jul. 23, 2009) "CD47 is an adverse prognostic factor and therapeutic antibody target on human acute myeloid leukemia stem cells" *Cell*, 138(2):286-299. NIH Public Access Author Manuscript; available in PMC Jul. 23, 2010, 24 pages.
Marks, J.D. et al. (1991) "By-passing Immunization. Human Antibodies from V-gene Libraries Displayed on Phage" *J Mol Biol*, 222:581-597.
Marks, J.D. et al. (Jul. 1992) "By-passing Immunization: Building High Affinity Human Antibodies by Chain Shuffling" *Bio/Technology*, 10:779-783.
Olsson, Mattias (2008) *Role of the CD47/SIRPα-interaction in regulation of macrophage phagocytosis*. Thesis: Department of Integrative Medical Biology, Section for Histology and Cell Biology, Umeå University, Umeå, Sweden, 59 pages.
Mcdonald, K.A. et al. (2005) "Production of human alpha-1-antitrypsin from transgenic rice cell culture in a membrane bioreactor" *Biotechnol Prog*, 21:728-734.
Milstein, C. and A.C. Cuello (1983) "Hybrid hybridomas and their use in immunohistochemistry" *Nature*, 305:537-539.
Moore, P.A. et al. (2011) "Application of dual affinity retargeting molecules to achieve optimal redirected T-cell killing of B-cell lymphoma" *Blood*, 117(17):4542-4551.
Morrison, S.L. (Apr. 1994) "Success in specification" *Nature*, 368:812-813.
Morrison, P.F. et al. (1994) "High-flow microinfusion: tissue penetration and pharmacodynamics" *Am J Physiol*, 266:R292-R305.
Munson, P. J. and D. Rodbard (1980) "LIGAND: A Versatile Computerized Approach for Characterization of Ligand-Binding Systems" *Analytical Biochemistry*, 107:220-239.
Neuberger, M. (1996) "Generating high-avidity human Mabs in mice" *Nature Biotechnology*, 14:826.

(56) References Cited

OTHER PUBLICATIONS

Oldenborg. P.-A. et al. (Apr. 2, 2001) "CD47-Signal Regulatory Protein α (SIRPα) Regulates Fcγ and Complement Receptor-mediated Phagocytosis" *J Exp Med*, 193(7):855-862.
Oldenborg, P.-A. et al. (Jun. 16, 2000) "Role of CD47 as a Marker of Self on Red Blood Cells" *Science*, 288(5473):2051-2054.
Oldenborg, P.-A. (Jul. 2004) "Role of CD47 in erythroid cells and in autoimmunity" *Leuk Lymphoma*, 45(7):1319-1327.
Oldenborg, P-A. (2013) "CD47: A Cell Surface Glycoprotein Which Regulates Multiple Functions of Hematopoietic Cells in Health and Disease" *ISRN Hematol*, vol. 2013, Article 614619, 19 pages.
Portner, L. et al. (2012) "T and NK cells of B cell NHL patients exert cytotoxicity against lymphoma cells following binding of bispecific tetravalent antibody CD19 x CD3 or CD19 x CD16" *Cancer Immunol Immunother*, 61(10):1869-1875.
Presta, L. (1992) "Antibody engineering" *Current Opinion in Structural Biology*, 2:593-596.
Pubchem Substance Record SID 124490507 (Aug. 2, 2011) "931402-35-6" National Center for Biotechnology Information (NCBI) [online]. Retrieved from: https://pubchem.ncbi.nlm.nih.gov/substance/124490507; retrieved on Aug. 20, 2018, 5 pages.
Ramakrishnan, S. et al. (1984) "Comparison of the Selective Cytotoxic Effects of Immunotoxins Containing Ricin A Chain or Pokeweed Antiviral Protein and Anti-Thy 1.1 Monoclonal Antibodies", *Cancer Res*, 44:201-208.
Ridgway, J.B.B. et al. (1996) "'Knobs-into-holes' engineering of antibody $C_H3$ domains for heavy chain heterodimerization" *Protein Eng*, 7:617-621 (1996).
Riechmann, L. et al. (1988) "Reshaping human antibodies for therapy" *Nature*, 332:323-327.
Shopes, B. (May 1992) "A genetically engineered human IgG mutant with enhanced cytolytic activity" *J Immunol*, 148:2918-2922.
Sick E. et al. (2012) "CD47 update: a multifaceted actor in the tumor microenvironment of potential therapeutic interest" *Br J Pharmacol*, 67(7):1415-1430.
Soto-Pantoja, D.R. et al. (Jan. 2013) "Therapeutic opportunities for targeting the ubiquitous cell surface receptor CD47" *Expert Opin Ther Targets*, 17(1):89-103. NIH Public Access Author Manuscript, available in PMC Jan. 1, 2014, 23 pages.
Stevenson, G.T. et al. (1989) "A chimeric antibody with dual Fc regions (bisFabFc) prepared by manipulations at the IgG hinge" *Anti-Cancer Drug Design*, 3:219-230.
Strohl, W. (2009) "Optimization of Fc-mediated effector functions of monoclonal antibodies" *Curr Opin Biotechnol*, 20:685-691.
Suresh, M.R. et al. (1986) "Bispecific Monoclonal Antibodies from Hybrid Hybridomas" *Methods in Enzymology*, 121:210-228.
Traunecker, A. et al. (1991) "Bispecific single chain molecules (Janusins) target cytotoxic lymphocytes on HIV infected cells" *EMBO Journal*, 10:3655-3659.
Tutt, A. et al. (Jul. 1991) "Trispecific F(ab')$_3$ Derivatives That Use Cooperative Signaling via the TCR/CD3 Complex and CD2 to Activate and Redirect Resting Cytotoxic T Cells" *Journal of Immunology*, 147:60-69.
Verhoeyen, M. et al. (1988) "Reshaping Human Antibodies: Grafting an Antilysozyme Activity" *Science*, 239:1534-1536.
Vitetta, E.S. et al. (1987) "Redesigning Nature's Poisons to Create Anti-Tumor Reagents" *Science*, 238:1098-1104.
Von Kreudenstein, T. et al. (2013) "Improving biophysical properties of a bispecific antibody scaffold to aid developability" *mAbs*, 5(5):646-654.
Weiskopf, K. et al. (Jul. 5, 2013) "Engineered SIRPα Variants as Immunotherapeutic Adjuvants to Anti-cancer Antibodies" *Science*, 341(6141):88-91.
Wilkinson, D. (Apr. 17, 2000) "Ultimate Abs" *The Scientist*, 14(8):25-28.
Willingham, S.B. et al. (Apr. 24, 2012) "The CD47-signal regulatory protein alpha (SIRPα) interaction is a therapeutic target for human solid tumors" *Proc Natl Acad Sci USA*, 109(17):6662-6667.
Wolf, E. et al. (2005) "BiTEs: bispecific antibody constructs with unique anti-tumor activity" *Drug Discov Today*, 10(18):1237-1244.
Yang, Y. et al. (Apr. 1995) "Cellular and Humoral Immune Responses to Viral Antigens Create Barriers to Lung-Directed Gene Therapy with Recombinant Adenoviruses" *J Virol*, 69(4):2004-2015.

\* cited by examiner

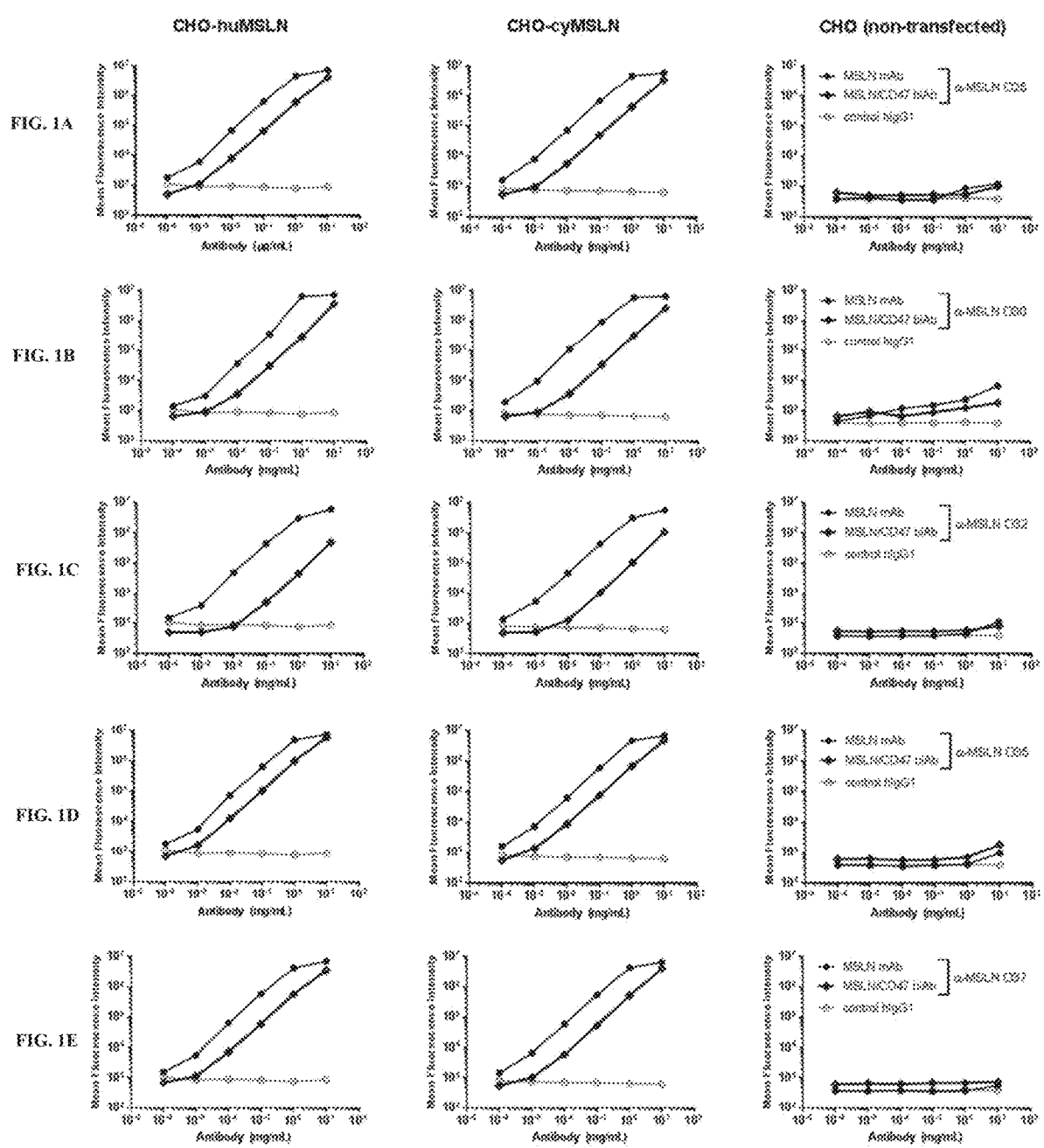

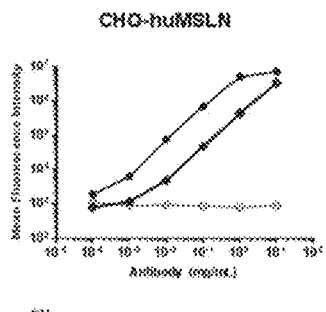
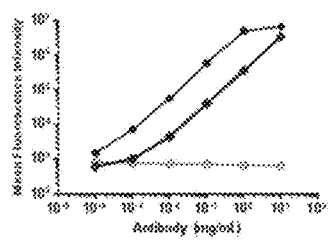
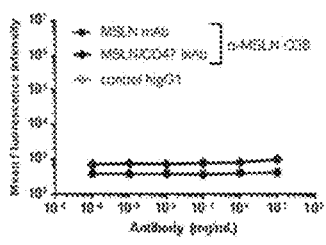
FIG. 1F
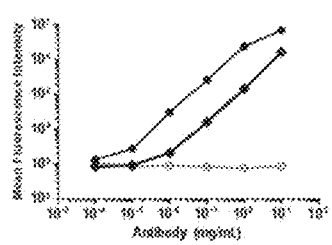
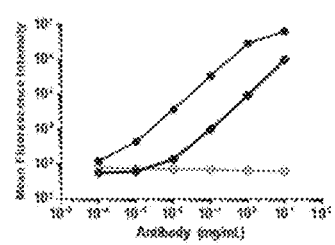
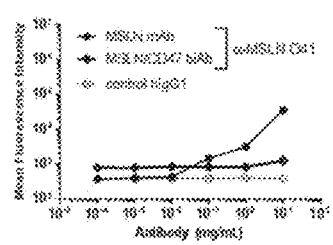
FIG. 1G

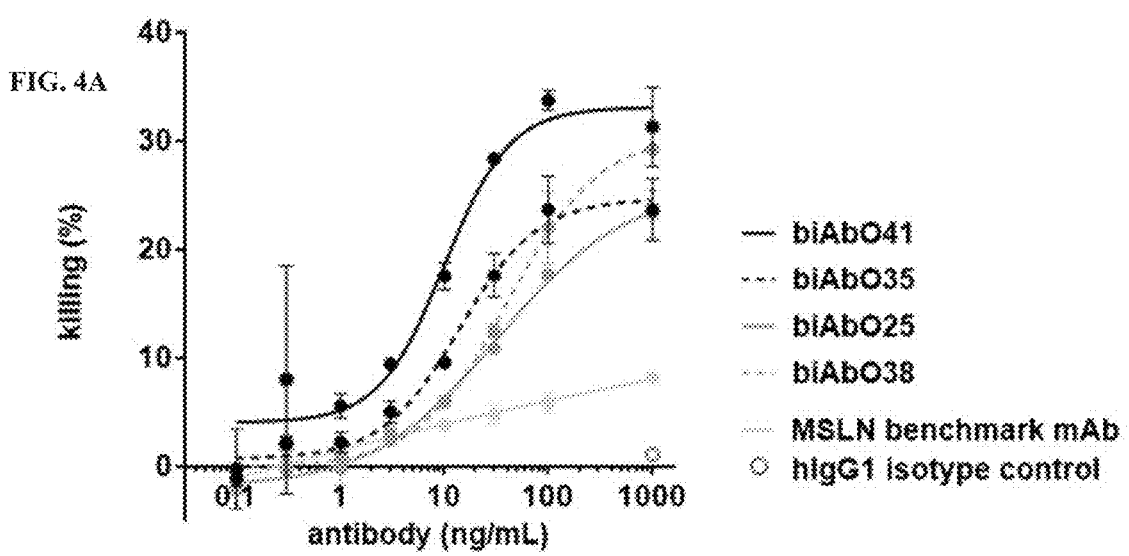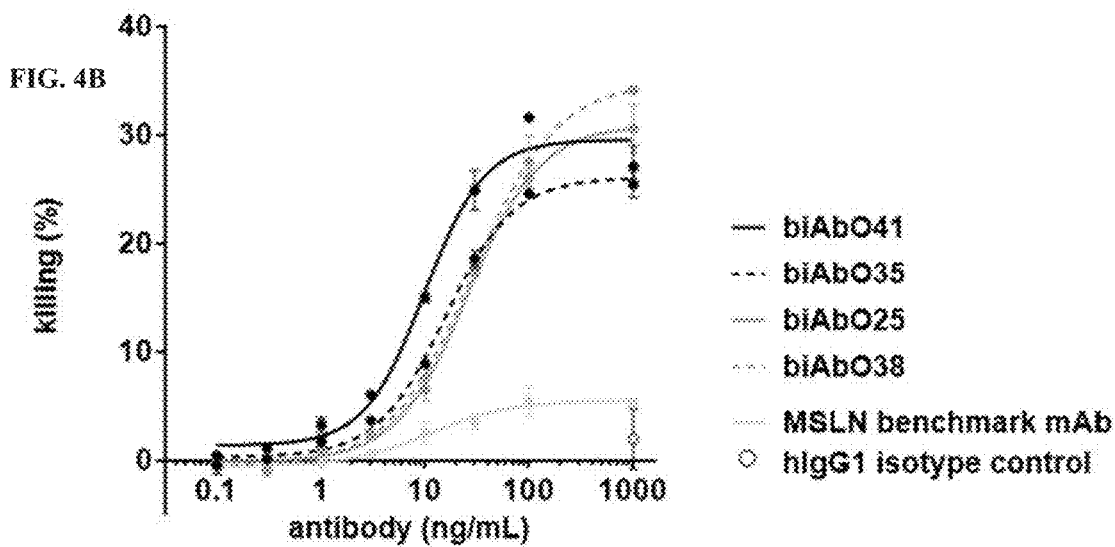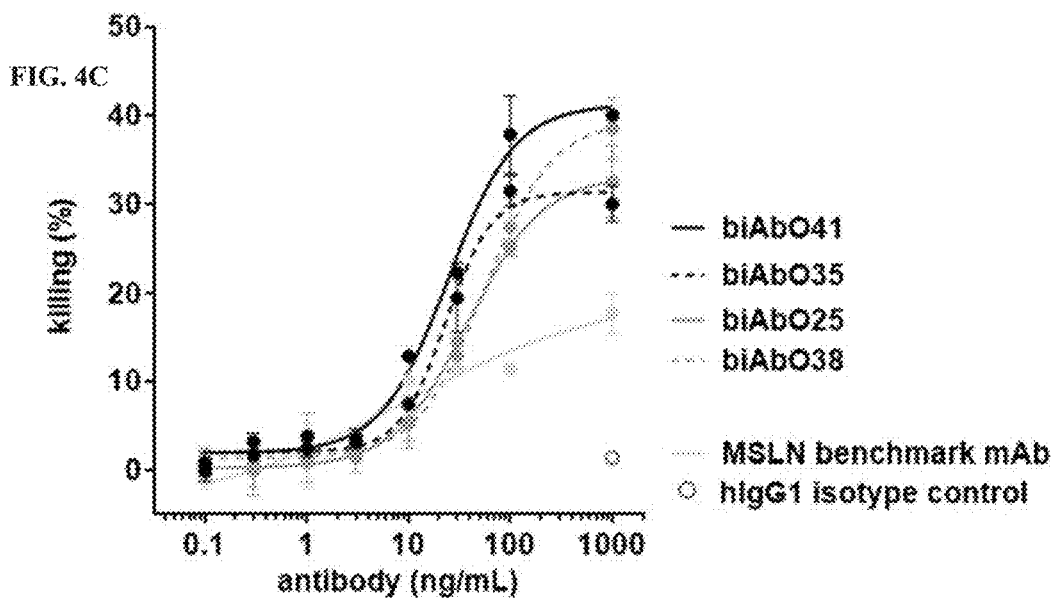

SEQUENCE LISTING

<160> NUMBER OF SEQ ID NOS: 300

<210> SEQ ID NO 1
<211> LENGTH: 1338
<212> TYPE: DNA
<213> ORGANISM: Artificial Sequence
<220> FEATURE:
<223> OTHER INFORMATION: Synthetic Polynucleotide

<400> SEQUENCE: 1

```
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagttat     300
ggtgcttttg actactgggg ccagggaacc ctggtcacag tctcgagcgc ctccaccaag     360
ggcccatcgg tcttccccct ggcaccctcc tccaagagca cctctggggg cacagcggcc     420
ctgggctgcc tggtcaagga ctacttcccc gaaccggtga cagtctcgtg gaactcagga     480
gccctgacca gcggcgtgca caccttcccg gctgtcctac agtcctcagg actctactcc     540
ctcagcagcg tggtgactgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatctc gggaggagat gaccaagaac    1080
caggtcagcc tgacttgcct ggtcaaaggc ttctatccca gcgacatcgc cgtggagtgg    1140
gagagcaacg ggcagccgga gaacaactac aagaccacgc ctcccgtgct ggactccgac    1200
```

-continued

```
ggctccttct tcctctatag caagctcacc gtggacaagt ccaggtggca gcagggggaac    1260 gtcttctcat gctccgtgat gcatgaggct ctgcacaacc actacacgca gaagagcctc    1320
tccctgtctc cgggttaa                                                   1338
```

<210> SEQ ID NO 2
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 3
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 3
gacatccaga tgacccagtc tccatcctcc ctgtctgcat ctgtaggaga cagagtcacc    60
atcacttgcc aggcgagtca ggacattaat aagtatttaa attggtatca gcagaaacca   120
gggaaagccc ctaagctcct gatctacggt gcatccaggt tggaaacagg ggtcccatca   180
aggttcagtg gaagtggatc tgggacagat tttactttca ccatcagcag cctgcagcct   240
gaagatattg caacatatta ctgtcagcag aagcaccccc gggggccgag gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttaa              648

<210> SEQ ID NO 4
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Gln Gln Lys His Pro Arg Gly Pro
            85                  90                  95

Arg Thr Phe Gly Gln Gly Thr Lys Val Glu Ile Lys Arg Thr Val Ala
        100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 5
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 5
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg gaagtggatc tgggacagat tttactttca ccatcagcag cctgcagcct     240
gaagatattg caacatatta ctgtcagcag aagcaccccc ggaacccgag gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 6
<211> LENGTH: 215
<212> TYPE: PRT
<213> ORGANISM: Artificial Sequence
<220> FEATURE:
<223> OTHER INFORMATION: Artificial Polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

```
Tyr Gly Ala Ser Arg Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Lys His Pro Arg Asn Pro
                 85                  90                  95

Arg Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 648
<212> TYPE: DNA
<213> ORGANISM: Artificial Sequence
<220> FEATURE:
<223> OTHER INFORMATION: Artificial Polynucleotide

<400> SEQUENCE: 7
gacatccaga tgacccagtc tccatcctcc ctgtctgcat ctgtaggaga cagagtcacc      60
atcacttgcc aggcgagtca gtccattagt agttatttaa attggtatca gcagaaacca    120
gggaaagccc ctaagctcct gatctacgct gcatcctcgt tggaaacagg gtcccatca    180 aggttcagtg gaagtggatc tgggacagat tttactttca ccatcagcag cctgcagcct    240
gaagatattg caacatatta ctgtcagcag aagcaccccc gggggccgag gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                 648

<210> SEQ ID NO 8
<211> LENGTH: 215
<212> TYPE: PRT
<213> ORGANISM: Artificial Sequence
<220> FEATURE:
<223> OTHER INFORMATION: Artificial Polypeptide
```

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 9
<211> LENGTH: 648
<212> TYPE: DNA
<213> ORGANISM: Artificial Sequence
<220> FEATURE:
<223> OTHER INFORMATION: Aritificial Polynucleotide

<400> SEQUENCE: 9
gacatccaga tgacccagtc tccatcctcc ctgtctgcat ctgtaggaga cagagtcacc        60
atcacttgcc aggcgagtca ggacattaat aagtatttaa attggtatca gcagaaacca       120
gggaaagccc ctaagctcct gatctacggt gcatccaggt tggaaacagg ggtcccatca       180
aggttcagtg gaagtggatc tgggacagat tttactttca ccatcagcag cctgcagcct       240
gaagatattg caacatatta ctgtcagcag aagcaccccc ggtacccgag gaccttcggc       300
caagggacca aggtggaaat caaacgtacg gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca aagcagacta cgagaaacac aaagtctacg cctgcgaagt cacccatcag       600
ggcctgagct cgcccgtcac aaagagcttc aacaggggag agtgttaa                    648

<210> SEQ ID NO 10
<211> LENGTH: 215
<212> TYPE: PRT
<213> ORGANISM: Artificial Sequence
<220> FEATURE:
<223> OTHER INFORMATION: Artificial Polypeptide

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Tyr Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 11
<211> LENGTH: 648
<212> TYPE: DNA
<213> ORGANISM: Artificial Sequence
<220> FEATURE:
<223> OTHER INFORMATION: Artificial Polynucleotide

<400> SEQUENCE: 11

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag ttccacaagc ggcggccgca gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
```

```
acgctgagca aagcagacta cgagaaacac aaagtctacg cctgcgaagt cacccatcag    600
ggcctgagct cgcccgtcac aaagagcttc aacaggggag agtgttaa                 648
```

```
<210> SEQ ID NO 12
<211> LENGTH: 215
<212> TYPE: PRT
<213> ORGANISM: Artificial Sequence
<220> FEATURE:
<223> OTHER INFORMATION: Artificial Polypeptide

<400> SEQUENCE: 12
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 13
<211> LENGTH: 648
<212> TYPE: DNA
<213> ORGANISM: Artificial Sequence
<220> FEATURE:
<223> OTHER INFORMATION: Artificial Polynucleotide

<400> SEQUENCE: 13
```

```
gacatccaga tgacccagtc tccatcctcc ctgtctgcat ctgtaggaga cagagtcacc    60
atcacttgcc gggcaagtca gagcattgcg aggtatttaa attggtatca gcagaaacca    120
gggaaagccc ctaagctcct gatctatgct gcatccagtt tgcaaagtgg gtcccatca    180 aggttcagtg gcagtggatc tgggacagat ttcactctca ccatcagcag tctgcaacct    240
gaagattttg caacttacta ctgtcagcag ttccataagc gtcgccgca gaccttcggc    300 caagggacca aggtggaaat caaacgtacg gtggctgcac catctgtctt catcttcccg    360
ccatctgatg agcagttgaa atctggaact gcctctgttg tgtgcctgct gaataacttc    420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa                 648

<210> SEQ ID NO 14
<211> LENGTH: 215
<212> TYPE: PRT
<213> ORGANISM: Artificial Sequence
<220> FEATURE:
<223> OTHER INFORMATION: Artificial Polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ala Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 15
gacatccaga tgacccagtc tccatcctcc ctgtctgcat ctgtaggaga cagagtcacc    60
atcacttgcc gggcaagtca gagcattggt aagtatttaa attggtatca gcagaaacca    120
gggaaagccc ctaagctcct gatctatgcg gcatccaggt tgcaaagtgg ggtcccatca    180
aggttcagtg gcagtggatc tgggacagat ttcactctca ccatcagcag tctgcaacct    240
gaagattttg caacttacta ctgtcagcag aagcacccgc gtgccccgcg gaccttcggc    300
```

```
caagggacca aggtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagacta cgagaaacac aaagtctacg cctgcgaagt cacccatcag      600
ggcctgagct cgcccgtcac aaagagcttc aacaggggag agtgttaa                  648
```

<210> SEQ ID NO 16
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 17
<211> LENGTH: 648
<212> TYPE: DNA
<213> ORGANISM: Artificial Sequence
<220> FEATURE:
<223> OTHER INFORMATION: Artificial Polynucleotide

<400> SEQUENCE: 17

```
gacatccaga tgacccagtc tccatcctcc ctgtctgcat ctgtaggaga cagagtcacc       60
atcacttgcc gggcaagtca gagcattgat aaggtattta attggtatca gcagaaacca      120
gggaaagccc ctaagctcct gatctatgct gcatccagtt tgcaaagtgg ggtcccatca      180
```

```
aggttcagtg gcagtggatc tgggacagat tcactctca ccatcagcag tctgcaacct    240
gaagattttg caacttacta ctgtcagcag aagcatcccc gtgggccgag gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa    648
```

<210> SEQ ID NO 18
<211> LENGTH: 215
<212> TYPE: PRT
<213> ORGANISM: Artificial Sequence
<220> FEATURE:
<223> OTHER INFORMATION: Artificial Polypeptide

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 19
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 19

```
gacatccaga tgacccagtc tccatcctcc ctgtctgcat ctgtaggaga cagagtcacc      60
atcacttgcc aggcgagtca ggacattaat aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag aagcatcccc gtggcccgcg gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa                 648
```

<210> SEQ ID NO 20
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 21
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 21

```
gacatccaga tgacccagtc tccatcctcc ctgtctgcat ctgtaggaga cagagtcacc      60
atcacttgcc gggcaagtca gagcattaat aggtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag aagcatccgc gtgggccgag gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648
```

<210> SEQ ID NO 22
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 23
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 23
gacatccaga tgacccagtc tccatcctcc ctgtctgcat ctgtaggaga cagagtcacc    60
atcacttgcc gggcaagtca gagcattggt aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag atgcatccgc gtgcgccgaa gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag acagcaccct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttaa               648

<210> SEQ ID NO 24
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 25
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 25
gacatccaga tgacccagtc tccatcctcc ctgtctgcat ctgtaggaga cagagtcacc    60
atcacttgcc gggtaagtca gagcattagt aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aggcatcccc gtgggccgag caccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaa                648

<210> SEQ ID NO 26
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Val Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Ser Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 648
<212> TYPE: DNA
<213> ORGANISM: Artificial Sequence
<220> FEATURE:
<223> OTHER INFORMATION: Artificial Polynucleotide

<400> SEQUENCE: 27
gacatccaga tgacccagtc tccatcctcc ctgtctgcat ctgtaggaga cagagtcacc      60
atcacttgcc aggcgagtca ggacattaat aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag aggcatcccg tgccccgcg  gaccttcggc    300 caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa              648

<210> SEQ ID NO 28
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Ala Pro
                85                  90                  95
```

```
Arg Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 29
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 29

```
gacatccaga tgacccagtc tccatcctcc ctgtctgcat ctgtaggaga cagagtcacc      60
atcacttgcc gggcaagtca gagcattagt aagtatttaa attggtatca gcagaaacca     120
gggaaagccc ctaagctcct gatctatgct gcatccactt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgcgccgaa gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648
```

<210> SEQ ID NO 30
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 31
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 31
gacatccaga tgacccagtc tccatcctcc ctgtctgcat ctgtaggaga cagagtcacc      60
atcacttgcc aggcgagtca ggacattaat aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag cgccatccgc gtggcccgag gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                648

<210> SEQ ID NO 32
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 32

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Asn Arg Tyr
             20                  25                  30
```

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg His Pro Arg Gly Pro
                 85                  90                  95

Arg Thr Phe Gly Gln Gly Thr Lys Val Glu Ile Lys Arg Thr Val Ala
             100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
 130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 33
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 33
gacatccaga tgacccagtc tccatcctcc ctgtctgcat ctgtaggaga cagagtcacc    60
atcacttgcc gggcaagtca gagcattggt aggtatttaa attggtatca gcagaaacca   120
gggaaagccc ctaagctcct gatctatgcg catccaggt tgcaaagtgg ggtcccatca    180
aggttcagtg gcagtggatc tgggacagat ttcactctca ccatcaacag tctgcaacct   240
gaagattttg caacttacta ctgtcagcag aagcatcccc gtgcgccgag gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagacta cgagaaacac aaagtctacg cctgcgaagt cacccatcag   600
ggcctgagct cgcccgtcac aaagagcttc aacaggggag agtgttaa               648

<210> SEQ ID NO 34
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 35
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 35
gacatccaga tgacccagtc tccatcctcc ctgtctgcat ctgtaggaga cagagtcacc      60
atcacttgcc gggcaagtca gagcattgat aagtatttaa attggtatca gcagaaacca     120
gggaaagccc ctaagctcct gatctatgcg gcatccaggt tgcaaagtgg ggtcccatca     180
aggttcagtg gcagtggatc tgggacagat tcactctca ccatcagcag tctgcaacct      240
gaagattttg caacttacta ctgtcagcag cggcataagc gttccccgca gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgttaa                  648

<210> SEQ ID NO 36
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Lys Arg Ser Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 37
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 37

```
gacatccaga tgacccagtc tccatcctcc ctgtctgcat ctgtaggaga cagagtcacc      60
atcacttgcc gggcaagtca gagcattgat aagtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag aagcatccgc gtcgccgcg gaccttcggc     300 caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
```

```
acgctgagca aagcagacta cgagaaacac aaagtctacg cctgcgaagt cacccatcag    600
ggcctgagct cgcccgtcac aaagagcttc aacaggggag agtgttaa                 648
```

<210> SEQ ID NO 38
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 38

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Lys Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Lys His Pro Arg Ala Pro
                 85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 39
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 39

```
gacatccaga tgacccagtc tccatcctcc ctgtctgcat ctgtaggaga cagagtcacc    60
atcacttgcc gggcaagtca gagcattggg aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcatccgc gtagcccgaa gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa                648
```

<210> SEQ ID NO 40
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 41
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 41

```
gacatccaga tgacccagtc tccatcctcc ctgtctgcat ctgtaggaga cagagtcacc    60
atcacttgcc gggcaagtca gagcattagt aggtatttaa attggtatca gcagaaacca    120
gggaaagccc ctaagctcct gatctatgct gcatccaatt tgcaaagtgg ggtcccatca    180
aggttcagtg gcagtggatc tgggacagat ttcactctca ccatcagcag tctgcaacct    240
gaagattttg caacttacta ctgtcagcag atgcatccgc gtgggccgaa gaccttcggc    300
```

```
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                 648
```

<210> SEQ ID NO 42
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 43
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 43

```
gacatccaga tgacccagtc tccatcctcc ctgtctgcat ctgtaggaga cagagtcacc    60
atcacttgcc gggcaagtca gagcattgct tcttatgtaa attggtatca gcagaaacca    120
gggaaagccc ctaagctcct gatctatgct gcatccggtt tgcaaagtgg ggtcccatca    180
```

```
aggttcagtg gcagtggatc tgggacagat tcactctca ccatcagcag tctgcaacct    240
gaagattttg caacttacta ctgtcagcag ttccataagc gtcggccgca gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                 648
```

<210> SEQ ID NO 44
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Val Asn Trp Tyr Gln Gln Lys Pro Gly Lys Ala Pro Lys Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 45
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 45

```
gacatccaga tgacccagtc tccatcctcc ctgtctgcat ctgtaggaga cagagtcacc      60
atcacttgcc gggcaagtca gagcattggg aggtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgggccgaa gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648
```

<210> SEQ ID NO 46
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 47
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 47

```
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctataat gcatccactt tgcaaagtgg ggtcccatca   180
aggttcagtg gcagtggatc tgggacagat ttcactctca ccatcagcag tctgcaacct   240
gaagattttg caacttacta ctgtcagcag aggcatccgc gtgggccgcg caccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttaa               648
```

<210> SEQ ID NO 48
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 49
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 49
gacatccaga tgacccagtc tccatcctcc ctgtctgcat ctgtaggaga cagagtcacc     60
atcacttgcc gggcaagtca gagcattagt aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag aagcatccgc gtagcccgcg gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa                 648

<210> SEQ ID NO 50
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ser Pro
            85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 51
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 51
gacatccaga tgacccagtc tccatcctcc ctgtctgcat ctgtaggaga cagagtcacc      60
atcacttgcc gggcaagtca gagcattgct aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag ttccataagc gtagcccgca gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                648

<210> SEQ ID NO 52
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ser Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 53
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 53
gacatccaga tgacccagtc tccatcctcc ctgtctgcat ctgtaggaga cagagtcacc     60
atcacttgcc gggcaagtca gagcattagt aagtatttaa attggtatca gcagaaacca    120
gggaaagccc ctaagctcct gatctataat gcatccaatt tgcaaagtgg ggtcccatca    180
aggttcagtg gcagtggatc tgggacagat ttcactctca ccatcagcag tctgcaacct    240
gaagattttg caacttacta ctgtcagcag aggcatccgc gtgggccgac caccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                  648

<210> SEQ ID NO 54
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

```
Thr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 55
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 55
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag atgcacccgc gcgccccgaa gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 56
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

| | | | | | | | | | | | | |
|---|---|---|---|---|---|---|---|---|---|---|---|---|
|Ser|Gly|Ser|Gly|Thr|Asp|Phe|Thr|Leu|Thr|Ile|Ser|Ser|Leu|Gln|Pro|
|65| | | |70| | | |75| | | |80|

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 57
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 57
gacatccaga tgacccagtc tccatcctcc ctgtctgcat ctgtaggaga cagagtcacc      60
atcacttgcc gggcaagtca gagcattagt aagtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gctcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                 648

<210> SEQ ID NO 58
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

```
Leu Asn Trp Tyr Gln Gln Lys Pro Gly Lys Ala Pro Lys Leu Leu Ile
         35                  40                  45

Tyr Ala Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ser Pro
                 85                  90                  95

Lys Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 59
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 59
gacatccaga tgacccagtc tccatcctcc ctgtctgcat ctgtaggaga cagagtcacc    60
atcacttgcc aggcgagtca ggacattgct aagtatttaa attggtatca gcagaaacca   120
gggaaagccc ctaagctcct gatctatgct gcatccgctt tgcaaagtgg ggtcccatca   180
aggttcagtg gcagtggatc tgggacagat ttcactctca ccatcagcag tctgcaacct   240
gaagattttg caacttacta ctgtcagcag atgcatcctc gctcgccgaa aaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaa               648

<210> SEQ ID NO 60
<211> LENGTH: 215
<212> TYPE: PRT
<213> ORGANISM: Artificial Sequence
<220> FEATURE:
<223> OTHER INFORMATION: Synthetic Polypeptide
```

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 61
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 61
gacatccaga tgacccagtc tccatcctcc ctgtctgcat ctgtaggaga cagagtcacc      60
atcacttgcc gggcaagtca gagcattgct agtatttaa attggtatca gcagaaacca     120
gggaaagccc ctaagctcct gatctatgcg gcatccaggt tgcaaagtgg ggtcccatca     180
aggttcagtg gcagtggatc tgggacagat tcactctca ccatcagcag tctgcaacct     240
gaagattttg caacttacta ctgtcagcag atgcatcctc gcgcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                648

```
<210> SEQ ID NO 62
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 63
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 63
gacatccaga tgacccagtc tccatcctcc ctgtctgcat ctgtaggaga cagagtcacc     60
atcacttgcc gggcaagtca gagcattgcg agttatttaa attggtatca gcagaaacca   120
gggaaagccc ctaagctcct gatctatgcg gcatccaggt tgcaaagtgg ggtcccatca   180
aggttcagtg gcagtggatc tgggacagat tcactctcac catcagcagt ctgcaacct    240 gaagattttg caacttacta ctgtcagcag atgcatcctc gctcgccgaa aaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
```

```
acgctgagca aagcagacta cgagaaacac aaagtctacg cctgcgaagt cacccatcag    600
ggcctgagct cgcccgtcac aaagagcttc aacaggggag agtgttaa                648
```

<210> SEQ ID NO 64
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 64

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 65
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 65

```
gacatccaga tgacccagtc tccatcctcc ctgtctgcat ctgtaggaga cagagtcacc    60
atcacttgcc gggcaagtca gaacattggt aagtatttaa attggtatca gcagaaacca   120
gggaaagccc ctaagctcct gatctatagt gcatccaggt tgcaaagtgg gtcccatca   180 aggttcagtg gcagtggatc tgggacagat ttcactctca ccatcagcag tctgcaacct   240
gaagattttg caacttacta ctgtcagcag atgcatcctc gcgcgccgaa aaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
```
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648

<210> SEQ ID NO 66
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Lys Tyr
            20                  25                  30

Leu Asn Trp Tyr Gln Gln Lys Pro Gly Lys Ala Pro Lys Leu Leu Ile
        35                  40                  45

Tyr Ser Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 67
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 67
gacatccaga tgacccagtc tccatcctcc ctgtctgcat ctgtaggaga cagagtcacc     60
atcacttgcc gggcaagtca gagcattagt aggtatttaa attggtatca gcagaaacca    120
gggaaagccc ctaagctcct gatctattct gcatcctctt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgccccgaa aaccttcggc    300

-continued

| | |
|---|---|
| caagggacca aggtggaaat caaacgtacg gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca agcagacta cgagaaacac aaagtctacg cctgcgaagt cacccatcag | 600 |
| ggcctgagct cgcccgtcac aaagagcttc aacaggggag agtgttaa | 648 |

<210> SEQ ID NO 68
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 69
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 69

| | |
|---|---|
| gacatccaga tgacccagtc tccatcctcc ctgtctgcat ctgtaggaga cagagtcacc | 60 |
| atcacttgcc gggcaagtca gagcattgat aagtatttaa attggtatca gcagaaacca | 120 |
| gggaaagccc ctaagctcct gatctatgct gcatccagt tgcaaagtgg ggtcccatca | 180 |

```
aggttcagtg gcagtggatc tgggacagat tcactctca ccatcagcag tctgcaacct      240
gaagattttg caacttacta ctgtcagcag atgcatcctc gcgggccgaa aaccttcggc      300
caagggacca aggtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgttaa                  648

<210> SEQ ID NO 70
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 71
<211> LENGTH: 648
<212> TYPE: DNA
<213> ORGANISM: Artificial Sequence
<220> FEATURE:
<223> OTHER INFORMATION: Synthetic Polynucleotide
```

<400> SEQUENCE: 71

```
gacatccaga tgacccagtc tccatcctcc ctgtctgcat ctgtaggaga cagagtcacc      60
atcacttgcc gggcaagtca gagcattggt aagtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gcgcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                   648
```

<210> SEQ ID NO 72
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 72

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Lys Tyr
                 20                  25                  30

Leu Asn Trp Tyr Gln Gln Lys Pro Gly Lys Ala Pro Lys Leu Leu Ile
             35                  40                  45

Tyr Ala Ala Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 73
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 73

```
cagtctgccc tgactcagcc tgcctccgtg tctgggtctc ctggacagtc gatcaccatc    60
tcctgcactg gaaccagcag tgacgttggt ggttataact atgtctcctg gtaccaacag   120
cacccaggca agcccccaa actcatgatt tatgaggtca gtaatcggcc ctcaggggtt    180
tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg gagggaccaa gctgaccgtc ctaggtcagc ccaaggctgc ccctcggtc    360
actctgttcc cgccctcctc tgaggagctt caagccaaca ggccacact ggtgtgtctc    420
ataagtgact tctacccggg agccgtgaca gtggcttgga agcagatag cagccccgtc    480
aaggcgggag tggagaccac cacaccctcc aaacaaagca caacaagta cgcggccagc   540
agctatctga gcctgacgcc tgagcagtgg aagtcccaca gaagctacag ctgccaggtc   600
acgcatgaag ggagcaccgt ggagaagaca gtggccccta cagaatgttc ataa         654
```

<210> SEQ ID NO 74
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 74

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190
```

His Arg Ser Tyr Ser Cys Gln Val Thr His Glu Gly Ser Thr Val Glu
            195                 200                 205

Lys Thr Val Ala Pro Thr Glu Cys Ser
        210                 215

<210> SEQ ID NO 75
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 75
cagtctgccc tgactcagcc tgcctccgtg tctgggtctc ctggacagtc gatcaccatc      60
tcctgcactg gaaccagcag tgacgttggg aaggcgaact atgtctcctg gtaccaacag     120
cacccaggca aagcccccaa actcatgatt tataaggata gtgatcggcc ctcagggggtt    180 tctaatcgct tctctggctc caagtctggc aacacggcct ccctgaccat ctctgggctc     240
caggctgagg acgaggctga ttattactgc agctcatatg attggtggtt ccgcccaag      300 gtgttcggcg agggaccaa gctgaccgtc ctaggtcagc ccaaggctgc cccctcggtc     360
actctgttcc cgccctcctc tgaggagctt caagccaaca ggccacact ggtgtgtctc     420 ataagtgact tctacccggg agccgtgaca gtggcttgga agcagatag cagccccgtc     480 aaggcgggag tggagaccac cacaccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggccccta cagaatgttc ataa           654

<210> SEQ ID NO 76
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 76

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Ala
            20                  25                  30

Asn Tyr Val Ser Trp Tyr Gln Gln His Pro Gly Lys Ala Pro Lys Leu
        35                  40                  45

Met Ile Tyr Lys Asp Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

```
Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
        210                 215
```

<210> SEQ ID NO 77
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 77

```
cagtctgccc tgactcagcc tgcctccgtg tctgggtctc ctggacagtc gatcaccatc    60
tcctgcactg gaaccagcag tgacgttagg gggaataact atgtctcctg gtaccaacag   120
cacccaggca aagcccccaa actcatgatt tatgagaata gtaagcggcc ctcaggggtt   180
tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg gagggaccaa gctgaccgtc ctaggtcagc ccaaggctgc ccctcggtc    360 actctgttcc cgccctcctc tgaggagctt caagccaaca aggccacact ggtgtgtctc   420
ataagtgact tctacccggg agccgtgaca gtggcttgga agcagatag cagccccgtc   480 aaggcgggag tggagaccac cacaccctcc aaacaaagca caacaagta cgcggccagc   540 agctatctga gcctgacgcc tgagcagtgg aagtcccaca agctacag ctgccaggtc    600 acgcatgaag ggagcaccgt ggagaagaca gtggccccta cagaatgttc ataa         654
```

<210> SEQ ID NO 78
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 78

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Gly Asn
            20                  25                  30

Asn Tyr Val Ser Trp Tyr Gln Gln His Pro Gly Lys Ala Pro Lys Leu
            35                  40                  45

Met Ile Tyr Glu Asn Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
            85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125
```

Glu Leu Gln Ala Asn Lys Ala Thr Leu Val Cys Leu Ile Ser Asp Phe
     130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 79
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 79
cagtctgccc tgactcagcc tgcctccgtg tctgggtctc ctggacagtc gatcaccatc      60
tcctgcactg gaaccagcag tgacgttagt gcgaggaact atgtctcctg gtaccaacag     120
cacccaggca agcccccaa actcatgatt tatgagagta gtaagcggcc ctcaggggtt      180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc ctaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcttgga agcagatag cagccccgtc     480 aaggcgggag tggagaccac cacaccctcc aaacaaagca acaacaagta cgcggccagc     540
agctatctga gcctgacgcc tgagcagtgg aagtcccaca gaagctacag ctgccaggtc     600
acgcatgaag ggagcaccgt ggagaagaca gtggccccta cagaatgttc ataa            654

<210> SEQ ID NO 80
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 80

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Ser Ala Arg
            20                  25                  30

Asn Tyr Val Ser Trp Tyr Gln Gln His Pro Gly Lys Ala Pro Lys Leu
        35                  40                  45

Met Ile Tyr Glu Ser Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

```
Phe Arg Pro Lys Val Phe Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
            210                 215
```

<210> SEQ ID NO 81
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 81

```
cagtctgccc tgactcagcc tgcctccgtg tctgggtctc ctggacagtc gatcaccatc      60
tcctgcacta gaaccagcag tgacgttaat aatactaact atgtctcctg gtaccaacag     120
cacccaggca agcccccaa actcatgatt tataagacta gtggtcggcc ctcagggggtt     180 tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg agggaccaa gctgaccgtc ctaggtcagc ccaaggctgc ccctcggtc      360 actctgttcc cgccctcctc tgaggagctt caagccaaca ggccacact ggtgtgtctc      420 ataagtgact ctacccgggg agccgtgaca gtggcttgga agcagatag cagcccgtc      480 aaggcgggag tggagaccac cacacccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggcccta cagaatgttc ataa           654
```

<210> SEQ ID NO 82
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 82

```
Gln Ser Ala Leu Thr Gln Pro Ala Ser Val Ser Gly Ser Pro Gly Gln
1               5                   10                  15

Ser Ile Thr Ile Ser Cys Thr Arg Thr Ser Ser Asp Val Asn Asn Thr
            20                  25                  30

Asn Tyr Val Ser Trp Tyr Gln Gln His Pro Gly Lys Ala Pro Lys Leu
        35                  40                  45

Met Ile Tyr Lys Thr Ser Gly Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215
```

<210> SEQ ID NO 83
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 83

```
cagtctgccc tgactcagcc tgcctccgtg tctgggtctc ctggacagtc gatcaccatc    60
tcctgcactg gaaccagcag tgacgttaat tctgctaact atgtctcctg gtaccaacag   120
cacccaggca agcccccaa actcatgatt tataagagta gtagtcggcc ctcagggtt    180 tctaatcgct tctctggctc caagtctggc aacacggcct ccctgaccat ctctgggctc   240
caggctgagg acgaggctga ttattactgc agctcatatg attggtggtt ccgcccaag    300 gtgttcggcg agggaccaa gctgaccgtc ctaggtcagc ccaaggctgc ccctcggtc    360 actctgttcc cgccctcctc tgaggagctt caagccaaca ggccacact ggtgtgtctc    420 ataagtgact tctacccggg agccgtgaca gtggcttgga agcagatag cagccccgtc   480 aaggcgggag tggagaccac cacaccctcc aaacaaagca acaacaagta cgcggccagc   540
agctatctga gcctgacgcc tgagcagtgg aagtcccaca gaagctacag ctgccaggtc   600
acgcatgaag ggagcaccgt ggagaagaca gtggccccta cagaatgttc ataa         654
```

<210> SEQ ID NO 84
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 84

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Asn Ser Ala
             20                  25                  30
```

Asn Tyr Val Ser Trp Tyr Gln Gln His Pro Gly Lys Ala Pro Lys Leu
             35                  40                  45

Met Ile Tyr Lys Ser Ser Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Thr Lys Leu Thr Val Leu Gly
             100                 105                 110

Gln Pro Lys Ala Ala Pro Ser Val Thr Leu Phe Pro Pro Ser Ser Glu
             115                 120                 125

Glu Leu Gln Ala Asn Lys Ala Thr Leu Val Cys Leu Ile Ser Asp Phe
         130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 85
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 85
cagtctgccc tgactcagcc tgcctccgtg tccgggtctc ctggacagtc gatcaccatc      60
tcctgcactg gaaccagcag tgacgttgag aggaagaact atgtctcctg gtaccaacag     120
cacccaggca agcccccaa actcatgatt tataagaata gtactcggcc ctcagggggtt     180 tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc ctaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcttgga agcagatag cagcccgtc      480 aaggcgggag tggagaccac cacccctcc aaacaaagca acaacaagta cgcggccagc     540
agctatctga gcctgacgcc tgagcagtgg aagtcccaca agctacag ctgccaggtc      600 acgcatgaag ggagcaccgt ggagaagaca gtggccccta cagaatgttc ataa          654

<210> SEQ ID NO 86
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 86

| | | | | | | | | | | | | | | |
|---|---|---|---|---|---|---|---|---|---|---|---|---|---|---|
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Glu Arg Lys
            20                  25                  30

Asn Tyr Val Ser Trp Tyr Gln Gln His Pro Gly Lys Ala Pro Lys Leu
        35                  40                  45

Met Ile Tyr Lys Asn Ser Thr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 87
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 87
cagtctgccc tgactcagcc tgcctccgtg tctgggtctc ctggacagtc gatcaccatc      60
tcctgcactg gaaccagcag tgacgttagg gcggctaact atgtctcctg gtaccaacag     120
cacccaggca agcccccaa actcatgatt tataagaata gtactcggcc ctcaggggtt      180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc ctaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcttgga agcagatag cagccccgtc      480 aaggcgggag tggagaccac cacccctcc aaacaaagca acaacaagta cgcggccagc     540
agctatctga gcctgacgcc tgagcagtgg aagtcccaca gaagctacag ctgccaggtc     600
acgcatgaag ggagcaccgt ggagaagaca gtggccccta cagaatgttc ataa           654

<210> SEQ ID NO 88
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 88

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Ala Ala
            20                  25                  30

Asn Tyr Val Ser Trp Tyr Gln Gln His Pro Gly Lys Ala Pro Lys Leu
        35                  40                  45

Met Ile Tyr Lys Asn Ser Thr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 89
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 89

```
cagtctgccc tgactcagcc tgcctccgtg tctgggtctc ctggacagtc gatcaccatc      60
tcctgcactg gaaccagcag tgacgttagg agggctaact atgtctcctg gtaccaacag     120
cacccaggca aagcccccaa actcatgatt tatcaggata gtagtcggcc ctcagggctt     180
tctaatcgct tctctggctc caagtctggc aacacggcct ccctgaccat ctctgggctc     240
caggctgagg acgaggctga ttattactgc agctcatatg attggtggtt ccgcccaag     300 gtgttcggcg gagggaccaa gctgaccgtc ctaggtcagc ccaaggctgc ccctcggtc     360 actctgttcc cgccctcctc tgaggagctt caagccaaca aggccacact ggtgtgtctc     420
ataagtgact tctacccggg agccgtgaca gtggcttgga agcagatag cagccccgtc     480 aaggcgggag tggagaccac cacaccctcc aaacaaagca acaacaagta cgcggccagc     540
```

-continued

```
agctatctga gcctgacgcc tgagcagtgg aagtcccaca gaagctacag ctgccaggtc    600
acgcatgaag ggagcaccgt ggagaagaca gtggccccta cagaatgttc ataa          654
```

<210> SEQ ID NO 90
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 90

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Arg Arg Ala
             20                  25                  30

Asn Tyr Val Ser Trp Tyr Gln Gln His Pro Gly Lys Ala Pro Lys Leu
         35                  40                  45

Met Ile Tyr Gln Asp Ser Ser Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 91
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 91

```
cagtctgccc tgactcagcc tgcctccgtg tctgggtctc ctggacagtc gatcaccatc    60
tcctgcactg gaaccagcag tgacgttagg gctaataact atgtctcctg gtaccaacag   120
cacccaggca agccccccaa actcatgatt tatgagagta gtcgcggcc ctcagggtt    180 tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc ctaggtcagc ccaaggctgc ccctcggtc    360 actctgttcc cgccctcctc tgaggagctt caagccaaca aggccacact ggtgtgtctc   420
```

```
ataagtgact tctacccggg agccgtgaca gtggcttgga aagcagatag cagccccgtc    480
aaggcgggag tggagaccac cacaccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggccccta cagaatgttc ataa          654
```

<210> SEQ ID NO 92
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 92

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Ala Asn
            20                  25                  30

Asn Tyr Val Ser Trp Tyr Gln Gln His Pro Gly Lys Ala Pro Lys Leu
        35                  40                  45

Met Ile Tyr Glu Ser Ser Ala Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 93
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 93

```
cagtctgccc tgactcagcc tgcctccgtg tctgggtctc ctggacagtc gatcaccatc    60
tcctgcactg gaaccagcag tgacgtttat tataataagt atgtctcctg gtaccaacag    120
cacccaggca agccccccaa actcatgatt tatgagagta gtaagcggcc ctcaggggtt    180
tctaatcgct tctctggctc caagtctggc aacacggcct ccctgaccat ctctgggctc    240
caggctgagg acgaggctga ttattactgc agctcatatg attggtggtt ccgccccaag    300
```

| | |
|---|---|
| gtgttcggcg agggaccaa gctgaccgtc ctaggtcagc ccaaggctgc cccctcggtc | 360 |
| actctgttcc cgccctcctc tgaggagctt caagccaaca aggccacact ggtgtgtctc | 420 |
| ataagtgact tctacccggg agccgtgaca gtggcttgga aagcagatag cagccccgtc | 480 |
| aaggcgggag tggagaccac cacaccctcc aaacaaagca acaacaagta cgcggccagc | 540 |
| agctatctga gcctgacgcc tgagcagtgg aagtcccaca gaagctacag ctgccaggtc | 600 |
| acgcatgaag ggagcaccgt ggagaagaca gtggccccta cagaatgttc ataa | 654 |

<210> SEQ ID NO 94
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 94

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Tyr Tyr Asn
            20                  25                  30

Lys Tyr Val Ser Trp Tyr Gln Gln His Pro Gly Lys Ala Pro Lys Leu
        35                  40                  45

Met Ile Tyr Glu Ser Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 95
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 95

| | |
|---|---|
| cagtctgccc tgactcagcc tgcctccgtg tctgggtctc ctggacagtc gatcaccatc | 60 |
| tcctgcactg gaaccagcag tgacgtttat tataataagt atgtctcctg gtaccaacag | 120 |
| cacccaggca aagcccccaa actcatgatt tatgagagta gtaagcggcc ctcaggggtt | 180 |

```
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg gagggaccaa gctgaccgtc cta                                 333
```

<210> SEQ ID NO 96
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 96

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Tyr Tyr Asn
            20                  25                  30

Lys Tyr Val Ser Trp Tyr Gln Gln His Pro Gly Lys Ala Pro Lys Leu
        35                  40                  45

Met Ile Tyr Glu Ser Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110
```

<210> SEQ ID NO 97
<211> LENGTH: 675
<212> TYPE: DNA
<213> ORGANISM: Artificial Sequence
<220> FEATURE:
<223> OTHER INFORMATION: Synthetic Polynucleotide

<400> SEQUENCE: 97

```
cagcctgtgc tgactcagcc ggcttccctc tctgcatctc ctggagcatc agccagtctc    60
acctgcacct tgcacagtgg catctctgtt aaggattaca ggatatactg gtaccagcag    120 aagccaggc gtcctcccca gtatctcctg aggtacaagt ctaattcaga tatgcagcag    180
ggatctggag tccccagccg cttctctggg tccaaagatg cttcggccaa tgcagggatt    240
ttactcatct ctgggctcca gtctgaggat gaggctgact attactgtat gatttggcac    300
catggccatg ggactagtct tgtgttcggc ggagggacca agctgaccgt cctaggtcag    360
cccaaggctg ccccctcggt cactctgttc ccgccctcct ctgaggagct tcaagccaac    420
aaggccacac tggtgtgtct cataagtgac ttctaccgg gagccgtgac agtggcttgg    480
aaagcagata gcagccccgt caaggcggga gtggagacca ccacaccctc caaacaaagc    540
aacaacaagt acgcggccag cagctatctg agcctgacgc ctgagcagtg gaagtcccac    600
agaagctaca gctgccaggt cacgcatgaa gggagcaccg tggagaagac agtggcccct    660
acagaatgtt cataa                                                     675
```

<210> SEQ ID NO 98
<211> LENGTH: 224
<212> TYPE: PRT
<213> ORGANISM: Artificial Sequence
<220> FEATURE:
<223> OTHER INFORMATION: Synthetic Polypeptide

<400> SEQUENCE: 98

Gln Pro Val Leu Thr Gln Pro Ala Ser Leu Ser Ala Ser Pro Gly Ala
1               5                   10                  15

Ser Ala Ser Leu Thr Cys Thr Leu His Ser Gly Ile Ser Val Lys Asp
            20                  25                  30

Tyr Arg Ile Tyr Trp Tyr Gln Gln Lys Pro Gly Arg Pro Pro Gln Tyr
        35                  40                  45

Leu Leu Arg Tyr Lys Ser Asn Ser Asp Met Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His His Gly His Gly Thr Ser Leu Val Phe Gly Gly Gly
            100                 105                 110

Thr Lys Leu Thr Val Leu Gly Gln Pro Lys Ala Ala Pro Ser Val Thr
        115                 120                 125

Leu Phe Pro Pro Ser Ser Glu Glu Leu Gln Ala Asn Lys Ala Thr Leu
    130                 135                 140

Val Cys Leu Ile Ser Asp Phe Tyr Pro Gly Ala Val Thr Val Ala Trp
145                 150                 155                 160

Lys Ala Asp Ser Ser Pro Val Lys Ala Gly Val Glu Thr Thr Thr Pro
                165                 170                 175

Ser Lys Gln Ser Asn Asn Lys Tyr Ala Ala Ser Ser Tyr Leu Ser Leu
            180                 185                 190

Thr Pro Glu Gln Trp Lys Ser His Arg Ser Tyr Ser Cys Gln Val Thr
        195                 200                 205

His Glu Gly Ser Thr Val Glu Lys Thr Val Ala Pro Thr Glu Cys Ser
    210                 215                 220

<210> SEQ ID NO 99
<211> LENGTH: 657
<212> TYPE: DNA
<213> ORGANISM: Artificial Sequence
<220> FEATURE:
<223> OTHER INFORMATION: Synthetic Polynucleotide

<400> SEQUENCE: 99
cagtctgtgc tgactcagcc accctcagcg tctgggaccc ccggggcagag ggtcaccatc      60
tcttgttctg gaagcagctc caacatcgcg catgggcctg taaactggta ccagcagctc     120
ccaggaacgg cccccaaact cctcatctat gctactaatc atcgccctc agggtccct       180
gaccgatttt ctggctccaa gtctggcacc acagcctccc tgaccatcag tgggctccag     240
tctgaggatg aggctgatta ttactgtgct gcatatgatc ttacgggctg gtttgcgtat     300
gctgtgttcg gcggagggac caagctgacc gtcctaggtc agcccaaggc tgcccctcg      360
gtcactctgt tcccgccctc ctctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa       657

<210> SEQ ID NO 100
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 100

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Ala His Gly
            20                  25                  30

Pro Val Asn Trp Tyr Gln Gln Leu Pro Gly Thr Ala Pro Lys Leu Leu
        35                  40                  45

Ile Tyr Ala Thr Asn His Arg Pro Ser Gly Val Pro Asp Arg Phe Ser
    50                  55                  60

Gly Ser Lys Ser Gly Thr Thr Ala Ser Leu Thr Ile Ser Gly Leu Gln
65                  70                  75                  80

Ser Glu Asp Glu Ala Asp Tyr Tyr Cys Ala Ala Tyr Asp Leu Thr Gly
                85                  90                  95

Trp Phe Ala Tyr Ala Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 101
<211> LENGTH: 651
<212> TYPE: DNA
<213> ORGANISM: Artificial Sequence
<220> FEATURE:
<223> OTHER INFORMATION: Synthetic Polynucleotide

<400> SEQUENCE: 101

```
tcctatgtgc tgactcagcc accctcagtg tcagtggccc caggaaagac ggccaggatt      60
acctgtgggg gaaacaagat tggacaccgc gccgtgcact ggtaccagca gaagccaggc     120
caggcccctg tgctggtcat ctattatacc tatgatcggc cctcagggat tcctgagcga     180
ttctctggct ccaactctgg gaacacggcc accctgacca tcagcagggt cgaagccggg     240
gatgaggccg actattactg tcaggtgtgg gatgcgtcta gcgcgacgc gaatgttgtg      300 ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcttggaaag cagatagcag ccccgtcaag     480
gcgggagtgg agaccaccac accctccaaa caaagcaaca acaagtacgc ggccagcagc     540
```

```
tatctgagcc tgacgcctga gcagtggaag tcccacagaa gctacagctg ccaggtcacg    600
catgaaggga gcaccgtgga agacagtg gcccctacag aatgttcata a               651
```

<210> SEQ ID NO 102
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 102

Ser Tyr Val Leu Thr Gln Pro Pro Ser Val Ser Val Ala Pro Gly Lys
1               5                   10                  15

Thr Ala Arg Ile Thr Cys Gly Gly Asn Lys Ile Gly His Arg Ala Val
            20                  25                  30

His Trp Tyr Gln Gln Lys Pro Gly Gln Ala Pro Val Leu Val Ile Tyr
        35                  40                  45

Tyr Thr Tyr Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ala Ser Arg Arg Asp
                85                  90                  95

Ala Asn Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 103
<211> LENGTH: 675
<212> TYPE: DNA
<213> ORGANISM: Artificial Sequence
<220> FEATURE:
<223> OTHER INFORMATION: Synthetic Polynucleotide

<400> SEQUENCE: 103

```
cagcctgtgc tgactcagcc ggtttccctc tctgcatctc ctggagcatc agtcagtctc    60
acctgcacct tgcgcagtga catcagggtt agagattaca ggatattctg gtaccagcag   120
aagccaggga gtcctcccca gtatctcctg aggtacaaaa ccgactcaga taagcagcag   180
ggctctggag tccccagccg cttctctggg tccaaagatg cttcggccaa tgcagggatt   240
ttactcatct ctgggctcca gtctgaggat gaggctgact attactgtat gatttggcac   300
cgcaccacgg gcactagtct tgtgttcggc ggagggacca agctgaccgt cctaggtcag   360
cccaaggctg ccccctcggt cactctgttc ccgcccctcct ctgaggagct tcaagccaac   420
```

| | |
|---|---|
| aaggccacac tggtgtgtct cataagtgac ttctacccgg gagccgtgac agtggcttgg | 480 |
| aaagcagata gcagccccgt caaggcggga gtggagacca ccacaccctc caaacaaagc | 540 |
| aacaacaagt acgcggccag cagctatctg agcctgacgc tgagcagtg gaagtcccac | 600 |
| agaagctaca gctgccaggt cacgcatgaa gggagcaccg tggagaagac agtggcccct | 660 |
| acagaatgtt cataa | 675 |

<210> SEQ ID NO 104
<211> LENGTH: 224
<212> TYPE: PRT
<213> ORGANISM: Artificial Sequence
<220> FEATURE:
<223> OTHER INFORMATION: Synthetic Polypeptide

<400> SEQUENCE: 104

Gln Pro Val Leu Thr Gln Pro Val Ser Leu Ser Ala Ser Pro Gly Ala
1               5                   10                  15

Ser Val Ser Leu Thr Cys Thr Leu Arg Ser Asp Ile Arg Val Arg Asp
            20                  25                  30

Tyr Arg Ile Phe Trp Tyr Gln Gln Lys Pro Gly Ser Pro Pro Gln Tyr
        35                  40                  45

Leu Leu Arg Tyr Lys Thr Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Arg Thr Thr Gly Thr Ser Leu Val Phe Gly Gly Gly
            100                 105                 110

Thr Lys Leu Thr Val Leu Gly Gln Pro Lys Ala Ala Pro Ser Val Thr
        115                 120                 125

Leu Phe Pro Pro Ser Ser Glu Glu Leu Gln Ala Asn Lys Ala Thr Leu
    130                 135                 140

Val Cys Leu Ile Ser Asp Phe Tyr Pro Gly Ala Val Thr Val Ala Trp
145                 150                 155                 160

Lys Ala Asp Ser Ser Pro Val Lys Ala Gly Val Glu Thr Thr Thr Pro
                165                 170                 175

Ser Lys Gln Ser Asn Asn Lys Tyr Ala Ala Ser Ser Tyr Leu Ser Leu
            180                 185                 190

Thr Pro Glu Gln Trp Lys Ser His Arg Ser Tyr Ser Cys Gln Val Thr
        195                 200                 205

His Glu Gly Ser Thr Val Glu Lys Thr Val Ala Pro Thr Glu Cys Ser
    210                 215                 220

<210> SEQ ID NO 105
<211> LENGTH: 678
<212> TYPE: DNA
<213> ORGANISM: Artificial Sequence
<220> FEATURE:
<223> OTHER INFORMATION: Synthetic Polynucleotide

<400> SEQUENCE: 105

| | |
|---|---|
| cagcctgtgc tgactcagcc ggcttccctc tctgcatctc ctggagcatc agccagtctc | 60 |
| acctgcacct tgcgcagtgg catcaacgtt aaggattaca ggatattctg gtaccagcag | 120 |
| aagccaggga gtcctcccca gtatctcctg aggtacaaaa gcgaatcaga taagcagcag | 180 |
| ggctctggag tccccagccg cttctctggg tccaaagatg cttcggccaa tgcagggatt | 240 |

```
ttactcatct ctgggctcca gtctgaggat gaggctgact attactgtat gatttggcac    300
aaggatcggg aggggcatgc ttttgtgttc ggcggaggga ccaagctgac cgtcctaggt    360
cagcccaagg ctgccccctc ggtcactctg ttcccgccct cctctgagga gcttcaagcc    420
aacaaggcca cactggtgtg tctcataagt gacttctacc cgggagccgt gacagtggct    480
tggaaagcag atagcagccc cgtcaaggcg ggagtggaga ccaccacacc ctccaaacaa    540
agcaacaaca agtacgcggc cagcagctat ctgagcctga cgcctgagca gtggaagtcc    600
cacagaagct acagctgcca ggtcacgcat gaagggagca ccgtggagaa gacagtggcc    660
cctacagaat gttcataa                                                   678
```

```
<210> SEQ ID NO 106
<211> LENGTH: 225
<212> TYPE: PRT
<213> ORGANISM: Artificial Sequence
<220> FEATURE:
<223> OTHER INFORMATION: Synthetic Polypeptide

<400> SEQUENCE: 106
```

Gln Pro Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Lys Asp
                20                  25                  30

Tyr Arg Ile Phe Trp Tyr Gln Gln Lys Pro Gly Ser Pro Gln Tyr
            35                  40                  45

Leu Leu Arg Tyr Lys Ser Glu Ser Asp Lys Gln Gln Gly Ser Gly Val
        50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Lys Asp Arg Glu Gly His Ala Phe Val Phe Gly Gly
            100                 105                 110

Gly Thr Lys Leu Thr Val Leu Gly Gln Pro Lys Ala Ala Pro Ser Val
        115                 120                 125

Thr Leu Phe Pro Pro Ser Ser Glu Glu Leu Gln Ala Asn Lys Ala Thr
    130                 135                 140

Leu Val Cys Leu Ile Ser Asp Phe Tyr Pro Gly Ala Val Thr Val Ala
145                 150                 155                 160

Trp Lys Ala Asp Ser Ser Pro Val Lys Ala Gly Val Glu Thr Thr Thr
                165                 170                 175

Pro Ser Lys Gln Ser Asn Asn Lys Tyr Ala Ala Ser Ser Tyr Leu Ser
            180                 185                 190

Leu Thr Pro Glu Gln Trp Lys Ser His Arg Ser Tyr Ser Cys Gln Val
        195                 200                 205

Thr His Glu Gly Ser Thr Val Glu Lys Thr Val Ala Pro Thr Glu Cys
    210                 215                 220

Ser
225

```
<210> SEQ ID NO 107
<211> LENGTH: 678
<212> TYPE: DNA
<213> ORGANISM: Artificial Sequence
<220> FEATURE:
<223> OTHER INFORMATION: Synthetic Polynucleotide
```

<400> SEQUENCE: 107

```
cagcctgtgc tgactcagcc ggcttccctc tctgcatctc ctggggcatc agccagtctc    60
acctgcacct tgcgcagtgg catcaacgtt agagattaca ggatattctg gtaccagcag   120
aagccaggga gtcctcccca gtatctcctg aggtacaaaa gcgcatcaga taagcagcag   180
ggctctggag tccccagccg cttctctggg tccaaagatg cttcggccaa tgcagggatt   240
ttactcatct ctgggctcca gtctgaggat gaggctgact attactgtat gatttggcac   300
cacgattcgg aggggcatgc ttttgtgttc ggcggaggga ccaagctgac cgtcctaggt   360
cagcccaagg ctgccccctc ggtcactctg ttcccgccct cctctgagga gcttcaagcc   420
aacaaggcca cactggtgtg tctcataagt gacttctacc cgggagccgt gacagtggct   480
tggaaagcag atagcagccc cgtcaaggcg ggagtggaga ccaccacacc ctccaaacaa   540
agcaacaaca agtacgcggc cagcagctat ctgagcctga cgcctgagca gtggaagtcc   600
cacagaagct acagctgcca ggtcacgcat gaagggagca ccgtggagaa gacagtggcc   660
cctacagaat gttcataa                                                  678
```

<210> SEQ ID NO 108
<211> LENGTH: 225
<212> TYPE: PRT
<213> ORGANISM: Artificial Sequence
<220> FEATURE:
<223> OTHER INFORMATION: Synthetic Polypeptide

<400> SEQUENCE: 108

```
Gln Pro Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Arg Asp
            20                  25                  30

Tyr Arg Ile Phe Trp Tyr Gln Gln Lys Pro Gly Ser Pro Pro Gln Tyr
        35                  40                  45

Leu Leu Arg Tyr Lys Ser Ala Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His His Asp Ser Glu Gly His Ala Phe Val Phe Gly Gly
            100                 105                 110

Gly Thr Lys Leu Thr Val Leu Gly Gln Pro Lys Ala Ala Pro Ser Val
        115                 120                 125

Thr Leu Phe Pro Pro Ser Ser Glu Glu Leu Gln Ala Asn Lys Ala Thr
    130                 135                 140

Leu Val Cys Leu Ile Ser Asp Phe Tyr Pro Gly Ala Val Thr Val Ala
145                 150                 155                 160

Trp Lys Ala Asp Ser Ser Pro Val Lys Ala Gly Val Glu Thr Thr Thr
                165                 170                 175

Pro Ser Lys Gln Ser Asn Asn Lys Tyr Ala Ala Ser Ser Tyr Leu Ser
            180                 185                 190

Leu Thr Pro Glu Gln Trp Lys Ser His Arg Ser Tyr Ser Cys Gln Val
        195                 200                 205
```

Thr His Glu Gly Ser Thr Val Glu Lys Thr Val Ala Pro Thr Glu Cys
    210                 215                 220

Ser
225

<210> SEQ ID NO 109
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 109

| | | |
|---|---|---|
| tcctatgtgc tgactcagcc accctcagtg tcagtggccc caggaaagac ggccaggatt | 60 |
| acctgtgggg gaaacaaaat tggacaccgc gccgtgcact ggtaccagca gaagccaggc | 120 |
| caggcccctg tgctggtcat ctattatacc tatgagcggc cctcagggat cctgagcga | 180 |
| ttctctggct ccaactctgg gaacacggcc accctgacca tcagcagggt cgaagccggg | 240 |
| gatgaggccg actattactg tcaggtgtgg gattggtaca cgagggggg ggttgtgttc | 300 |
| ggcggaggga ccaagctgac cgtcctaggt cagcccaagg ctgcccctc ggtcactctg | 360 |
| ttcccgccct cctctgagga gcttcaagcc aacaaggcca cactggtgtg tctcataagt | 420 |
| gacttctacc cgggagccgt gacagtggct tggaaagcag atagcagccc cgtcaaggcg | 480 |
| ggagtggaga ccaccacacc ctccaaacaa agcaacaaca gtacgcggc agcagctat | 540 |
| ctgagcctga cgcctgagca gtggaagtcc cacagaagct acagctgcca ggtcacgcat | 600 |
| gaagggagca ccgtggagaa gacagtggcc cctacagaat gttcataa | 648 |

<210> SEQ ID NO 110
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 110

Ser Tyr Val Leu Thr Gln Pro Pro Ser Val Ser Val Ala Pro Gly Lys
1               5                   10                  15

Thr Ala Arg Ile Thr Cys Gly Gly Asn Lys Ile Gly His Arg Ala Val
            20                  25                  30

His Trp Tyr Gln Gln Lys Pro Gly Gln Ala Pro Val Leu Val Ile Tyr
        35                  40                  45

Tyr Thr Tyr Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Trp Tyr Ser Glu Gly
                85                  90                  95

Gly Val Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

```
Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 111
<211> LENGTH: 651
<212> TYPE: DNA
<213> ORGANISM: Artificial Sequence
<220> FEATURE:
<223> OTHER INFORMATION: Synthetic Polynucleotide

<400> SEQUENCE: 111
cagtctgtgt tgacgcagcc gccctcagtg tctgcggccc caggacagaa ggtcaccatc      60
tcctgctctg gaagcagctc caatattgag actggttctg tatcctggta ccagcagctc     120
ccaggaacag cccccaaact cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggatg acagcctgcc tggatgggtg     300
ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcttggaaag cagatagcag ccccgtcaag     480
gcgggagtgg agaccaccac accctccaaa caaagcaaca caagtacgc ggccagcagc     540 tatctgagcc tgacgcctga gcagtggaag tcccacagaa gctacagctg ccaggtcacg     600
catgaaggga gcaccgtgga aagacagtg gcccctacag aatgttcata a              651

<210> SEQ ID NO 112
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 112

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Thr Gly
            20                  25                  30

Ser Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asp Ser Leu
                85                  90                  95

Pro Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125
```

```
Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 113
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 113
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg gctggagtg gtctcagct attagtggta gtggtggtag cacatactac        180
gcagactccg tgaagggccg gttcaccatc tccagagaca attccaagaa cacgctgtat       240
ctgcaaatga acagcctgag agccgaggac acggccgtat attactgtgc gaaaagttat       300
ggtgcttttg actactgggg ccagggaacc ctggtcacag tctcgagc                   348

<210> SEQ ID NO 114
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
                100                 105                 110

Thr Val Ser Ser
        115

<210> SEQ ID NO 115
<211> LENGTH: 324
<212> TYPE: DNA
<213> ORGANISM: Artificial Sequence
```

```
<220> FEATURE:
<223> OTHER INFORMATION: Synthetic Polynucleotide

<400> SEQUENCE: 115
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg aagtggatc tgggacagat tttactttca ccatcagcag cctgcagcct     240
gaagatattg caacatatta ctgtcagcag aagcacccc ggggggccgag gaccttcggc     300 caagggacca aggtggaaat caaa                                            324

<210> SEQ ID NO 116
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 116

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Lys Tyr
                20                  25                  30

Leu Asn Trp Tyr Gln Gln Lys Pro Gly Lys Ala Pro Lys Leu Leu Ile
             35                  40                  45

Tyr Gly Ala Ser Arg Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Lys His Pro Arg Gly Pro
                 85                  90                  95

Arg Thr Phe Gly Gln Gly Thr Lys Val Glu Ile Lys
            100                 105

<210> SEQ ID NO 117
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 117
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg aagtggatc tgggacagat tttactttca ccatcagcag cctgcagcct     240
gaagatattg caacatatta ctgtcagcag aagcacccc ggaacccgag gaccttcggc     300
caagggacca aggtggaaat caaa                                            324

<210> SEQ ID NO 118
<211> LENGTH: 108
<212> TYPE: PRT
<213> ORGANISM: Artificial Sequence
<220> FEATURE:
<223> OTHER INFORMATION: Synthetic Polypeptide
```

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Asn Pro
                85                  90                  95

Arg Thr Phe Gly Gln Gly Thr Lys Val Glu Ile Lys
            100                 105

<210> SEQ ID NO 119
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 119
gacatccaga tgacccagtc tccatcctcc ctgtctgcat ctgtaggaga cagagtcacc      60
atcacttgcc aggcgagtca gtccattagt agttatttaa attggtatca gcagaaacca     120
gggaaagccc ctaagctcct gatctacgct gcatcctcgt tggaaacagg ggtcccatca     180
aggttcagtg gaagtggatc tgggacagat tttactttca ccatcagcag cctgcagcct     240
gaagatattg caacatatta ctgtcagcag aagcaccccc gggggccgag gaccttcggc     300
caagggacca aggtggaaat caaa                                            324

<210> SEQ ID NO 120
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 121
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 121

```
gacatccaga tgacccagtc tccatcctcc ctgtctgcat ctgtaggaga cagagtcacc    60
atcacttgcc aggcgagtca ggacattaat aagtatttaa attggtatca gcagaaacca   120
gggaaagccc ctaagctcct gatctacggt gcatccaggt tggaaacagg ggtcccatca   180
aggttcagtg gaagtggatc tgggacagat tttactttca ccatcagcag cctgcagcct   240
gaagatattg caacatatta ctgtcagcag aagcaccccc ggtacccgag gaccttcggc   300
caagggacca aggtggaaat caaa                                          324
```

<210> SEQ ID NO 122
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Tyr Pro
                85                  90                  95

Arg Thr Phe Gly Gln Gly Thr Lys Val Glu Ile Lys
            100                 105

<210> SEQ ID NO 123
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 123

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag ttccacaagc ggcggccgca gaccttcggc   300
caagggacca aggtggaaat caaa                                          324
```

<210> SEQ ID NO 124
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys
            100                 105

<210> SEQ ID NO 125
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 125
gacatccaga tgacccagtc tccatcctcc ctgtctgcat ctgtaggaga cagagtcacc      60
atcacttgcc gggcaagtca gagcattgcg aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag ttccataagc gtgcgccgca gaccttcggc    300
caagggacca aggtggaaat caaa                                            324

<210> SEQ ID NO 126
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ala Pro
                85                  90                  95

Gln Thr Phe Gly Gln Gly Thr Lys Val Glu Ile Lys
            100                 105

<210> SEQ ID NO 127
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 127

```
gacatccaga tgacccagtc tccatcctcc ctgtctgcat ctgtaggaga cagagtcacc    60
atcacttgcc gggcaagtca gagcattggt aagtatttaa attggtatca gcagaaacca   120
gggaaagccc ctaagctcct gatctatgcg gcatccaggt tgcaaagtgg ggtcccatca   180
aggttcagtg gcagtggatc tgggacagat ttcactctca ccatcagcag tctgcaacct   240
gaagattttg caacttacta ctgtcagcag aagcacccgc gtgccccgcg gaccttcggc   300
caagggacca aggtggaaat caaa                                          324
```

<210> SEQ ID NO 128
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys
            100                 105

<210> SEQ ID NO 129
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 129

```
gacatccaga tgacccagtc tccatcctcc ctgtctgcat ctgtaggaga cagagtcacc    60
atcacttgcc gggcaagtca gagcattgat aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatcccc gtgggccgag gaccttcggc   300
caagggacca aggtggaaat caaa                                          324
```

<210> SEQ ID NO 130
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 131
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 131
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag aagcatcccc gtggcccgcg gaccttcggc     300
caagggacca aggtggaaat caaa                                            324

<210> SEQ ID NO 132
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 133
<211> LENGTH: 324
<212> TYPE: DNA
<213> ORGANISM: Artificial Sequence
<220> FEATURE:
<223> OTHER INFORMATION: Synthetic Polypeptide

<400> SEQUENCE: 133

```
gacatccaga tgacccagtc tccatcctcc ctgtctgcat ctgtaggaga cagagtcacc      60
atcacttgcc gggcaagtca gagcattaat aggtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag aagcatccgc gtgggccgag gaccttcggc     300
caagggacca aggtggaaat caaa                                            324
```

<210> SEQ ID NO 134
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 135
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 135

```
gacatccaga tgacccagtc tccatcctcc ctgtctgcat ctgtaggaga cagagtcacc      60
atcacttgcc gggcaagtca gagcattggt aggtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgcgccgaa gaccttcggc     300
caagggacca aggtggaaat caaa                                            324
```

<210> SEQ ID NO 136
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 137
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 137
gacatccaga tgacccagtc tccatcctcc ctgtctgcat ctgtaggaga cagagtcacc     60
atcacttgcc gggtaagtca gagcattagt aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag aggcatcccc gtgggccgag caccttcggc    300
caagggacca aggtggaaat caaa                                           324

<210> SEQ ID NO 138
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Val Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Ser Thr Phe Gly Gln Gly Thr Lys Val Glu Ile Lys
            100                 105

<210> SEQ ID NO 139
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 139

```
gacatccaga tgacccagtc tccatcctcc ctgtctgcat ctgtaggaga cagagtcacc    60
atcacttgcc aggcgagtca ggacattaat aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aggcatccgc gtgccccgcg gaccttcggc   300
caagggacca aggtggaaat caaa                                          324
```

<210> SEQ ID NO 140
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Ala Pro
                85                  90                  95

Arg Thr Phe Gly Gln Gly Thr Lys Val Glu Ile Lys
            100                 105

<210> SEQ ID NO 141
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 141

```
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctatgct gcatccactt tgcaaagtgg ggtcccatca   180
aggttcagtg gcagtggatc tgggacagat ttcactctca ccatcagcag tctgcaacct   240
gaagattttg caacttacta ctgtcagcag atgcatccgc gtgcgccgaa gaccttcggc   300
caagggacca aggtggaaat caaa                                          324
```

<210> SEQ ID NO 142
<211> LENGTH: 108
<212> TYPE: PRT
<213> ORGANISM: Artificial Sequence

```
<220> FEATURE:
<223> OTHER INFORMATION: Synthetic Polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 143
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 143
gacatccaga tgacccagtc tccatcctcc ctgtctgcat ctgtaggaga cagagtcacc      60
atcacttgcc aggcgagtca ggacattaat aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag cgccatccgc gtggcccgag gaccttcggc    300
caagggacca aggtggaaat caaa                                            324

<210> SEQ ID NO 144
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Arg Thr Phe Gly Gln Gly Thr Lys Val Glu Ile Lys
            100                 105
```

<210> SEQ ID NO 145
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 145

```
gacatccaga tgacccagtc tccatcctcc ctgtctgcat ctgtaggaga cagagtcacc      60
atcacttgcc gggcaagtca gagcattggt aggtatttaa attggtatca gcagaaacca     120
gggaaagccc ctaagctcct gatctatgcg gcatccaggt tgcaaagtgg ggtcccatca     180
aggttcagtg gcagtggatc tgggacagat ttcactctca ccatcaacag tctgcaacct     240
gaagattttg caacttacta ctgtcagcag aagcatcccc gtgcgccgag gaccttcggc     300
caagggacca aggtggaaat caaa                                            324
```

<210> SEQ ID NO 146
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 146

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys
            100                 105

<210> SEQ ID NO 147
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 147

```
gacatccaga tgacccagtc tccatcctcc ctgtctgcat ctgtaggaga cagagtcacc      60
atcacttgcc gggcaagtca gagcattgat aagtatttaa attggtatca gcagaaacca     120
gggaaagccc ctaagctcct gatctatgcg gcatccaggt tgcaaagtgg ggtcccatca     180
aggttcagtg gcagtggatc tgggacagat ttcactctca ccatcagcag tctgcaacct     240
gaagattttg caacttacta ctgtcagcag cggcataagc gttccccgca gaccttcggc     300
caagggacca aggtggaaat caaa                                            324
```

<210> SEQ ID NO 148
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Lys Arg Ser Pro
                85                  90                  95

Gln Thr Phe Gly Gln Gly Thr Lys Val Glu Ile Lys
            100                 105

<210> SEQ ID NO 149
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 149
gacatccaga tgacccagtc tccatcctcc ctgtctgcat ctgtaggaga cagagtcacc        60
atcacttgcc gggcaagtca gagcattgat aagtatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatcagcag tctgcaacct       240
gaagattttg caacttacta ctgtcagcag aagcatccgc gtgcgccgcg gaccttcggc       300
caagggacca aggtggaaat caaa                                              324

<210> SEQ ID NO 150
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys
            100                 105

<210> SEQ ID NO 151
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 151

```
gacatccaga tgacccagtc tccatcctcc ctgtctgcat ctgtaggaga cagagtcacc      60
atcacttgcc gggcaagtca gagcattggg aagtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtagcccgaa gaccttcggc     300
caagggacca aggtggaaat caaa                                             324
```

<210> SEQ ID NO 152
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys
            100                 105

<210> SEQ ID NO 153
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 153

```
gacatccaga tgacccagtc tccatcctcc ctgtctgcat ctgtaggaga cagagtcacc      60
atcacttgcc gggcaagtca gagcattagt aggtatttaa attggtatca gcagaaacca     120
gggaaagccc ctaagctcct gatctatgct gcatccaatt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgggccgaa gaccttcggc     300
caagggacca aggtggaaat caaa                                             324
```

<210> SEQ ID NO 154
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys
            100                 105

<210> SEQ ID NO 155
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 155
gacatccaga tgacccagtc tccatcctcc ctgtctgcat ctgtaggaga cagagtcacc      60
atcacttgcc gggcaagtca gagcattgct tcttatgtaa attggtatca gcagaaacca     120
gggaaagccc ctaagctcct gatctatgct gcatccggtt tgcaaagtgg ggtcccatca     180
aggttcagtg gcagtggatc tgggacagat ttcactctca ccatcagcag tctgcaacct     240
gaagattttg caacttacta ctgtcagcag ttccataagc gtcggccgca gaccttcggc     300
caagggacca aggtggaaat caaa                                            324

<210> SEQ ID NO 156
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Val Asn Trp Tyr Gln Gln Lys Pro Gly Lys Ala Pro Lys Leu Leu Ile
        35                  40                  45

Tyr Ala Ala Ser Gly Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys
            100                 105

```
<210> SEQ ID NO 157
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 157
gacatccaga tgacccagtc tccatcctcc ctgtctgcat ctgtaggaga cagagtcacc    60
atcacttgcc gggcaagtca gagcattggg aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag atgcatccgc gtgggccgaa gaccttcggc   300
caagggacca aggtggaaat caaa                                          324

<210> SEQ ID NO 158
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys
            100                 105

<210> SEQ ID NO 159
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 159
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctataat gcatccactt tgcaaagtgg ggtcccatca   180
aggttcagtg gcagtggatc tgggacagat ttcactctca ccatcagcag tctgcaacct   240
gaagattttg caacttacta ctgtcagcag aggcatccgc gtgggccgcg caccttcggc   300
caagggacca aggtggaaat caaa                                          324

<210> SEQ ID NO 160
<211> LENGTH: 108
<212> TYPE: PRT
<213> ORGANISM: Artificial Sequence
```

<220> FEATURE:
<223> OTHER INFORMATION: Synthetic Polypeptide

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Arg Thr Phe Gly Gln Gly Thr Lys Val Glu Ile Lys
            100                 105

<210> SEQ ID NO 161
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 161
gacatccaga tgacccagtc tccatcctcc ctgtctgcat ctgtaggaga cagagtcacc      60
atcacttgcc gggcaagtca gagcattagt aagtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag aagcatccgc gtagcccgcg gaccttcggc     300
caagggacca aggtggaaat caaa                                            324

<210> SEQ ID NO 162
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ser Pro
                85                  90                  95

Arg Thr Phe Gly Gln Gly Thr Lys Val Glu Ile Lys
            100                 105

<210> SEQ ID NO 163
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 163
gacatccaga tgacccagtc tccatcctcc ctgtctgcat ctgtaggaga cagagtcacc    60
atcacttgcc gggcaagtca gagcattgct aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag ttccataagc gtagcccgca gaccttcggc   300
caagggacca aggtggaaat caaa                                          324

<210> SEQ ID NO 164
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ser Pro
                85                  90                  95

Gln Thr Phe Gly Gln Gly Thr Lys Val Glu Ile Lys
            100                 105

<210> SEQ ID NO 165
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 165
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctataat gcatccaatt tgcaaagtgg ggtcccatca   180
aggttcagtg gcagtggatc tgggacagat ttcactctca ccatcagcag tctgcaacct   240
gaagattttg caacttacta ctgtcagcag aggcatccgc gtgggccgac caccttcggc    300
caagggacca aggtggaaat caaa    324

<210> SEQ ID NO 166
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Thr Thr Phe Gly Gln Gly Thr Lys Val Glu Ile Lys
            100                 105

<210> SEQ ID NO 167
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 167
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcacccgc gcgccccgaa gaccttcggc    300
caagggacca aggtggaaat caaa    324

<210> SEQ ID NO 168
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys
            100                 105
```

<210> SEQ ID NO 169
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 169

```
gacatccaga tgacccagtc tccatcctcc ctgtctgcat ctgtaggaga cagagtcacc      60
atcacttgcc gggcaagtca gagcattagt aagtattta  attggtatca gcagaaacca    120
gggaaagccc ctaagctcct gatctatgct gcatccaggt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gctcgccgaa aaccttcggc    300
caagggacca aggtggaaat caaa                                            324
```

<210> SEQ ID NO 170
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 170

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Lys Tyr
                20                  25                  30

Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ser Pro
                 85                  90                  95

Lys Thr Phe Gly Gln Gly Thr Lys Val Glu Ile Lys
            100                 105
```

<210> SEQ ID NO 171
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 171

```
gacatccaga tgacccagtc tccatcctcc ctgtctgcat ctgtaggaga cagagtcacc      60
atcacttgcc aggcgagtca ggacattgct aagtattta  attggtatca gcagaaacca    120
gggaaagccc ctaagctcct gatctatgct gcatccgctt tgcaaagtgg ggtcccatca    180
aggttcagtg gcagtggatc tgggacagat ttcactctca ccatcagcag tctgcaacct    240
```

-continued

```
gaagatttg caacttacta ctgtcagcag atgcatcctc gctcgccgaa aaccttcggc    300
caagggacca aggtggaaat caaa                                          324
```

<210> SEQ ID NO 172
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 172

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys
            100                 105
```

<210> SEQ ID NO 173
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 173

```
gacatccaga tgacccagtc tccatcctcc ctgtctgcat ctgtaggaga cagagtcacc     60
atcacttgcc gggcaagtca gagcattgct agttatttaa attggtatca gcagaaacca    120
gggaaagccc ctaagctcct gatctatgcg gcatccaggt tgcaaagtgg ggtcccatca    180
aggttcagtg gcagtggatc tgggacagat ttcactctca ccatcagcag tctgcaacct    240 gaagatttg caacttacta ctgtcagcag atgcatcctc gcgcgccgaa aaccttcggc     300
caagggacca aggtggaaat caaa                                           324
```

<210> SEQ ID NO 174
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 174

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys
            100                 105
```

<210> SEQ ID NO 175
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 175

```
gacatccaga tgacccagtc tccatcctcc ctgtctgcat ctgtaggaga cagagtcacc    60
atcacttgcc gggcaagtca gagcattgcg agttatttaa attggtatca gcagaaacca   120
gggaaagccc ctaagctcct gatctatgcg catccaggt tgcaaagtgg ggtcccatca    180
aggttcagtg gcagtggatc tgggacagat ttcactctca ccatcagcag tctgcaacct   240
gaagattttg caacttacta ctgtcagcag atgcatcctc gctcgccgaa aaccttcggc   300
caagggacca aggtggaaat caaa                                          324
```

<210> SEQ ID NO 176
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 176

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ala Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Arg Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ser Pro
                 85                  90                  95

Lys Thr Phe Gly Gln Gly Thr Lys Val Glu Ile Lys
            100                 105
```

<210> SEQ ID NO 177
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 177

```
gacatccaga tgacccagtc tccatcctcc ctgtctgcat ctgtaggaga cagagtcacc    60
atcacttgcc gggcaagtca gaacattggt aagtatttaa attggtatca gcagaaacca   120
gggaaagccc ctaagctcct gatctatagt gcatccaggt tgcaaagtgg ggtcccatca   180
aggttcagtg gcagtggatc tgggacagat ttcactctca ccatcagcag tctgcaacct   240
```

```
gaagattttg caacttacta ctgtcagcag atgcatcctc gcgcgccgaa aaccttcggc      300
caagggacca aggtggaaat caaa                                             324
```

<210> SEQ ID NO 178
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Lys Tyr
            20                  25                  30

Leu Asn Trp Tyr Gln Gln Lys Pro Gly Lys Ala Pro Lys Leu Leu Ile
        35                  40                  45

Tyr Ser Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

<210> SEQ ID NO 179
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 179

```
gacatccaga tgacccagtc tccatcctcc ctgtctgcat ctgtaggaga cagagtcacc       60
atcacttgcc gggcaagtca gagcattagt aggtatttaa attggtatca gcagaaacca      120
gggaaagccc ctaagctcct gatctattct gcatcctctt tgcaaagtgg ggtcccatca      180
aggttcagtg gcagtggatc tgggacagat ttcactctca ccatcagcag tctgcaacct      240
gaagattttg caacttacta ctgtcagcag atgcatcctc gcgccccgaa aaccttcggc      300
caagggacca aggtggaaat caaa                                             324
```

<210> SEQ ID NO 180
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 180

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 181
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 181
gacatccaga tgacccagtc tccatcctcc ctgtctgcat ctgtaggaga cagagtcacc     60
atcacttgcc gggcaagtca gagcattgat aagtatttaa attggtatca gcagaaacca    120
gggaaagccc ctaagctcct gatctatgct gcatccaggt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgggccgaa aaccttcggc    300
caagggacca aggtggaaat caaa                                           324

<210> SEQ ID NO 182
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys
            100                 105

<210> SEQ ID NO 183
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 183
gacatccaga tgacccagtc tccatcctcc ctgtctgcat ctgtaggaga cagagtcacc     60
atcacttgcc gggcaagtca gagcattggt aagtatttaa attggtatca gcagaaacca    120
gggaaagccc ctaagctcct gatctatgct gcatccaggt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgcgccgaa aaccttcggc    300
caagggacca aggtggaaat caaa    324

<210> SEQ ID NO 184
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 185
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 185
cagtctgccc tgactcagcc tgcctccgtg tctgggtctc ctggacagtc gatcaccatc     60
tcctgcactg gaaccagcag tgacgttggt ggttataact atgtctcctg gtaccaacag    120
cacccaggca aagcccccaa actcatgatt tatgaggtca gtaatcggcc ctcaggggtt    180
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg gagggaccaa gctgaccgtc cta                                 333

<210> SEQ ID NO 186
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 186

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
            100                 105                 110

<210> SEQ ID NO 187
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 187
cagtctgccc tgactcagcc tgcctccgtg tctgggtctc ctggacagtc gatcaccatc      60
tcctgcactg gaaccagcag tgacgttggg aaggcgaact atgtctcctg gtaccaacag     120
cacccaggca aagcccccaa actcatgatt tataaggata gtgatcggcc ctcagggggtt    180 tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc cta                                  333

<210> SEQ ID NO 188
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 188

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Lys Ala
                20                  25                  30

Asn Tyr Val Ser Trp Tyr Gln Gln His Pro Gly Lys Ala Pro Lys Leu
             35                  40                  45

Met Ile Tyr Lys Asp Ser Asp Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
            100                 105                 110

<210> SEQ ID NO 189
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 189
cagtctgccc tgactcagcc tgcctccgtg tctgggtctc ctggacagtc gatcaccatc      60
tcctgcactg gaaccagcag tgacgttagg gggaataact atgtctcctg gtaccaacag     120
cacccaggca aagcccccaa actcatgatt tatgagaata gtaagcggcc ctcagggggtt    180 tctaatcgct tctctggctc caagtctggc aacacggcct ccctgaccat ctctgggctc     240
```

```
caggctgagg acgaggctga ttattactgc agctcatatg attggtggtt ccgccccaag    300
gtgttcggcg gagggaccaa gctgaccgtc cta                                 333
```

<210> SEQ ID NO 190
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 190

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Gly Asn
                20                  25                  30

Asn Tyr Val Ser Trp Tyr Gln Gln His Pro Gly Lys Ala Pro Lys Leu
            35                  40                  45

Met Ile Tyr Glu Asn Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110
```

<210> SEQ ID NO 191
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 191

```
cagtctgccc tgactcagcc tgcctccgtg tctgggtctc ctggacagtc gatcaccatc     60
tcctgcactg gaaccagcag tgacgttagt gcgaggaact atgtctcctg gtaccaacag    120
cacccaggca aagcccccaa actcatgatt tatgagagta gtaagcggcc ctcaggggtt    180
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg gagggaccaa gctgaccgtc cta                                 333
```

<210> SEQ ID NO 192
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 192

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Ser Ala Arg
                20                  25                  30

Asn Tyr Val Ser Trp Tyr Gln Gln His Pro Gly Lys Ala Pro Lys Leu
            35                  40                  45

Met Ile Tyr Glu Ser Ser Lys Arg Pro Ser Gly Val Ser Asn Arg Phe
        50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110

<210> SEQ ID NO 193
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 193
cagtctgccc tgactcagcc tgcctccgtg tctgggtctc ctggacagtc gatcaccatc     60
tcctgcacta gaaccagcag tgacgttaat aatactaact atgtctcctg gtaccaacag    120
cacccaggca aagcccccaa actcatgatt tataagacta gtggtcggcc ctcaggggtt    180
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg gagggaccaa gctgaccgtc cta                                 333

<210> SEQ ID NO 194
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 194

Gln Ser Ala Leu Thr Gln Pro Ala Ser Val Ser Gly Ser Pro Gly Gln
1               5                   10                  15

Ser Ile Thr Ile Ser Cys Thr Arg Thr Ser Ser Asp Val Asn Asn Thr
                20                  25                  30

Asn Tyr Val Ser Trp Tyr Gln Gln His Pro Gly Lys Ala Pro Lys Leu
            35                  40                  45

Met Ile Tyr Lys Thr Ser Gly Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110

<210> SEQ ID NO 195
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 195
cagtctgccc tgactcagcc tgcctccgtg tctgggtctc ctggacagtc gatcaccatc     60
tcctgcactg gaaccagcag tgacgttaat tctgctaact atgtctcctg gtaccaacag    120
cacccaggca aagcccccaa actcatgatt tataagagta gtagtcggcc ctcaggggtt    180
tctaatcgct tctctggctc caagtctggc aacacggcct ccctgaccat ctctgggctc    240

```
caggctgagg acgaggctga ttattactgc agctcatatg attggtggtt ccgccccaag    300
gtgttcggcg agggaccaa gctgaccgtc cta                                  333
```

<210> SEQ ID NO 196
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 196

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Asn Ser Ala
            20                  25                  30

Asn Tyr Val Ser Trp Tyr Gln Gln His Pro Gly Lys Ala Pro Lys Leu
        35                  40                  45

Met Ile Tyr Lys Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110
```

<210> SEQ ID NO 197
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 197

```
cagtctgccc tgactcagcc tgcctccgtg tccgggtctc ctggacagtc gatcaccatc     60
tcctgcactg gaaccagcag tgacgttgag aggaagaact atgtctcctg gtaccaacag    120
cacccaggca aagcccccaa actcatgatt tataagaata gtactcggcc ctcagggttt    180
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg agggaccaa gctgaccgtc cta                                  333
```

<210> SEQ ID NO 198
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 198

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Glu Arg Lys
            20                  25                  30

Asn Tyr Val Ser Trp Tyr Gln Gln His Pro Gly Lys Ala Pro Lys Leu
        35                  40                  45

Met Ile Tyr Lys Asn Ser Thr Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
            100                 105                 110

<210> SEQ ID NO 199
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 199
cagtctgccc tgactcagcc tgcctccgtg tctgggtctc ctggacagtc gatcaccatc      60
tcctgcactg gaaccagcag tgacgttagg cggctaact atgtctcctg gtaccaacag      120
cacccaggca aagcccccaa actcatgatt tataagaata gtactcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag    300
gtgttcggcg gagggaccaa gctgaccgtc cta                                   333

<210> SEQ ID NO 200
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 200

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Arg Ala Ala
                 20                  25                  30

Asn Tyr Val Ser Trp Tyr Gln Gln His Pro Gly Lys Ala Pro Lys Leu
             35                  40                  45

Met Ile Tyr Lys Asn Ser Thr Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
            100                 105                 110

<210> SEQ ID NO 201
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 201
cagtctgccc tgactcagcc tgcctccgtg tctgggtctc ctggacagtc gatcaccatc      60
tcctgcactg gaaccagcag tgacgttagg agggctaact atgtctcctg gtaccaacag     120
cacccaggca aagcccccaa actcatgatt tatcaggata gtagtcggcc ctcaggggtt    180
tctaatcgct tctctggctc caagtctggc aacacggcct ccctgaccat ctctgggctc     240
```

```
caggctgagg acgaggctga ttattactgc agctcatatg attggtggtt ccgccccaag    300
gtgttcggcg agggaccaa gctgaccgtc cta                                  333
```

<210> SEQ ID NO 202
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 202

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Arg Ala
            20                  25                  30

Asn Tyr Val Ser Trp Tyr Gln Gln His Pro Gly Lys Ala Pro Lys Leu
        35                  40                  45

Met Ile Tyr Gln Asp Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110
```

<210> SEQ ID NO 203
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 203

```
cagtctgccc tgactcagcc tgcctccgtg tctgggtctc ctggacagtc gatcaccatc     60
tcctgcactg gaaccagcag tgacgttagg gctaataact atgtctcctg gtaccaacag    120
cacccaggca aagcccccaa actcatgatt tatgagagta gtgcgcggcc ctcaggggtt    180
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg agggaccaa gctgaccgtc cta                                  333
```

<210> SEQ ID NO 204
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 204

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Ala Asn
            20                  25                  30

Asn Tyr Val Ser Trp Tyr Gln Gln His Pro Gly Lys Ala Pro Lys Leu
        35                  40                  45

Met Ile Tyr Glu Ser Ser Ala Arg Pro Ser Gly Val Ser Asn Arg Phe
    50                  55                  60
```

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
            100                 105                 110

<210> SEQ ID NO 205
<211> LENGTH: 330
<212> TYPE: DNA
<213> ORGANISM: Artificial Sequence
<220> FEATURE:
<223> OTHER INFORMATION: Synthetic Polynucleotide

<400> SEQUENCE: 205
cagtctgtgt tgacgcagcc gccctcagtg tctgcggccc caggacagaa ggtcaccatc      60
tcctgctctg gaagcagctc caatattgag actggttctg tatcctggta ccagcagctc     120
ccaggaacag cccccaaact cctcatttat gacaataata gcgaccctca gggattcct     180 gaccgattct ctggctccaa gtctggcacg tcagccaccc tgggcatcac cggactccag     240 actgggacg aggccgatta ttactgcgga acatgggatg acagcctgcc tggatgggtg     300
ttcggcggag ggaccaagct gaccgtccta                                     330

<210> SEQ ID NO 206
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 206

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Glu Thr Gly
             20                  25                  30

Ser Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Asp Ser Leu
                 85                  90                  95

Pro Gly Trp Val Phe Gly Gly Gly Thr Lys Leu Thr Val Leu
            100                 105                 110

<210> SEQ ID NO 207
<211> LENGTH: 657
<212> TYPE: DNA
<213> ORGANISM: Artificial Sequence
<220> FEATURE:
<223> OTHER INFORMATION: Synthetic Polynucleotide

<400> SEQUENCE: 207
gaaatagtga tgacgcagtc tccagccacc ctgtctgtgt ctccagggga agagccacc      60 ctctcctgca gggccagtca gacggttaag aataatttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240

```
gaagattttg cagtttatta ctgtcagcag tataacaact ggttgcccat caacccctat    300
accttcggcc aagggaccaa ggtggaaatc aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagctc gcccgtcaca aagagcttca caggggaga gtgttaa       657
```

<210> SEQ ID NO 208
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 208

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Lys Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Leu Pro
                85                  90                  95

Ile Asn Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 209
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 209

```
gaaatagtga tgacgcagtc tccagccacc ctgtctgtgt ctccagggga aagagccacc     60
ctctcctgca gggccagtca gacggttaag aataatttag cctggtacca gcagaaacct    120
```

```
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataacaact ggttgcccat caaccctat     300 accttcggcc aagggaccaa ggtggaaatc aaa                                 333
```

<210> SEQ ID NO 210
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 210

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Lys Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Leu Pro
                85                  90                  95

Ile Asn Pro Tyr Thr Phe Gly Gln Gly Thr Lys Val Glu Ile Lys
            100                 105                 110
```

<210> SEQ ID NO 211
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 211

```
cagcctgtgc tgactcagcc ggcttccctc tctgcatctc ctggagcatc agccagtctc     60
acctgcacct tgcacagtgg catctctgtt aaggattaca ggatatactg gtaccagcag    120
aagccagggc gtcctcccca gtatctcctg aggtacaagt ctaattcaga tatgcagcag    180
ggatctggag tccccagccg cttctctggg tccaaagatg cttcggccaa tgcagggatt    240
ttactcatct ctgggctcca gtctgaggat gaggctgact attactgtat gatttggcac    300
catggccatg ggactagtct tgtgttcggc ggagggacca gctgaccgt ccta           354
```

<210> SEQ ID NO 212
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 212

```
Gln Pro Val Leu Thr Gln Pro Ala Ser Leu Ser Ala Ser Pro Gly Ala
1               5                   10                  15

Ser Ala Ser Leu Thr Cys Thr Leu His Ser Gly Ile Ser Val Lys Asp
            20                  25                  30

Tyr Arg Ile Tyr Trp Tyr Gln Gln Lys Pro Gly Arg Pro Pro Gln Tyr
        35                  40                  45
```

Leu Leu Arg Tyr Lys Ser Asn Ser Asp Met Gln Gln Gly Ser Gly Val
        50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                85                  90                  95

Met Ile Trp His His Gly His Gly Thr Ser Leu Val Phe Gly Gly Gly
            100                 105                 110

Thr Lys Leu Thr Val Leu
        115

<210> SEQ ID NO 213
<211> LENGTH: 369
<212> TYPE: DNA
<213> ORGANISM: Artificial Sequence
<220> FEATURE:
<223> OTHER INFORMATION: Synthetic Polynucleotide

<400> SEQUENCE: 213
cagtctgtgc tgactcagcc accctcagcg tctgggaccc ccgggcagag ggtcaccatc    60
tcttgttctg gaagcagctc caacatcgcg catgggcctg taaactggta ccagcagctc   120
ccaggaacgg cccccaaact cctcatctat gctactaatc atcggccctc aggggtccct   180
gaccgatttt ctggctccaa gtctggcacc acagcctccc tgaccatcag tgggctccag   240
tctgaggatg aggctgatta ttactgtgct gcatatgatc ttacgggctg gtttgcgtat   300
gctgtgttcg gcggagggac caagctgacc gtcctaggtc agcccaaggc tgccccctcg   360
gtcactctg                                                          369

<210> SEQ ID NO 214
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 214

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Ala His Gly
             20                  25                  30

Pro Val Asn Trp Tyr Gln Gln Leu Pro Gly Thr Ala Pro Lys Leu Leu
         35                  40                  45

Ile Tyr Ala Thr Asn His Arg Pro Ser Gly Val Pro Asp Arg Phe Ser
 50                  55                  60

Gly Ser Lys Ser Gly Thr Thr Ala Ser Leu Thr Ile Ser Gly Leu Gln
 65                  70                  75                  80

Ser Glu Asp Glu Ala Asp Tyr Tyr Cys Ala Ala Tyr Asp Leu Thr Gly
                85                  90                  95

Trp Phe Ala Tyr Ala Val Phe Gly Gly Gly Thr Lys Leu Thr Val Leu
            100                 105                 110

Gly Gln Pro Lys Ala Ala Pro Ser Val Thr Leu
        115                 120

<210> SEQ ID NO 215
<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 215

| | | |
|---|---|---|
| tcctatgtgc tgactcagcc accctcagtg tcagtggccc aggaaagac ggccaggatt | 60 |
| acctgtgggg gaaacaagat tggacaccgc gccgtgcact ggtaccagca gaagccaggc | 120 |
| caggcccctg tgctggtcat ctattatacc tatgatcggc cctcaggat tcctgagcga | 180 |
| ttctctggct ccaactctgg gaacacggcc accctgacca tcagcagggt cgaagccggg | 240 |
| gatgaggccg actattactg tcaggtgtgg gatgcgtcta ggcgcgacgc gaatgttgtg | 300 |
| ttcggcggag ggaccaagct gaccgtccta ggtcagccca aggctgcccc ctcggtcact | 360 |
| ctg | 363 |

<210> SEQ ID NO 216
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 216

Ser Tyr Val Leu Thr Gln Pro Pro Ser Val Ser Val Ala Pro Gly Lys
1               5                   10                  15

Thr Ala Arg Ile Thr Cys Gly Gly Asn Lys Ile Gly His Arg Ala Val
            20                  25                  30

His Trp Tyr Gln Gln Lys Pro Gly Gln Ala Pro Val Leu Val Ile Tyr
        35                  40                  45

Tyr Thr Tyr Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ala Ser Arg Arg Asp
                85                  90                  95

Ala Asn Val Val Phe Gly Gly Gly Thr Lys Leu Thr Val Leu Gly Gln
            100                 105                 110

Pro Lys Ala Ala Pro Ser Val Thr Leu
        115                 120

<210> SEQ ID NO 217
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 217

| | | |
|---|---|---|
| cagcctgtgc tgactcagcc ggtttccctc tctgcatctc ctggagcatc agtcagtctc | 60 |
| acctgcacct tgcgcagtga catcagggtt agagattaca ggatattctg gtaccagcag | 120 |
| aagccaggga gtcctcccca gtatctcctg aggtacaaaa ccgactcaga taagcagcag | 180 |
| ggctctggag tccccagccg cttctctggg tccaaagatg cttcggccaa tgcagggatt | 240 |
| ttactcatct ctgggctcca gtctgaggat gaggctgact attactgtat gatttggcac | 300 |
| cgcaccacgg gcactagtct tgtgttcggc ggagggacca agctgaccgt ccta | 354 |

-continued

<210> SEQ ID NO 218
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 218

```
Gln Pro Val Leu Thr Gln Pro Val Ser Leu Ser Ala Ser Pro Gly Ala
1               5                   10                  15

Ser Val Ser Leu Thr Cys Thr Leu Arg Ser Asp Ile Arg Val Arg Asp
            20                  25                  30

Tyr Arg Ile Phe Trp Tyr Gln Gln Lys Pro Gly Ser Pro Pro Gln Tyr
        35                  40                  45

Leu Leu Arg Tyr Lys Thr Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Arg Thr Thr Gly Thr Ser Leu Val Phe Gly Gly Gly
            100                 105                 110

Thr Lys Leu Thr Val Leu
        115
```

<210> SEQ ID NO 219
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 219

```
cagcctgtgc tgactcagcc ggcttccctc tctgcatctc ctggagcatc agccagtctc      60
acctgcacct tgcgcagtgg catcaacgtt aaggattaca ggatattctg gtaccagcag     120
aagccaggga gtcctcccca gtatctcctg aggtacaaaa gcgaatcaga taagcagcag     180
ggctctggag tccccagccg cttctctggg tccaaagatg cttcggccaa tgcagggatt     240
ttactcatct ctgggctcca gtctgaggat gaggctgact attactgtat gatttggcac     300
aaggatcggg aggggcatgc ttttgtgttc ggcggaggga ccaagctgac cgtccta       357
```

<210> SEQ ID NO 220
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 220

```
Gln Pro Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Lys Asp
            20                  25                  30

Tyr Arg Ile Phe Trp Tyr Gln Gln Lys Pro Gly Ser Pro Pro Gln Tyr
        35                  40                  45

Leu Leu Arg Tyr Lys Ser Glu Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80
```

Leu Leu Ile Ser Gly Leu Gln Ser Glu Asp Glu Ala Asp Tyr Tyr Cys
                85                  90                  95

Met Ile Trp His Lys Asp Arg Glu Gly His Ala Phe Val Phe Gly Gly
            100                 105                 110

Gly Thr Lys Leu Thr Val Leu
        115

<210> SEQ ID NO 221
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 221
cagcctgtgc tgactcagcc ggcttccctc tctgcatctc ctggggcatc agccagtctc      60
acctgcacct tgcgcagtgg catcaacgtt agagattaca ggatattctg gtaccagcag     120
aagccaggga gtcctcccca gtatctcctg aggtacaaaa gcgcatcaga taagcagcag     180
ggctctggag tccccagccg cttctctggg tccaaagatg cttcggccaa tgcagggatt     240
ttactcatct ctgggctcca gtctgaggat gaggctgact attactgtat gatttggcac     300
cacgattcgg aggggcatgc ttttgtgttc ggcggaggga ccaagctgac cgtccta       357

<210> SEQ ID NO 222
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 222

Gln Pro Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Arg Asp
            20                  25                  30

Tyr Arg Ile Phe Trp Tyr Gln Gln Lys Pro Gly Ser Pro Pro Gln Tyr
        35                  40                  45

Leu Leu Arg Tyr Lys Ser Ala Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His His Asp Ser Glu Gly His Ala Phe Val Phe Gly Gly
            100                 105                 110

Gly Thr Lys Leu Thr Val Leu
        115

<210> SEQ ID NO 223
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 223
tcctatgtgc tgactcagcc accctcagtg tcagtggccc caggaaagac ggccaggatt      60
acctgtgggg gaaacaaaat tggacaccgc gccgtgcact ggtaccagca gaagccaggc     120

```
caggcccctg tgctggtcat ctattatacc tatgagcggc cctcagggat tcctgagcga    180
ttctctggct ccaactctgg gaacacggcc accctgacca tcagcagggt cgaagccggg    240
gatgaggccg actattactg tcaggtgtgg gattggtaca gcgagggggg ggttgtgttc    300
ggcggaggga ccaagctgac cgtcctaggt cagcccaagg ctgccccctc ggtcactctg    360
```

<210> SEQ ID NO 224
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 224

Ser Tyr Val Leu Thr Gln Pro Pro Ser Val Ser Val Ala Pro Gly Lys
1               5                   10                  15

Thr Ala Arg Ile Thr Cys Gly Gly Asn Lys Ile Gly His Arg Ala Val
            20                  25                  30

His Trp Tyr Gln Gln Lys Pro Gly Gln Ala Pro Val Leu Val Ile Tyr
        35                  40                  45

Tyr Thr Tyr Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Trp Tyr Ser Glu Gly
                85                  90                  95

Gly Val Val Phe Gly Gly Gly Thr Lys Leu Thr Val Leu Gly Gln Pro
            100                 105                 110

Lys Ala Ala Pro Ser Val Thr Leu
        115                 120

<210> SEQ ID NO 225
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 225

Gly Phe Thr Phe Ser Ser Tyr Ala
1               5

<210> SEQ ID NO 226
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 226

Ile Ser Gly Ser Gly Gly Ser Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 227

Ala Lys Ser Tyr Gly Ala Phe Asp Tyr
1               5

<210> SEQ ID NO 228
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 228

Gln Asp Ile Asn Lys Tyr
1               5

<210> SEQ ID NO 229
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 229

Gln Asp Ile Asn Arg Tyr
1               5

<210> SEQ ID NO 230
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 230

Gln Asn Ile Gly Lys Tyr
1               5

<210> SEQ ID NO 231
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 231

Gln Ser Ile Ala Arg Tyr
1               5

<210> SEQ ID NO 232
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 232

Gln Ser Ile Ala Ser Tyr
1               5

<210> SEQ ID NO 233
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 233

Gln Ser Ile Asp Lys Tyr
1               5

<210> SEQ ID NO 234
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 234

Gln Ser Ile Asp Arg Tyr
1               5

<210> SEQ ID NO 235
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 235

Gln Ser Ile Gly Lys Tyr
1               5

<210> SEQ ID NO 236
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 236

Gln Ser Ile Gly Arg Tyr
1               5

<210> SEQ ID NO 237
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 237

Gln Ser Ile Asn Arg Tyr
1               5

<210> SEQ ID NO 238
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 238

Gln Ser Ile Ser Lys Tyr
1               5

<210> SEQ ID NO 239
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 239

Gln Ser Ile Ser Arg Tyr
1               5

<210> SEQ ID NO 240
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 240

Gln Ser Ile Ser Ser Tyr
1               5

<210> SEQ ID NO 241
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 241

Gln Ser Ile Ala Lys Tyr
1               5

<210> SEQ ID NO 242
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 242

Ala Ala Ser
1

<210> SEQ ID NO 243
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 243

Gly Ala Ser
1

<210> SEQ ID NO 244
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 244

Asn Ala Ser
1

<210> SEQ ID NO 245
<211> LENGTH: 3
<212> TYPE: PRT
<213> ORGANISM: Artificial Sequence
<220> FEATURE:
<223> OTHER INFORMATION: Synthetic Polypeptide
```

```
<400> SEQUENCE: 245

Ser Ala Ser
1

<210> SEQ ID NO 246
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 246

Gln Gln Lys His Pro Arg Gly Pro Arg Thr
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 247

Gln Gln Phe His Lys Arg Ala Pro Gln Thr
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 248

Gln Gln Phe His Lys Arg Arg Pro Gln Thr
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 249

Gln Gln Phe His Lys Arg Ser Pro Gln Thr
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 250

Gln Gln Lys His Pro Arg Ala Pro Arg Thr
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 251

Gln Gln Lys His Pro Arg Ser Pro Arg Thr
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 252

Gln Gln Lys His Pro Arg Tyr Pro Arg Thr
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 253

Gln Gln Lys His Pro Arg Asn Pro Arg Thr
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 254

Gln Gln Met His Pro Arg Ala Pro Lys Thr
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 255

Gln Gln Met His Pro Arg Gly Pro Lys Thr
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 256

Gln Gln Met His Pro Arg Ser Pro Lys Thr
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 257

Gln Gln Arg His Pro Arg Ala Pro Arg Thr
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 258

Gln Gln Arg His Lys Arg Ser Pro Gln Thr
1               5                   10

<210> SEQ ID NO 259
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 259

Gln Gln Arg His Pro Arg Gly Pro Arg Thr
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 260

Gln Gln Arg His Pro Arg Gly Pro Ser Thr
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 261

Gln Gln Arg His Pro Arg Gly Pro Thr Thr
1               5                   10

<210> SEQ ID NO 262
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 262

Ser Ser Asp Val Gly Gly Tyr Asn Tyr
1               5

<210> SEQ ID NO 263
<211> LENGTH: 9
<212> TYPE: PRT
<213> ORGANISM: Artificial Sequence
<220> FEATURE:
<223> OTHER INFORMATION: Synthetic Polypeptide
```

```
<400> SEQUENCE: 263

Ser Ser Asp Val Glu Arg Lys Asn Tyr
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 264

Ser Ser Asp Val Arg Ala Asn Asn Tyr
1               5

<210> SEQ ID NO 265
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 265

Ser Ser Asp Val Tyr Tyr Asn Lys Tyr
1               5

<210> SEQ ID NO 266
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 266

Ser Ser Asp Val Gly Lys Ala Asn Tyr
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 267

Ser Ser Asp Val Arg Gly Asn Asn Tyr
1               5

<210> SEQ ID NO 268
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 268

Ser Ser Asp Val Ser Ala Arg Asn Tyr
1               5

<210> SEQ ID NO 269
<211> LENGTH: 9
<212> TYPE: PRT
<213> ORGANISM: Artificial Sequence
<220> FEATURE:
<223> OTHER INFORMATION: Synthetic Polypeptide
```

```
<400> SEQUENCE: 269

Ser Ser Asp Val Asn Ser Ala Asn Tyr
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 270

Ser Ser Asp Val Arg Ala Ala Asn Tyr
1               5

<210> SEQ ID NO 271
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 271

Ser Ser Asp Val Arg Arg Ala Asn Tyr
1               5

<210> SEQ ID NO 272
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 272

Ser Ser Asp Val Asn Asn Thr Asn Tyr
1               5

<210> SEQ ID NO 273
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 273

Glu Asn Ser
1

<210> SEQ ID NO 274
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 274

Glu Ser Ser
1

<210> SEQ ID NO 275
<211> LENGTH: 3
<212> TYPE: PRT
<213> ORGANISM: Artificial Sequence
<220> FEATURE:
<223> OTHER INFORMATION: Synthetic Polypeptide
```

```
<400> SEQUENCE: 275

Glu Val Ser
1

<210> SEQ ID NO 276
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 276

Lys Asp Ser
1

<210> SEQ ID NO 277
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 277

Lys Asn Ser
1

<210> SEQ ID NO 278
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 278

Lys Ser Ser
1

<210> SEQ ID NO 279
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 279

Lys Thr Ser
1

<210> SEQ ID NO 280
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 280

Gln Asp Ser
1

<210> SEQ ID NO 281
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 281

Ser Ser Tyr Asp Trp Trp Phe Arg Pro Lys Val
1               5                   10

<210> SEQ ID NO 282
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 282

Lys Ile Gly His Arg Ala
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 283

Ser Gly Ile Ser Val Lys Asp Tyr Arg
1               5

<210> SEQ ID NO 284
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 284

Ser Ser Asn Ile Ala His Gly Pro
1               5

<210> SEQ ID NO 285
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 285

Ser Gly Ile Asn Val Lys Asp Tyr Arg
1               5

<210> SEQ ID NO 286
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 286

Ser Gly Ile Asn Val Arg Asp Tyr Arg
1               5

<210> SEQ ID NO 287
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 287

Ser Asp Ile Arg Val Arg Asp Tyr Arg
1               5

<210> SEQ ID NO 288
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 288

Tyr Thr Tyr
1

<210> SEQ ID NO 289
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 289

Tyr Lys Ser Asn Ser Asp Met
1               5

<210> SEQ ID NO 290
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 290

Ala Thr Asn
1

<210> SEQ ID NO 291
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 291

Tyr Lys Ser Glu Ser Asp Lys
1               5

<210> SEQ ID NO 292
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 292

Tyr Lys Ser Ala Ser Asp Lys
1               5

<210> SEQ ID NO 293
<211> LENGTH: 7
<212> TYPE: PRT
<213> ORGANISM: Artificial Sequence
<220> FEATURE:
<223> OTHER INFORMATION: Synthetic Polypeptide
```

```
<400> SEQUENCE: 293

Tyr Lys Thr Asp Ser Asp Lys
1               5

<210> SEQ ID NO 294
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 294

Gln Val Trp Asp Ala Ser Arg Arg Asp Ala Asn Val Val
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 295

Met Ile Trp His His Gly His Gly Thr Ser Leu Val
1               5                   10

<210> SEQ ID NO 296
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 296

Ala Ala Tyr Asp Leu Thr Gly Trp Phe Ala Tyr Ala Val
1               5                   10

<210> SEQ ID NO 297
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 297

Met Ile Trp His Lys Asp Arg Glu Gly His Ala Phe Val
1               5                   10

<210> SEQ ID NO 298
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 298

Met Ile Trp His His Asp Ser Glu Gly His Ala Phe Val
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Synthetic Polypeptide
```

```
<400> SEQUENCE: 299

Met Ile Trp His Arg Thr Thr Gly Thr Ser Leu Val
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 300

Gln Val Trp Asp Trp Tyr Ser Glu Gly Gly Val Val
1               5                   10
```

ANTI-CD47 X ANTI-MESOTHELIN ANTIBODIES AND METHODS OF USE THEREOF

RELATED APPLICATIONS

This application claims the benefit of U.S. Provisional Application No. 62/511,669, filed on May 26, 2017, and U.S. Provisional Application No. 62/550,387, filed on Aug. 25, 2017. The contents of each of these applications are incorporated herein by reference in their entireties.

INCORPORATION-BY-REFERENCE OF SEQUENCE LISTING

The contents of the file named "NOVI-044_001US_SequenceListing_ST25", which was created on May 22, 2018, and is 268 KB in size are hereby incorporated by reference in their entirety.

BACKGROUND OF THE INVENTION

CD47 or Integrin-Associated-Protein (IAP) is a ubiquitous 50 kDa transmembrane glycoprotein with multiple functions in cell-cell communication. It interacts with multiple ligands, such as integrins, SIRPα (Signal Regulatory Protein alpha), SIRPγ and thrombospondins (Oldenborg, P. A., CD47: A Cell Surface Glycoprotein Which Regulates Multiple Functions of Hematopoietic Cells in Health and Disease, ISRN Hematol. 2013; 2013:614619; Soto-Pantoja D R, et al., Therapeutic opportunities for targeting the ubiquitous cell surface receptor CD47 (2012), Expert Opin Ther Targets. 2013 January; 17(1):89-103; Sick E, et al., CD47 Update: a multifaced actor in the tumor microenvironment of potential therapeutic interest, Br J Pharmacol. 2012 December; 167(7):1415-30).

The widespread expression of CD47 in healthy tissues brings the question of treatment safety and efficacy: First, targeting CD47 with a neutralizing monoclonal antibody (Mab) could affect healthy cells, resulting in severe toxicities as shown in preclinical studies with mice and cynomolgus monkeys (Willingham S B, et al., Proc Natl Acad Sci USA. 2012 Apr. 24; 109(17):6662-7; Weiskopf K, et al., Engineered SIRPα Variants as Immunotherapeutic Adjuvants to Anticancer Antibodies, Science. 2013 Jul. 5; 341 (6141):88-91). Second, even if severe toxicities could be avoided or mitigated by using alternative formats (Weiskopf K, et al., Science. 2013 Jul. 5; 341(6141):88-91), broad expression of CD47 could still cause a rapid elimination of CD47-binding molecules through target-mediated drug disposition resulting in poor pharmacokinetics and decreased efficacy.

Accordingly, there exists a need for antibodies and therapeutics that enable targeting of CD47 and overcome these obstacles.

SUMMARY OF THE INVENTION

The invention also provides bispecific antibodies that recognize CD47 and mesothelin. CD47 (Cluster of Differentiation 47) functions as a "don't eat me" signal for phagocytic cells and is known to be over-expressed by many tumors (immune escape). CD47 interacts with SIRPα, which is expressed on phagocytic cells. CD47 down-regulates phagocytic activity. CD47 inhibits dendritic cell (DC) maturation and activation. CD47 has also been implicated in processes such as, for example, apoptosis, survival, proliferation, adhesion, migration, and regulation of angiogenesis, blood pressure, tissue perfusion, and/or platelet homeostasis.

CD47 has also been implicated in cancer. For example, CD47 is overexpressed in various hematological and solid malignancies. CD47 is a documented cancer stem cell/tumor initiating cell marker. It is thought that CD47 overexpression may help tumor cells to escape immune surveillance and killing by innate immune cells. High levels of CD47 are also associated with poor clinical outcome in cancers such as, for example, leukemias, lymphomas, breast cancer, colon cancer, ovarian cancer, bladder cancer, prostate cancer, and/or glioma. Thus, targeting CD47 would be useful in treating, delaying the progression of, or otherwise ameliorating a symptom of cancer.

Mesothelin (MSLN) is expressed in normal tissues at relatively low levels. In contrast to normal tissues, mesothelin is highly expressed in several types of solid tumors such as malignant mesothelioma, ovarian cancer, pancreatic adenocarcinoma, lung adenocarcinoma, as well as endometrial, biliary gastric and prostate cancers. Tumor mesothelin expression has often been correlated with increased tumor aggressiveness and poor clinical outcome. Thus, targeting mesothelin would be useful in treating, delaying the progression of, or otherwise ameliorating a symptom of cancer.

The disclosure also provides bispecific antibodies that include at least a first arm that is specific for CD47. In some embodiments, the first arm is specific for at least human CD47. In some embodiments, the first arm recognizes human CD47 and is also cross-reactive for at least one other non-human CD47 protein, such as, by way of non-limiting example, non-human primate CD47, e.g., cynomolgus monkey CD47, and/or rodent CD47. In some embodiments, these anti-CD47 monoclonal antibodies inhibit the interaction between CD47 and signal-regulatory protein alpha (SIRPα). In some embodiments, these bispecific antibodies inhibit the interaction between human CD47 and human SIRPα. The invention also include antibodies that bind to the same epitope as a bispecific antibody disclosed herein and inhibits the interaction between CD47 and SIRPα, e.g., between human CD47 and human SIRPα.

The disclosure also provides bispecific antibodies that recognize CD47 and a second target. The disclosure allows for the identification, production and purification of bispecific antibodies that are undistinguishable in sequence from standard antibodies and where one of the binding sites is specific for CD47 and the second binding site is specific for another target, for example a tumor-associated antigen (TAA). In some embodiments, the TAA is an antigen that is expressed on the cell surface of a cancer cell. In some embodiments, the cancer cell is selected from a lung cancer cell, a bronchial cancer cell, a prostate cancer cell, a breast cancer cell, a colorectal cancer cell, a pancreatic cancer cell, an ovarian, a leukemia cancer cell, a lymphoma cancer cell, an esophageal cancer cell, a liver cancer cell, a urinary and/or bladder cancer cell, a renal cancer cell, an oral cavity cancer cell, a pharyngeal cancer cell, a uterine cancer cell, and/or a melanoma cancer cell.

The bispecific antibodies of the invention that bind at least CD47 and fragments thereof serve to modulate, block, inhibit, reduce, antagonize, neutralize or otherwise interfere with the functional activity of CD47. Functional activities of CD47 include, by way of non-limiting example, interaction with SIRPα. The antibodies are considered to completely modulate, block, inhibit, reduce, antagonize, neutralize or otherwise interfere with the CD47-SIRPα interaction when the level of CD47-SIRPα interaction in the presence of the antibody is decreased by at least 95%, e.g., by 96%, 97%, 98%, 99% or 100% as compared to the level of CD47-SIRPα interaction in the absence of binding with an antibody described herein. The antibodies are considered to partially modulate, block, inhibit, reduce, antagonize, neutralize or otherwise interfere with the CD47-SIRPα interaction when the level of CD47-SIRPα interaction in the presence of the antibody is decreased by less than 95%, e.g., 10%, 20%, 25%, 30%, 40%, 50%, 60%, 75%, 80%, 85% or 90% as compared to the level of CD47-SIRPα interaction in the absence of binding with an antibody described herein.

In some embodiments, the bispecific antibody exhibits a "balanced" affinity for each of the two targets. In other embodiments, the bispecific antibody exhibits an "unbalanced" affinity for each of the two targets. For example, in an anti-CD47/MSLN bispecific antibody, the affinity of the anti-MSLN arm is increased. For example, in an anti-CD47/MSLN bispecific antibody, the affinity of the anti-CD47 arm is decreased. For example, in an anti-CD47/MSLN bispecific antibody, the affinity of the anti-MSLN arm is increased and the affinity of the anti-CD47 arm is decreased. These unbalanced affinity bispecific antibodies are useful, for example, to improve selectivity for a target cell or group of target cells.

In some embodiments, the affinity of the anti-MSLN arm is increased by at least 100 fold following affinity maturation. In some embodiments, the affinity of the anti-CD47 arm is decreased by at least 2 fold following affinity dematuration. For example, in some embodiments, the anti-CD47 arm exhibits an affinity for CD47 that is between about 2 fold and 100 fold lower following affinity dematuration.

In some embodiments, the first arm amino acid sequence includes a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 228-241 and 262-272, a variable light chain complementarity determining region 2 (CDRL2) amino acid sequence selected from SEQ ID NO: 242-245 and 273-280, and a variable light chain complementarity determining region 3 (CDRL3) amino acid sequence selected from SEQ ID NO: 246-261 and 281.

In some embodiments, the first arm amino acid sequence includes a variable heavy chain amino acid sequence of SEQ ID NO: 114 and a variable light chain amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

In some embodiments, the first arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 240, a variable light chain complementarity determining region 2 (CDRL2) comprising the amino acid sequence of SEQ ID NO: 242, and a variable light chain complementarity determining region 3 (CDRL3) comprising the amino acid sequence of SEQ ID NO: 254.

In some embodiments, the first arm amino acid sequence includes a variable heavy chain amino comprising the acid sequence of SEQ ID NO: 114 and a variable light chain comprising the amino acid sequence of SEQ ID NO: 168.

In some embodiments, the first arm amino acid sequence includes a heavy chain amino comprising the acid sequence of SEQ ID NO: 2 and a variable light chain comprising the amino acid sequence of SEQ ID NO: 56.

In some embodiments, the second arm amino acid sequence includes a heavy chain amino acid sequence of SEQ ID NO: 2 and a light chain amino acid sequence selected from the group consisting of SEQ ID NO: 98, 100, 102, 104, 106, 108, and 110.

In some embodiments, the second arm amino acid sequence includes a variable heavy chain amino acid sequence of SEQ ID NO: 114 and a variable light chain amino acid sequence selected from the group consisting of SEQ ID NO: 212, 214, 216, 218, 220, 222, and 224.

In some embodiments, the second arm amino acid sequence includes a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 282-287, a variable light chain complementarity determining region 2 (CDRL2) amino acid sequence selected from SEQ ID NO: 288-293, and a variable light chain complementarity determining region 3 (CDRL3) amino acid sequence selected from the group consisting of SEQ ID NO: 294-300.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 282, a variable light chain complementarity determining region 2 (CDRL2) comprising the amino acid sequence of SEQ ID NO: 288, and a variable light chain complementarity determining region 3 (CDRL3) comprising the amino acid sequence of SEQ ID NO: 294.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 283, a variable light chain complementarity determining region 2 (CDRL2) comprising the amino acid sequence of SEQ ID NO: 289, and a variable light chain complementarity determining region 3 (CDRL3) comprising the amino acid sequence of SEQ ID NO: 295.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 284, a variable light chain complementarity determining region 2 (CDRL2) comprising the amino acid sequence of SEQ ID NO: 290, and a variable light chain complementarity determining region 3 (CDRL3) comprising the amino acid sequence of SEQ ID NO: 296.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 285, a variable light chain complementarity determining region 2 (CDRL2) comprising the amino acid sequence of SEQ ID NO: 291, and a variable light chain complementarity determining region 3 (CDRL3) comprising the amino acid sequence of SEQ ID NO: 297.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 286, a variable light chain complementarity determining region 2 (CDRL2) comprising the amino acid sequence of SEQ ID NO: 292, and a variable light chain complementarity determining region 3 (CDRL3) comprising the amino acid sequence of SEQ ID NO: 298.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 287, a variable light chain complementarity determining region 2 (CDRL2) comprising the amino acid sequence of SEQ ID NO: 293, and a variable light chain complementarity determining region 3 (CDRL3) comprising the amino acid sequence of SEQ ID NO: 299.

In some embodiments, the second arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 282, a variable light chain complementarity determining region 2 (CDRL2) comprising the amino acid sequence of SEQ ID NO: 288, and a variable light chain complementarity determining region 3 (CDRL3) comprising the amino acid sequence of SEQ ID NO: 300.

In some embodiments, the second arm amino acid sequence includes a variable heavy chain amino comprising the acid sequence of SEQ ID NO: 114 and a variable light chain comprising an amino acid sequence selected from the group consisting of SEQ ID NO: 212, 214, 216, 218, 220, 222, and 224.

In some embodiments, the second arm amino acid sequence includes a variable heavy chain amino comprising the acid sequence of SEQ ID NO: 114 and a variable light chain comprising the amino acid sequence of SEQ ID NO: 212.

In some embodiments, the second arm amino acid sequence includes a variable heavy chain amino comprising the acid sequence of SEQ ID NO: 114 and a variable light chain comprising the amino acid sequence of SEQ ID NO: 214.

In some embodiments, the second arm amino acid sequence includes a variable heavy chain amino comprising the acid sequence of SEQ ID NO: 114 and a variable light chain comprising the amino acid sequence of SEQ ID NO: 216.

In some embodiments, the second arm amino acid sequence includes a variable heavy chain amino comprising the acid sequence of SEQ ID NO: 114 and a variable light chain comprising the amino acid sequence of SEQ ID NO: 218.

In some embodiments, the second arm amino acid sequence includes a variable heavy chain amino comprising the acid sequence of SEQ ID NO: 114 and a variable light chain comprising the amino acid sequence of SEQ ID NO: 220.

In some embodiments, the second arm amino acid sequence includes a variable heavy chain amino comprising the acid sequence of SEQ ID NO: 114 and a variable light chain comprising the amino acid sequence of SEQ ID NO: 222.

In some embodiments, the second arm amino acid sequence includes a variable heavy chain amino comprising the acid sequence of SEQ ID NO: 114 and a variable light chain comprising the amino acid sequence of SEQ ID NO: 224.

In some embodiments, the second arm amino acid sequence includes a heavy chain amino comprising the acid sequence of SEQ ID NO: 2 and a light chain comprising an amino acid sequence selected from the group consisting of SEQ ID NO: 98, 100, 102, 104, 106, 108, and 110.

In some embodiments, the second arm amino acid sequence includes a heavy chain amino comprising the acid sequence of SEQ ID NO: 2 and a light chain comprising the amino acid sequence of SEQ ID NO: 98.

In some embodiments, the second arm amino acid sequence includes a heavy chain amino comprising the acid sequence of SEQ ID NO: 2 and a light chain comprising the amino acid sequence of SEQ ID NO: 100.

In some embodiments, the second arm amino acid sequence includes a heavy chain amino comprising the acid sequence of SEQ ID NO: 2 and a light chain comprising the amino acid sequence of SEQ ID NO: 102.

In some embodiments, the second arm amino acid sequence includes a heavy chain amino comprising the acid sequence of SEQ ID NO: 2 and a light chain comprising the amino acid sequence of SEQ ID NO: 104.

In some embodiments, the second arm amino acid sequence includes a heavy chain amino comprising the acid sequence of SEQ ID NO: 2 and a light chain comprising the amino acid sequence of SEQ ID NO: 106.

In some embodiments, the second arm amino acid sequence includes a heavy chain amino comprising the acid sequence of SEQ ID NO: 2 and a light chain comprising the amino acid sequence of SEQ ID NO: 108.

In some embodiments, the second arm amino acid sequence includes a heavy chain amino comprising the acid sequence of SEQ ID NO: 2 and a light chain comprising the amino acid sequence of SEQ ID NO: 110.

In some embodiments, the first arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 240, a variable light chain complementarity determining region 2 (CDRL2) comprising the amino acid sequence of SEQ ID NO: 242, and a variable light chain complementarity determining region 3 (CDRL3) comprising the amino acid sequence of SEQ ID NO: 254, and the second arm amino acid sequence includes a variable light chain complementarity determining region 1 (CDRL1) amino acid sequence selected from SEQ ID NO: 282-287, a variable light chain complementarity determining region 2 (CDRL2) amino acid sequence selected from SEQ ID NO: 288-293, and a variable light chain complementarity determining region 3 (CDRL3) amino acid sequence selected from the group consisting of SEQ ID NO: 294-300.

In some embodiments, the first arm amino acid sequence includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 240, a variable light chain complementarity determining region 2 (CDRL2) comprising the amino acid sequence of SEQ ID NO: 242, and a variable light chain complementarity determining region 3 (CDRL3) comprising the amino acid sequence of SEQ ID NO: 254, and the second arm amino acid sequence includes a variable light chain complementarity determining region 1 (CDRL1) comprising the amino acid sequence of SEQ ID NO: 282, a variable light chain complementarity determining region 2 (CDRL2) comprising the amino acid sequence of SEQ ID NO: 288, and a variable light chain complementarity determining region 3 (CDRL3) comprising the amino acid sequence of SEQ ID NO: 294.

In some embodiments, the first arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and the second arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 283, a CDRL2 comprising the amino acid sequence of SEQ ID NO: 289, and a CDRL3 comprising the amino acid sequence of SEQ ID NO: 295.

In some embodiments, the first arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and the second arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 284, a CDRL2 comprising the amino acid sequence of SEQ ID NO: 290, and a CDRL3 comprising the amino acid sequence of SEQ ID NO: 296.

In some embodiments, the first arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and the second arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 285, a CDRL2 comprising the amino acid sequence of SEQ ID NO: 291, and a CDRL3 comprising the amino acid sequence of SEQ ID NO: 297.

In some embodiments, the first arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and the second arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 286, a CDRL2 comprising the amino acid sequence of SEQ ID NO: 292, and a CDRL3 comprising the amino acid sequence of SEQ ID NO: 298.

In some embodiments, the first arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and the second arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 287, a CDRL2 comprising the amino acid sequence of SEQ ID NO: 293, and a CDRL3 comprising the amino acid sequence of SEQ ID NO: 299.

In some embodiments, the first arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and the second arm amino acid sequence includes a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a CDRL1 comprising the amino acid sequence of SEQ ID NO: 282, a CDRL2 comprising the amino acid sequence of SEQ ID NO: 288, and a CDRL3 comprising the amino acid sequence of SEQ ID NO: 300.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain comprising the amino acid sequence of SEQ ID NO: 114 and a variable light chain comprising an amino acid sequence selected from the group consisting of SEQ ID NO: 212, 214, 216, 218, 220, 222, and 224.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 212.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 214.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 216.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 218.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 220.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 222.

In some embodiments, the first arm amino acid sequence includes a variable heavy chain comprising the amino acid sequence of SEQ ID NO: 114 and a variable light chain comprising the amino acid sequence of SEQ ID NO: 168, and the second arm amino acid sequence includes a variable heavy chain amino comprising the acid sequence of SEQ ID NO: 114 and a variable light chain comprising the amino acid sequence of SEQ ID NO: 224.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain comprising the amino acid sequence of SEQ ID NO: 2 and a light chain comprising an amino acid sequence selected from the group consisting of SEQ ID NO: 98, 100, 102, 104, 106, 108, and 110.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 98.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 100.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 102.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 104.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 106.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 108.

In some embodiments, the first arm amino acid sequence includes a heavy chain comprising the amino acid sequence of SEQ ID NO: 2 and a light chain comprising the amino acid sequence of SEQ ID NO: 168, and the second arm amino acid sequence includes a heavy chain amino comprising the acid sequence of SEQ ID NO: 2 and a light chain comprising the amino acid sequence of SEQ ID NO: 110.

In some embodiments, the bispecific antibody includes two copies of a single heavy chain polypeptide and a first light chain and a second light chain, wherein the first and second light chains are different.

In some embodiments, at least a portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and wherein the second light chain includes a Lambda constant region and a Lambda variable region.

In some embodiments, the constant and variable framework region sequences are human.

The bispecific antibodies of the invention are generated using any methods known in the art such as, by way of non-limiting example, the use of cross-linked fragments, quadromas, and/or any of a variety of recombinant formats such as, by way of non-limiting examples, linked antibody fragments, forced heterodimers, and or recombinant formats based on single domains. Examples of Bispecific formats include but are not limited to bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46.) or knob-into-hole (Ridgway J B et al., Protein Eng. 1996 9(7):617-21.) or other sets of mutations preventing homodimer formation (Von Kreudenstein T S et al., 2013 MAbs. 5(5):646-54.); fragment based bispecific formats such as tandem scFv (such asBiTEs) (Wolf E et al., 2005 Drug Discov. Today 10(18):1237-44.); bispecific tetravalent antibodies (Portner L M et al., 2012 Cancer Immunol Immunother. 61(10):1869-75.); dual affinity retargeting molecules (Moore P A et al., 2011 Blood. 117(17):4542-51), diabodies (Kontermann R E et al., Nat Biotechnol. 1997 15(7):629-31).

In some embodiments, the bispecific antibodies carry a different specificity in each combining site and including two copies of a single heavy chain polypeptide and a first light chain and a second light chain, wherein the first and second light chains are different. In some embodiments, at least a first portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and the second light chain includes a Lambda constant region and a Lambda variable region. In some embodiments, the constant and variable framework region sequences are human.

The invention provides monoclonal antibodies that bind MSLN. These antibodies are collectively referred to herein as anti-MSLN monoclonal antibodies or anti-MSLN mAbs. Preferably, the monoclonal antibodies are specific for at least human MSLN. In some embodiments, the monoclonal antibodies that recognize human MSLN are also cross-reactive for at least one other non-human MSLN protein, such as, by way of non-limiting example, non-human primate MSLN, e.g., cynomolgus monkey MSLN, and/or rodent MSLN.

In some embodiments, the anti-MSLN monoclonal antibody includes a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 282-287, a variable light chain complementarity determining region 2 (CDRL2) amino acid sequence selected from SEQ ID NO: 288-293, and a variable light chain complementarity determining region 3 (CDRL3) amino acid sequence selected from the group consisting of SEQ ID NO: 294-300.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 282, a variable light chain complementarity determining region 2 (CDRL2) comprising the amino acid sequence of SEQ ID NO: 288, and a variable light chain complementarity determining region 3 (CDRL3) comprising the amino acid sequence of SEQ ID NO: 294.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 283, a variable light chain complementarity determining region 2 (CDRL2) comprising the amino acid sequence of SEQ ID NO: 289, and a variable light chain complementarity determining region 3 (CDRL3) comprising the amino acid sequence of SEQ ID NO: 295.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 284, a variable light chain complementarity determining region 2 (CDRL2) comprising the amino acid sequence of SEQ ID NO: 290, and a variable light chain complementarity determining region 3 (CDRL3) comprising the amino acid sequence of SEQ ID NO: 296.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 285, a variable light chain complementarity determining region 2 (CDRL2) comprising the amino acid sequence of SEQ ID NO: 291, and a variable light chain complementarity determining region 3 (CDRL3) comprising the amino acid sequence of SEQ ID NO: 297.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 286, a variable light chain complementarity determining region 2 (CDRL2) comprising the amino acid sequence of SEQ ID NO: 292, and a variable light chain complementarity determining region 3 (CDRL3) comprising the amino acid sequence of SEQ ID NO: 298.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 287, a variable light chain complementarity determining region 2 (CDRL2) comprising the amino acid sequence of SEQ ID NO: 293, and a variable light chain complementarity determining region 3 (CDRL3) comprising the amino acid sequence of SEQ ID NO: 299.

In some embodiments, the anti-MSLN monoclonal antibody includes a variable heavy chain complementarity determining region 1 (CDRH1) comprising the amino acid sequence of SEQ ID NO: 225, a variable heavy chain complementarity determining region 2 (CDRH2) comprising the amino acid sequence of SEQ ID NO: 226, a variable heavy chain complementarity determining region 3 (CDRH3) comprising the amino acid sequence of SEQ ID NO: 227, a variable light chain complementarity determining region 1 (CDRL1) comprising the amino acid sequence of SEQ ID NO: 282, a variable light chain complementarity determining region 2 (CDRL2) comprising the amino acid sequence of SEQ ID NO: 288, and a variable light chain complementarity determining region 3 (CDRL3) comprising the amino acid sequence of SEQ ID NO: 300.

In some embodiments, the anti-MSLN monoclonal antibody includes a variable heavy chain amino comprising the acid sequence of SEQ ID NO: 114 and a variable light chain comprising an amino acid sequence selected from the group consisting of SEQ ID NO: 212, 214, 216, 218, 220, 222, and 224.

In some embodiments, the anti-MSLN monoclonal antibody includes a variable heavy chain amino comprising the acid sequence of SEQ ID NO: 114 and a variable light chain comprising the amino acid sequence of SEQ ID NO: 212.

In some embodiments, the anti-MSLN monoclonal antibody includes a variable heavy chain amino comprising the acid sequence of SEQ ID NO: 114 and a variable light chain comprising the amino acid sequence of SEQ ID NO: 214.

In some embodiments, the anti-MSLN monoclonal antibody includes a variable heavy chain amino comprising the acid sequence of SEQ ID NO: 114 and a variable light chain comprising the amino acid sequence of SEQ ID NO: 216.

In some embodiments, the anti-MSLN monoclonal antibody includes a variable heavy chain amino comprising the acid sequence of SEQ ID NO: 114 and a variable light chain comprising the amino acid sequence of SEQ ID NO: 218.

In some embodiments, the anti-MSLN monoclonal antibody includes a variable heavy chain amino comprising the acid sequence of SEQ ID NO: 114 and a variable light chain comprising the amino acid sequence of SEQ ID NO: 220.

In some embodiments, the anti-MSLN monoclonal antibody includes a variable heavy chain amino comprising the acid sequence of SEQ ID NO: 114 and a variable light chain comprising the amino acid sequence of SEQ ID NO: 222.

In some embodiments, the anti-MSLN monoclonal antibody includes a variable heavy chain amino comprising the acid sequence of SEQ ID NO: 114 and a variable light chain comprising the amino acid sequence of SEQ ID NO: 224.

In some embodiments, the anti-MSLN monoclonal antibody includes a heavy chain amino comprising the acid sequence of SEQ ID NO: 2 and a light chain comprising an amino acid sequence selected from the group consisting of SEQ ID NO: 98, 100, 102, 104, 106, 108, and 110.

In some embodiments, the anti-MSLN monoclonal antibody includes a heavy chain amino comprising the acid sequence of SEQ ID NO: 2 and a light chain comprising the amino acid sequence of SEQ ID NO: 98.

In some embodiments, the anti-MSLN monoclonal antibody includes a heavy chain amino comprising the acid sequence of SEQ ID NO: 2 and a light chain comprising the amino acid sequence of SEQ ID NO: 100.

In some embodiments, the anti-MSLN monoclonal antibody includes a heavy chain amino comprising the acid sequence of SEQ ID NO: 2 and a light chain comprising the amino acid sequence of SEQ ID NO: 102.

In some embodiments, the anti-MSLN monoclonal antibody includes a heavy chain amino comprising the acid sequence of SEQ ID NO: 2 and a light chain comprising the amino acid sequence of SEQ ID NO: 104.

In some embodiments, the anti-MSLN monoclonal antibody includes a heavy chain amino comprising the acid sequence of SEQ ID NO: 2 and a light chain comprising the amino acid sequence of SEQ ID NO: 106.

In some embodiments, the anti-MSLN monoclonal antibody includes a heavy chain amino comprising the acid sequence of SEQ ID NO: 2 and a light chain comprising the amino acid sequence of SEQ ID NO: 108.

In some embodiments, the anti-MSLN monoclonal antibody includes a heavy chain amino comprising the acid sequence of SEQ ID NO: 2 and a light chain comprising the amino acid sequence of SEQ ID NO: 110.

In some embodiments, the anti-MSLN monoclonal antibody includes a variable heavy chain amino acid sequence that is at least 90%, 91%, 92%, 93%, 94%, 95%, 96%, 97%, 98%, 99% or more identical to amino acid sequence of SEQ ID NO: 114. In some embodiments, the anti-MSLN monoclonal antibody includes a variable light chain amino acid sequence that is at least 90%, 91%, 92%, 93%, 94%, 95%, 96%, 97%, 98%, 99% or more identical to the variable light chain portion of an amino acid sequence selected from SEQ ID NO: 98, 100, 102, 104, 106, 108, and 110. In some embodiments, the anti-MSLN monoclonal antibody includes a variable heavy chain amino acid sequence that is at least 90%, 91%, 92%, 93%, 94%, 95%, 96%, 97%, 98%, 99% or more identical to the amino acid sequence of SEQ ID NO: 114, and a variable light chain amino acid sequence that is at least 90%, 91%, 92%, 93%, 94%, 95%, 96%, 97%, 98%, 99% or more identical to a variable light chain amino acid sequence selected from SEQ ID NO: 212, 214, 216, 218, 220, 222, and 224.

In some embodiments, the anti-MSLN monoclonal antibody includes a heavy chain amino acid sequence that is at least 90%, 91%, 92%, 93%, 94%, 95%, 96%, 97%, 98%, 99% or more identical to amino acid sequence of SEQ ID NO: 2. In some embodiments, the anti-MSLN monoclonal antibody includes a light chain amino acid sequence that is at least 90%, 91%, 92%, 93%, 94%, 95%, 96%, 97%, 98%, 99% or more identical to an amino acid sequence selected from SEQ ID NO: 98, 100, 102, 104, 106, 108, and 110. In some embodiments, the anti-MSLN monoclonal antibody includes a heavy chain amino acid sequence that is at least 90%, 91%, 92%, 93%, 94%, 95%, 96%, 97%, 98%, 99% or more identical to the amino acid sequence of SEQ ID NO: 114, and a light chain amino acid sequence that is at least 90%, 91%, 92%, 93%, 94%, 95%, 96%, 97%, 98%, 99% or more identical to an amino acid sequence selected from SEQ ID NO: 98, 100, 102, 104, 106, 108, and 110.

In some embodiments, the anti-MSLN monoclonal antibody includes a heavy chain amino acid sequence of SEQ ID NO: 2 and a light chain amino acid sequence selected from SEQ ID NO: 98, 100, 102, 104, 106, 108, and 110.

The invention also provides monovalent antibodies that bind MSLN. These antibodies are collectively referred to herein as anti-MSLN monovalent antibodies or anti-MSLN monov mAbs. The monovalent antibodies of the invention include one arm that specific recognizes MSLN, and a second arm referred to herein as a dummy arm. The dummy arm includes an amino acid sequence that does not bind or otherwise cross-react with a human protein. In some embodiments, the dummy arm includes an amino acid sequence that does not bind or otherwise cross-react with a human protein that is found in whole blood. In some embodiments, the dummy arm includes an amino acid sequence that does not bind or otherwise cross-react with a human protein that is found in solid tissue. Preferably, the monovalent antibodies are specific for at least human MSLN. In some embodiments, the monovalent antibodies that recognize human MSLN are also cross-reactive for at least one other non-human MSLN protein, such as, by way of non-limiting example, non-human primate MSLN, e.g., cynomolgus monkey MSLN, and/or rodent MSLN.

The invention also provides bispecific antibodies that recognize MSLN and a second target.

The bispecific antibodies of the invention that recognize MSLN and a second target are generated using any methods known in the art such as, by way of non-limiting example, the use of cross-linked fragments, quadromas, and/or any of a variety of recombinant formats such as, by way of non-limiting examples, linked antibody fragments, forced heterodimers, and or recombinant formats based on single domains. The invention allows for the identification, production and purification of bispecific antibodies that are undistinguishable in sequence from standard antibodies and where one of the binding sites is specific for MSLN and the second binding site is specific for another target, for example a tumor-associated antigen (TAA). The unmodified nature of the antibodies of the invention provides them with favorable manufacturing and biochemical characteristics similar to standard monoclonal antibodies.

In some embodiments, the bispecific antibodies carry a different specificity in each combining site and including two copies of a single heavy chain polypeptide and a first light chain and a second light chain, wherein the first and second light chains are different.

In some embodiments, at least a first portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and the second light chain includes a Lambda constant region and a Lambda variable region. In some embodiments, the constant and variable framework region sequences are human.

The monoclonal, monovalent and/or bispecific antibodies of the invention can be used for therapeutic intervention or as a research or diagnostic reagent. For example, the monoclonal, monovalent and/or bispecific antibodies of the invention are useful in methods of treating, preventing and/or delaying the progression of pathologies associated with aberrant CD47 and/or aberrant CD47-SIRPα expression and/or activity or alleviating a symptom associated with such pathologies, by administering an antibody of the invention to a subject in which such treatment or prevention is desired. The subject to be treated is, e.g., human. The monoclonal, monovalent and/or bispecific antibody is administered in an amount sufficient to treat, prevent, delay the progression or alleviate a symptom associated with the pathology.

In some embodiments, the monoclonal, monovalent and/or bispecific antibodies of the disclosure are useful in methods of treating, preventing and/or delaying the progression of, or alleviating a symptom of cancer or other neoplastic condition by administering an antibody of the invention to a subject in which such treatment or prevention is desired. For example, the monoclonal, monovalent and/or bispecific antibodies described herein are useful in treating hematological malignancies and/or solid tumors. For example, the monoclonal, monovalent and/or bispecific antibodies described herein are useful in treating CD47+ tumors, mesothelin+ tumors, and combinations thereof. By way of non-limiting example, the monoclonal, monovalent and/or bispecific antibodies described herein are useful in treating non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, mesothelioma, colorectal cancer, cholangiocarcinoma, pancreatic cancer, including pancreatic adenocarcinoma, lung cancer, including lung adenocarcinoma, leiomyoma, leiomyosarcoma, kidney cancer, glioma, glioblastoma, endometrial cancer, esophageal cancer, biliary gastric cancer, and prostate cancer. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

In some embodiments, the monoclonal, monovalent and/or bispecific antibodies described herein are used in conjunction with one or more additional agents or a combination of additional agents. Suitable additional agents include current pharmaceutical and/or surgical therapies for an intended application, such as, for example, cancer, inflammation and/or autoimmune diseases. In some embodiments, the monoclonal, monovalent and/or bispecific antibodies can be used in conjunction with rituximab.

In some embodiments, the monoclonal, monovalent and/or bispecific antibodies and the additional agent are formulated into a single therapeutic composition, and the monoclonal, monovalent and/or bispecific antibody and additional agent are administered simultaneously. Alternatively, the monoclonal, monovalent and/or bispecific antibodies and additional agent are separate from each other, e.g., each is formulated into a separate therapeutic composition, and the monoclonal, monovalent and/or bispecific antibody and the additional agent are administered simultaneously, or the monoclonal, monovalent and/or bispecific antibodies and the additional agent are administered at different times during a treatment regimen. For example, the monoclonal, monovalent and/or bispecific antibody is administered prior to the administration of the additional agent, the monoclonal, monovalent and/or bispecific antibody is administered subsequent to the administration of the additional agent, or the monoclonal, monovalent and/or bispecific antibody and the additional agent are administered in an alternating fashion. As described herein, the monoclonal, monovalent and/or bispecific antibody and additional agent are administered in single doses or in multiple doses.

Pathologies treated and/or prevented using the antibodies of the invention include, for example, cancer or any other disease or disorder associated with aberrant CD47 expression and/or activity.

Pharmaceutical compositions according to the invention can include an antibody of the invention and a carrier. These pharmaceutical compositions can be included in kits, such as, for example, diagnostic kits.

BRIEF DESCRIPTION OF THE DRAWINGS

FIGS. 1A-1G are a series of graphs depicting binding experiments with the CD47/MSLN κλ bodies to the corresponding MSLN mAbs. In FIGS. 1A-1G, the binding of biAb O25 (FIG. 1A), biAb O30 (FIG. 1B), biAb O32 (FIG. 1C), biAb O35 (FIG. 1D), biAb O37 (FIG. 1E), biAb O38 (FIG. 1F), and biAb O41 (FIG. 1G) to human MSLN transfected CHO cells (CHO-huMSLN, left), cynomolgus MSLN transfected CHO cells (CHO-cyMSLN, middle), and non-transfected CHO cells (right) was assessed in dose-response by flow cytometry and is presented as Mean Fluorescence Intensity. The comparison between CHO-huMSLN and CHO-cyMSLN binding profiles shows that the CD47/MSLN κλ bodies and the MSLN mAbs of the present invention are cross-reactive with cynomolgus MSLN and that they bind MSLN from both species with a comparable affinity.

In FIGS. 2A-2F, the level of ADCP induced is shown as shown the percentage of phagocytosis induced by increasing concentrations of bispecific antibodies (biAbs), the CD47 mAb B6H12 (with human IgG1 portion), the MSLN mAb amatuximab, and the matching anti-MSLN monovalent antibody (i.e., a κλ body with an anti-MSLN antibody arm and a non-binding antibody arm), as assessed by flow cytometry. Phagocytosis was done with human macrophages differentiated from peripheral blood monocytes and two target cell lines, NCI-N87 (FIGS. 2A-2C) and HPAC (FIGS. 2E and 2F). The levels of cell surface expression of CD47 and Mesothelin for NCI-N87 cells were 43,000 and 27,000, respectively. The levels of cell surface expression of CD47 and Mesothelin for HPAC cells were 105,000 and 13,000, respectively.

FIGS. 3A-3J depict phagocytic index, corresponding to the average number of target cells ingested by 100 macrophages. The levels of cell surface expression of CD47 and Mesothelin for NCI-N87 cells were 43,000 and 27,000, respectively. The levels of cell surface expression of CD47 and Mesothelin for Caov-3 cells were 220,000 and 38,000, respectively.

FIGS. 4A-4C are a series of graphs depicting a dose-response ADCC experiment with the CD47/MSLN κλ bodies compared to the benchmark MSLN monoclonal antibody amatuximab. The ADCC assay was performed with whole human PBMCs as effector cells and three Cr51-loaded MSLN-positive target cell lines, NCI-N87 (FIG. 4A) NCI-H226 (FIG. 4B) and HepG2-MSLN (FIG. 4C). Target cell killing was evaluated using a Cr51-release cell based assay. Percentage of ADCC was determined as specific Cr51 release, calculated using the following formula: % ADCC= ((sample cpm−nonspecific lysis control cpm)/(total lysis control cpm−negative control cpm))×100%. CD47/MSLN κλ bodies induced a dose dependent killing of target cells, which was significantly higher than with the benchmark MSLN mAb.

In FIGS. 5A and 5B, HepG2-MSLN cells were implanted subcutaneously in NOD/SCID mice. Antibody treatment started 15 days later. (FIG. 5A) Tumor growth progression. Tumor growth was measured three times a week and is shown as average tumor volume per group+/−SEM (n=7). Statistical significance was determined at endpoint (D55) using one-way ANOVA followed by multiple comparison test (Tukey's multiple comparison), p-value: *p<0.05, **p<0.01; ns, not significant (FIG. 5B) Tumor Growth Inhibition (TGI). Percentage of TGI as compared to isotype control was determined based on tumor volumes at endpoint, using the following formula: % TGI={1−[(Tt−T0)/(Vt−V0)]}×100; with Tt=median tumor volume of treated at time t; T0=median tumor volume of treated at time 0; Vt=median tumor volume of control at time t and V0=median tumor volume of control at time 0. biAb treatment significantly reduce tumor growth as compared to the control. Moreover, 4 out of 5 biAbs tested proved more efficacious than the MSLN benchmark mAb amatuximab.

In FIGS. 6A and 6B, tumor OVCAR3 and CaOV3 cells, respectively, were implanted subcutaneously in NOD/SCID mice. Antibody treatment started 1 day later. FIG. 6A shows OVCAR3 tumor growth progression. FIG. 6B shows CaOV3 tumor growth progression. Tumor growth was measured three times a week and is shown as average tumor volume per group+/−SEM (n=6 or 7). biAbO38 treatment prevented tumor growth (in contrast to the control IgG).

DETAILED DESCRIPTION

Figure 2A:
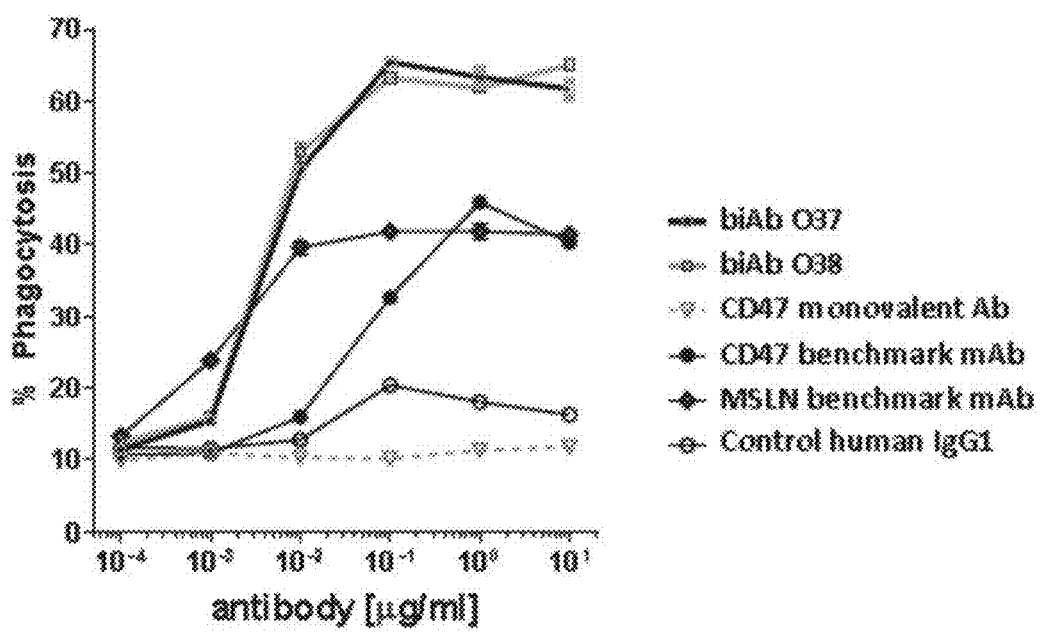
FIGS. 2A-2F are a series of graphs depicting Antibody Dependent Cellular Phagocytosis (ADCP) induced by CD47/MSLN κλ bodies compared to benchmark mAbs targeting CD47 or mesothelin.
Figure 2B:
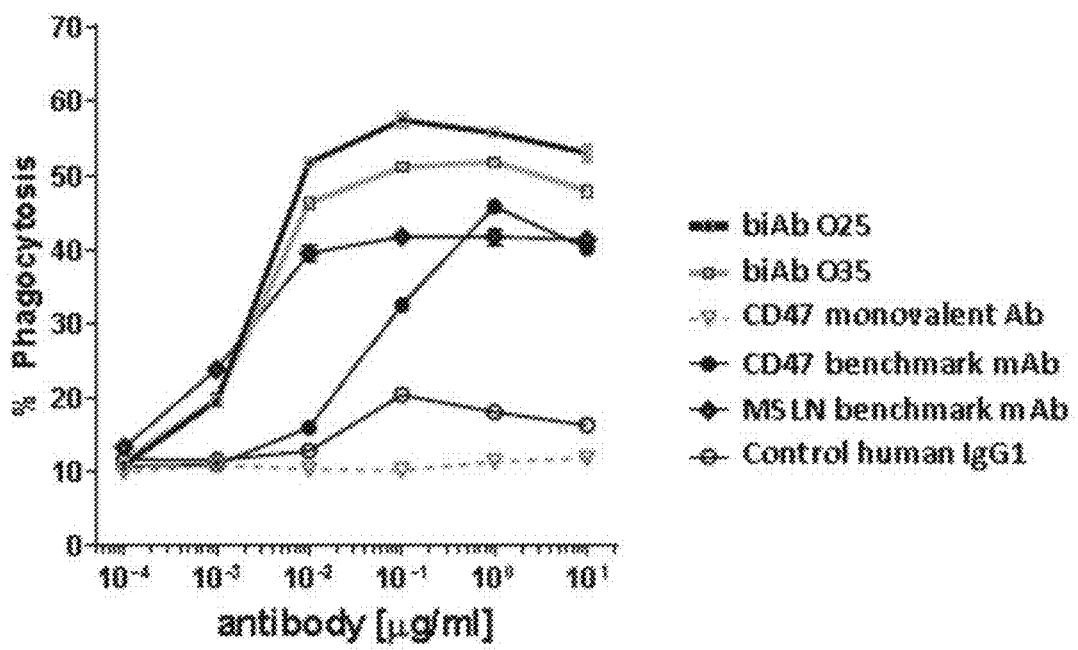
Figure 2C:
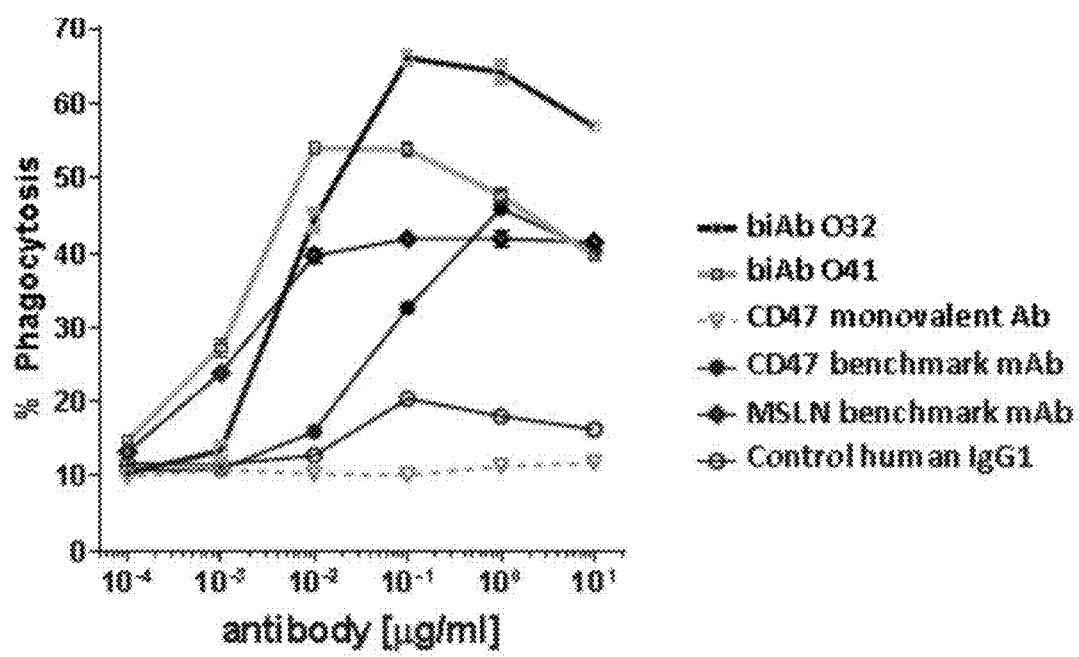
Figure 2D:
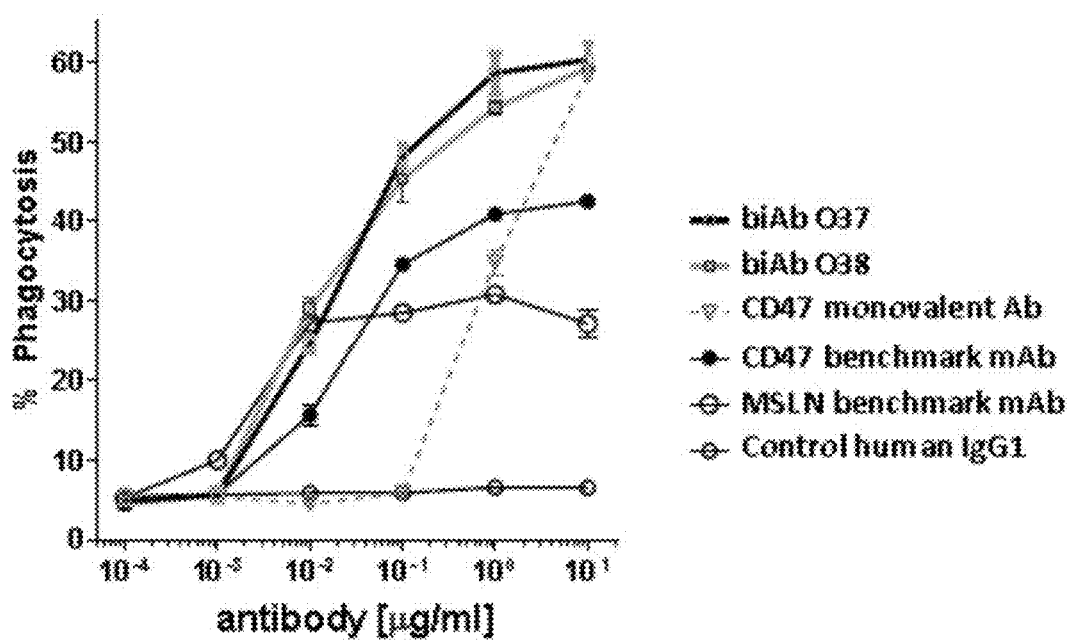
Figure 2E:
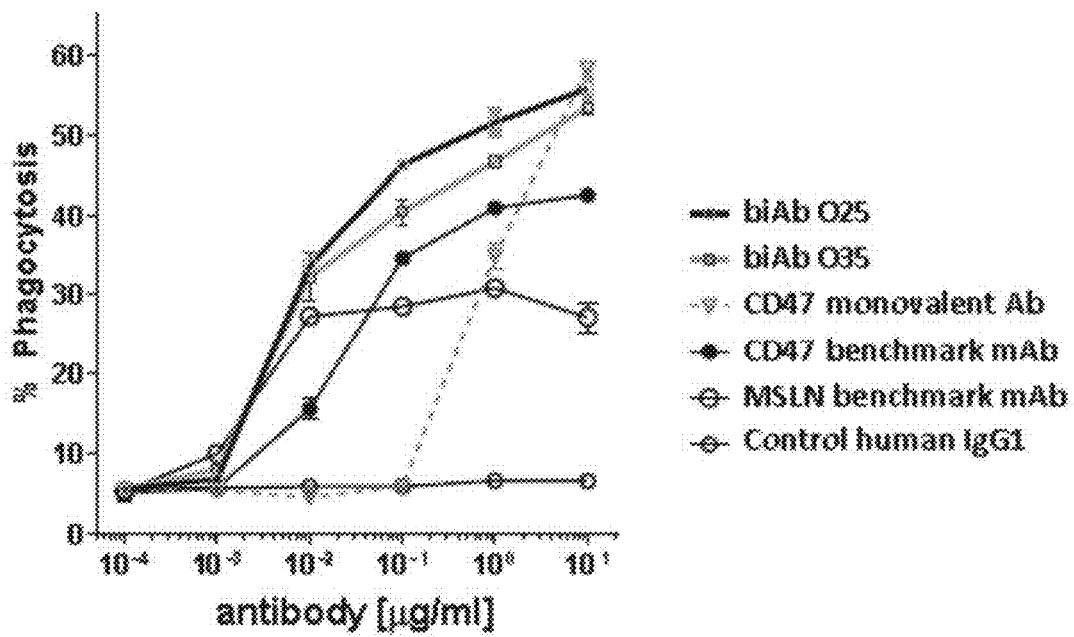
Figure 2F:
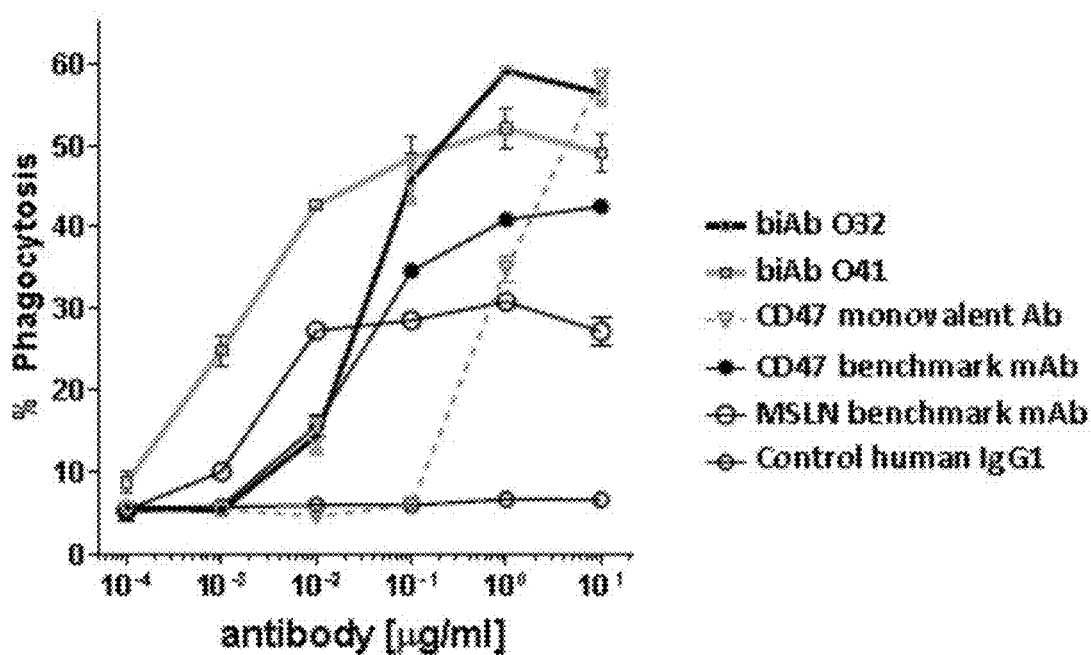
Figure 3A:
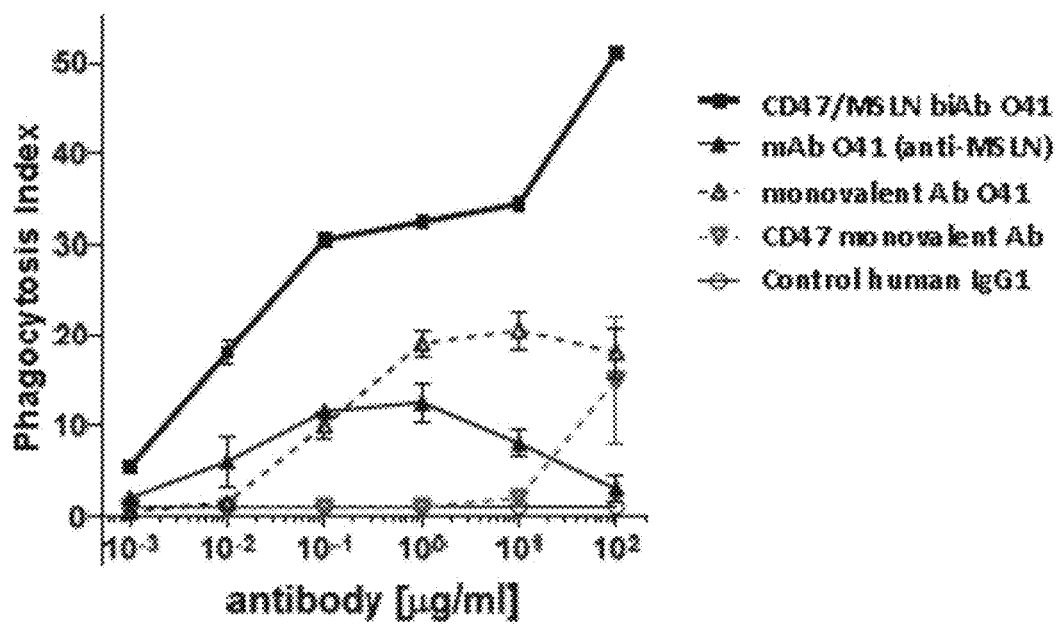
FIGS. 3A-3J are a series of graphs depicting ADCP activity induced by CD47/MSLN κλ bodies compared to the matching anti-MSLN mAbs and monovalent antibodies. Phagocytosis of two target cell lines, NCI-N87 (FIGS. 3A-3E) and Caov-3 (FIGS. 3F-3J) by human macrophages was imaged and quantified with CellInsight CX5 High Content Screening Platform.
Figure 3B:
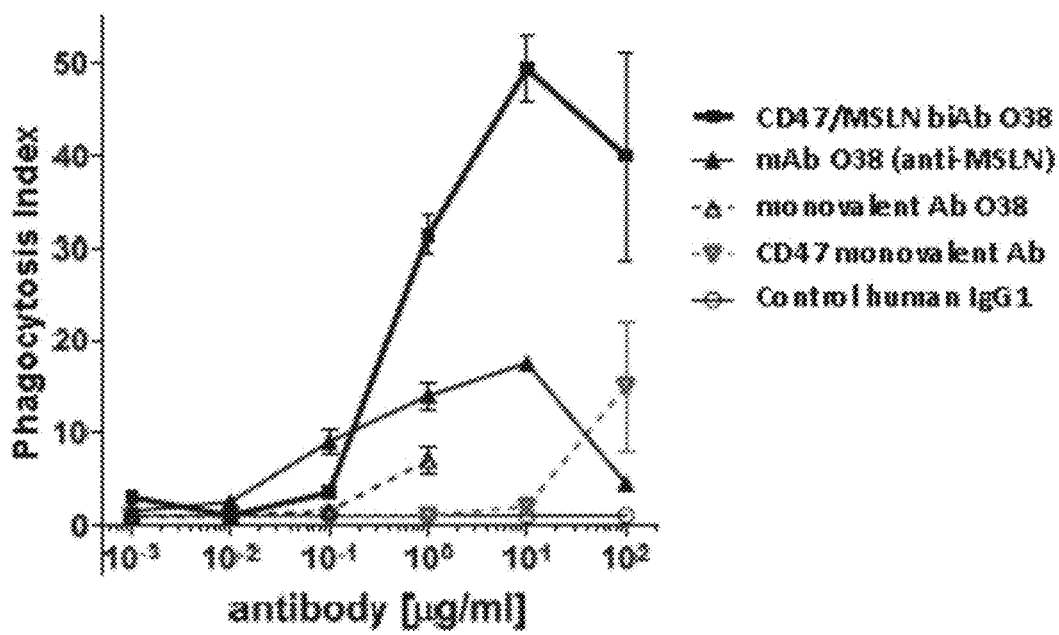
Figure 3C:
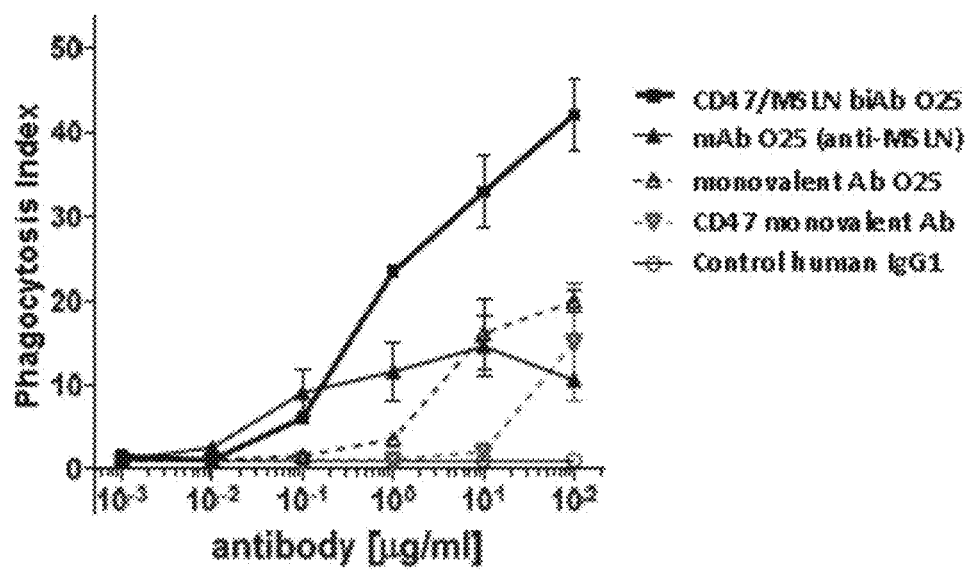
Figure 3D:
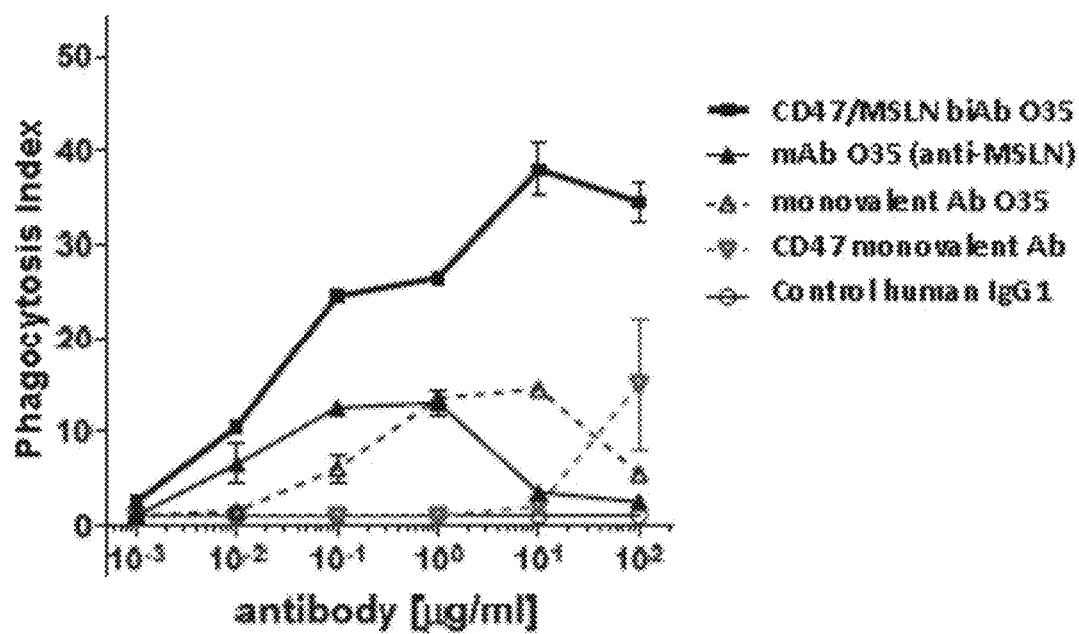
Figure 3E:
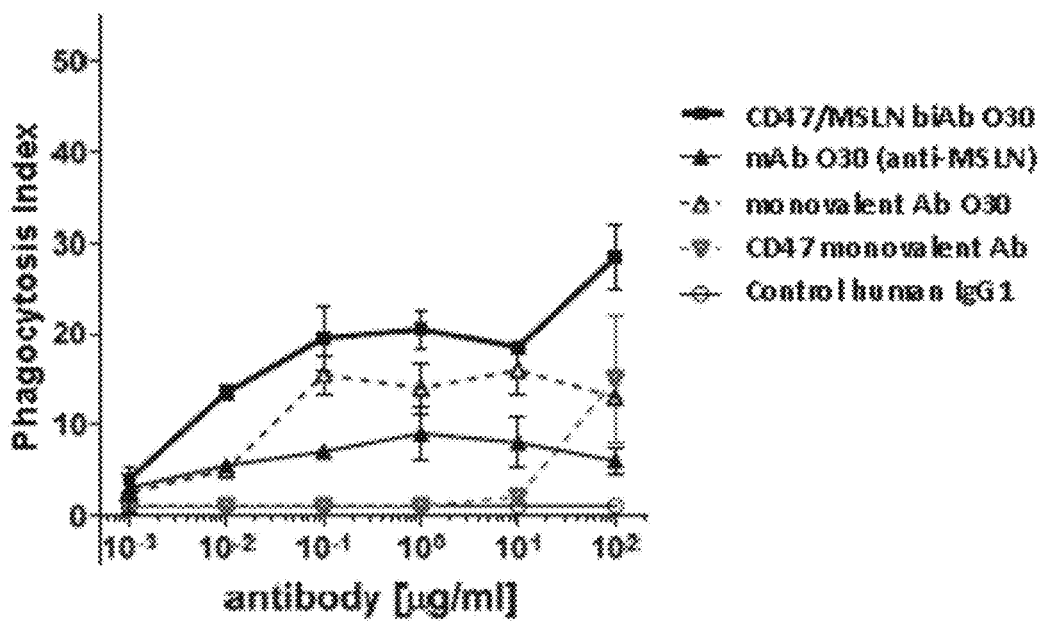
Figure 3F:
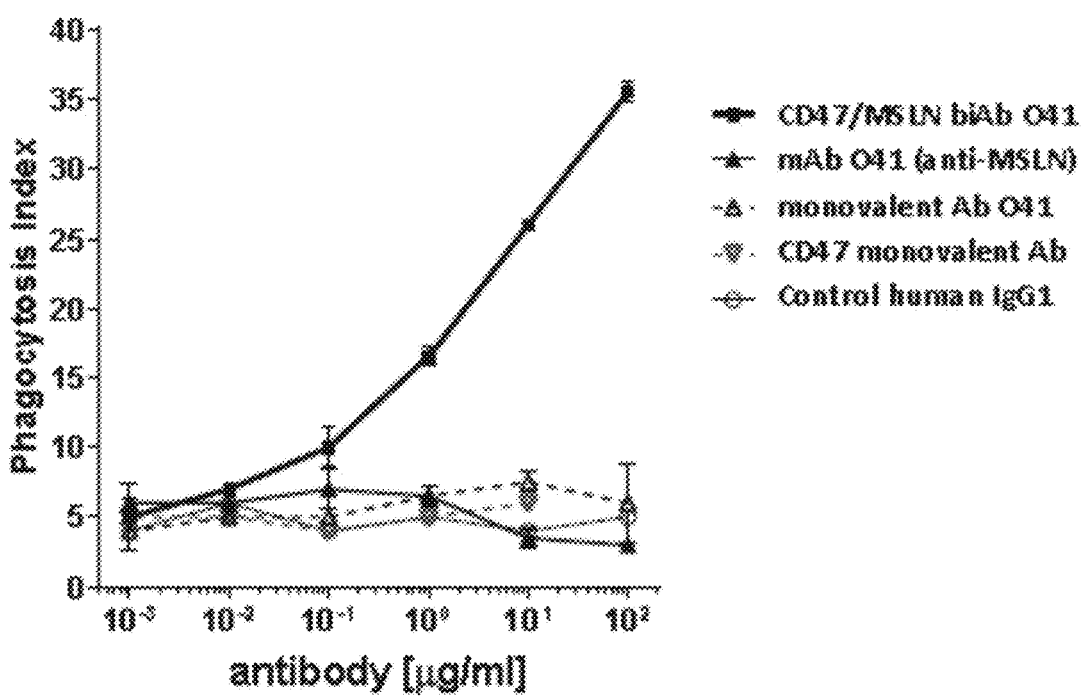
Figure 3G:
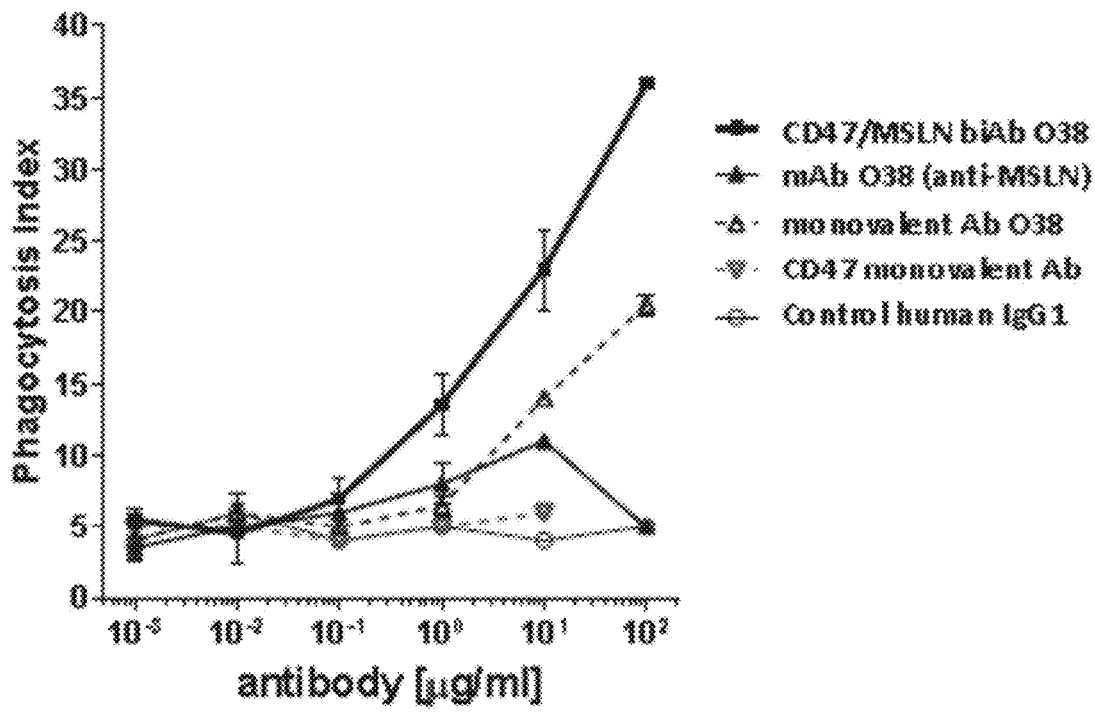
Figure 3H:
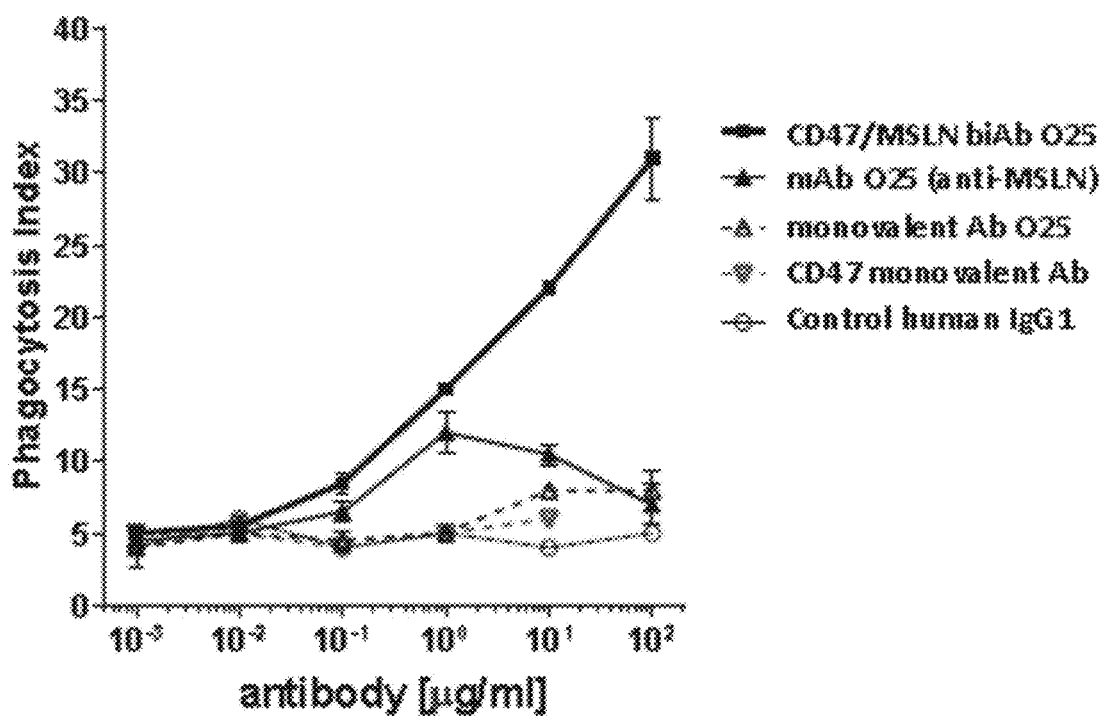
Figure 3I:
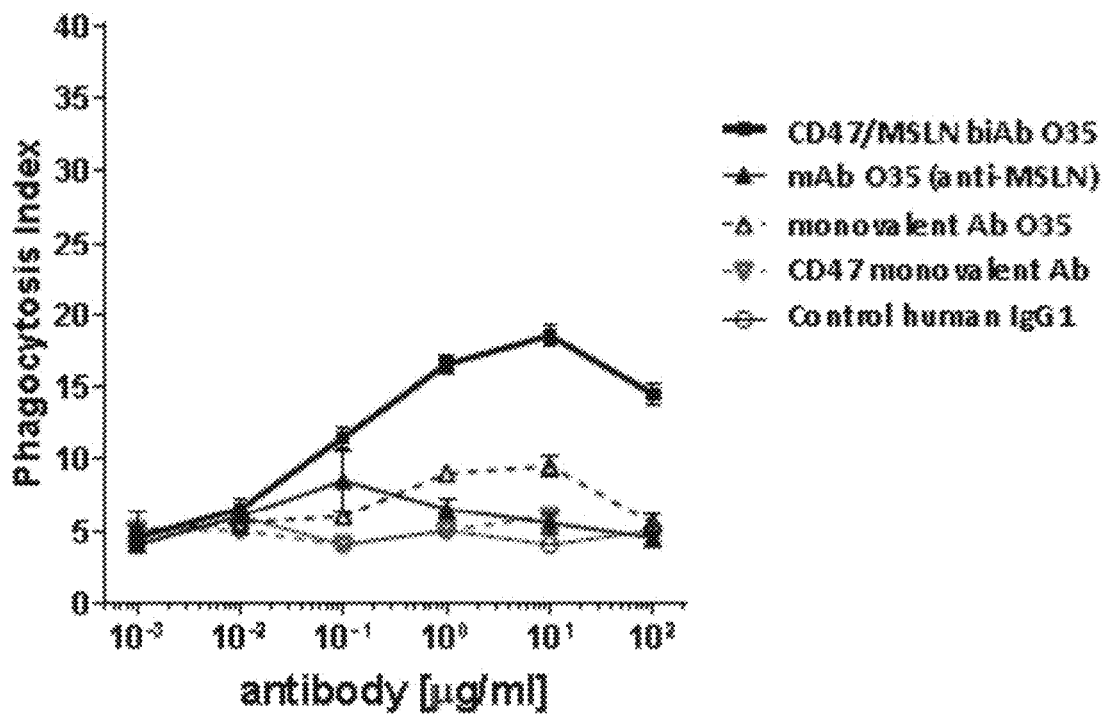
Figure 3J:
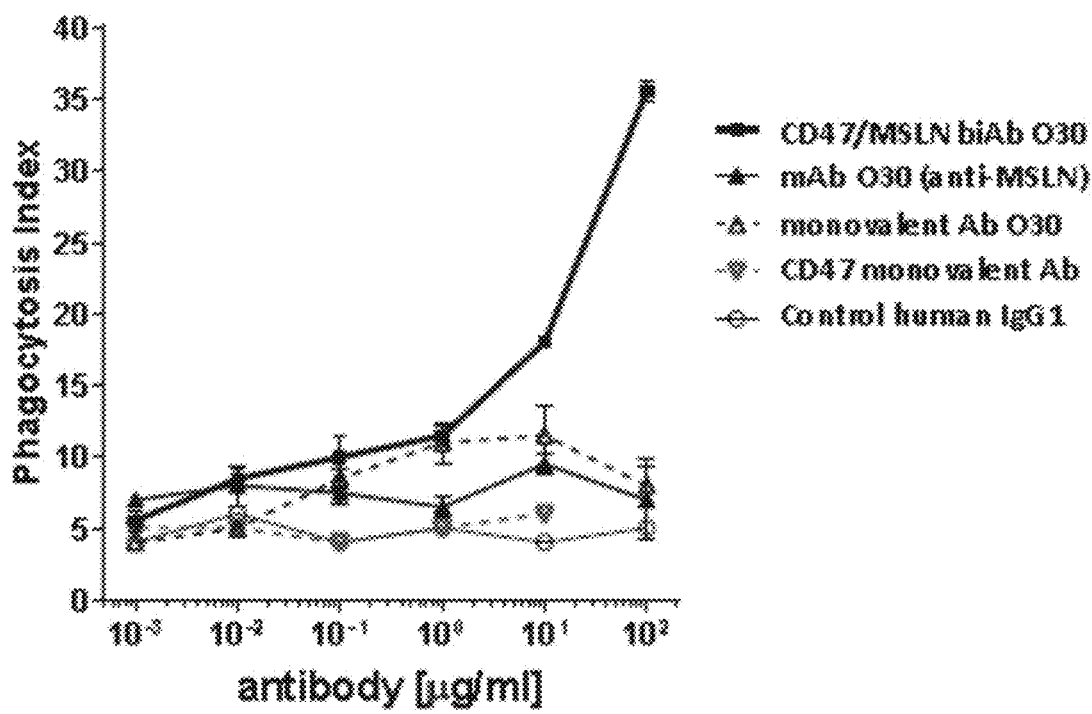

CD47 or Integrin-Associated-Protein (IAP) is a ubiquitous 50 kDa transmembrane glycoprotein with multiple functions in cell-cell communication. It interacts with multiple ligands, such as, for example, integrins, and/or SIRPα. In the context of the innate immune system, CD47 functions as a marker of self, transmitting an inhibitory "don't kill me" signal through binding to SIRPα expressed by myeloid cells, such as macrophages, neutrophils, and dendritic cells. The role of widespread expression of CD47 in the physiological situation is therefore to protect healthy cells against the elimination by the innate immune system (Oldenborg P A, et al., CD47-Signal Regulatory Protein a (Sirpα) Regulates Fcγ and Complement Receptor-Mediated Phagocytosis, J Exp Med. 2001 Apr. 2; 193(7):855-62; Manias Olsson, Role of the CD47/SIRPα-interaction in regulation of macrophage phagocytosis, Department of Integrative Medical Biology, Section for Histology and Cell Biology, Umeå University, Umeå, Sweden, Thesis; Oldenborg P A., Role of CD47 in erythroid cells and in autoimmunity, Leuk Lymphoma. 2004 July; 45(7):1319-27; Oldenborg P A, et al., Role of CD47 as a Marker of Self on Red Blood Cells., Science. 2000 Jun. 16; 288(5473):2051-4; Brown E J, Frazier W A., integrin-associated protein (CD47) and its ligands., Trends Cell Biol. 2001 March; 11(3):130-5).

Tumor cells hijack this immunosuppressive mechanism by overexpressing CD47, which efficiently helps them to escape immune surveillance and killing by innate immune cells. (Majeti R, Chet al., CD47 is an adverse prognostic factor and therapeutic antibody target on human acute myeloid leukemia stem cells, Cell. 2009 Jul. 23; 138(2):286-99; S. Jaiswal et al., CD47 is upregulated on circulating hematopoietic stem cells and leukemia cells to avoid phagocytosis., Cell. 2009 Jul. 23; 138(2):271-85). CD47 expression is upregulated in most human cancers (e.g., NHL, AML, breast, colon, glioblastoma, glioma, ovarian, bladder and prostate cancers) and increased levels of CD47 expression clearly correlate with aggressive disease and poor survival. (Majeti R, et al., Cell. 2009 Jul. 23; 138(2):286-99; S. Jaiswal et al., Cell. 2009 Jul. 23; 138(2):271-85; Willingham S B, et al., The CD47-signal regulatory protein alpha (SIRPα) interaction is a therapeutic target for human solid tumors, Proc Natl Acad Sci USA. 2012 Apr. 24; 109(17): 6662-7; Chao M P, et al., Therapeutic antibody targeting of CD47 eliminates human acute lymphoblastic leukemia., Cancer Res. 2011 Feb. 15; 71(4):1374-84).

The widespread expression of CD47 in healthy tissues brings the question of treatment safety and efficacy: First, targeting CD47 with a neutralizing monoclonal antibody (Mab) could affect healthy cells, resulting in severe toxicities as shown in preclinical studies with mice and cynomolgus monkeys (Willingham S B, et al., Proc Natl Acad Sci USA. 2012 Apr. 24; 109(17):6662-7; Weiskopf K, et al., Engineered SIRPα Variants as Immunotherapeutic Adjuvants to Anticancer Antibodies, Science. 2013 Jul. 5; 341 (6141):88-91). Second, even if severe toxicities could be avoided or mitigated by using alternative formats (Weiskopf K, et al., Science. 2013 Jul. 5; 341(6141):88-91), broad expression of CD47 could still cause a rapid elimination of CD47-binding molecules through target-mediated drug disposition resulting in poor pharmacokinetics and decreased efficacy.

Mesothelin (MSLN) is a 40 kDa glycosylphosphatidylinositol (GPI)-linked cell surface glycoprotein that is generated proteolytically from a 71 kDa precursor. In normal tissues, mesothelin is expressed—at relatively low levels—only in mesothelial cells lining serosal membranes such as the pleura, peritoneum, and pericardium. The normal physiologic function of mesothelin remains unclear but it seems dispensable, since mesothelin deficient mice grow and reproduce normally and display no obvious abnormalities.

In contrast to normal tissues, mesothelin is highly expressed in several types of solid tumors such as malignant mesothelioma, ovarian cancer, pancreatic adenocarcinoma, lung adenocarcinoma, as well as endometrial, biliary gastric and prostate cancers. Tumor mesothelin expression has often been correlated with increased tumor aggressiveness and poor clinical outcome. Mesothelin binding to ovarian cancer antigen MUC16 (CA-125) has been shown to mediate cell-to-cell adhesion, possibly contributing metastatic dissemination. In addition, mesothelin-mediated intracellular signaling was reported to promote tumor cell proliferation, as well as resistance to chemotherapy and to anoikis (programmed cell death resulting from loss of normal cell-matrix interactions).

Similar to most other GPI-anchored proteins, mesothelin is shed from the membrane, and soluble mesothelin has been reported in sera of tumor patients. Soluble mesothelin is therefore a useful biomarker, for diagnosis of mesothelin-positive tumors, but also for monitoring disease progression and response to treatment. Soluble mesothelin is also considered as a negative prognostic biomarker for patients with ovarian cancer, lung or pancreatic adenocarcinoma, and triple-negative breast cancer. Last but not least, serum mesothelin levels are a predictive biomarker in mesothelioma, as they have been found to positively correlate with therapeutic responses to mesothelin-targeting therapies.

Most tumor-associated antigens used to therapeutically target solid tumors are also expressed in essential normal tissues. In contrast, expression of mesothelin is generally low-level and limited to mesothelial cells (which seem dispensable). On the other hand, cell-surface expression of mesothelin is high in many solid tumors, which makes mesothelin a particularly attractive target of therapeutic intervention. Accordingly, numerous mesothelin-directed therapies, using monoclonal antibodies, recombinant immunotoxins, antibody-drug conjugates, cancer vaccines, and chimeric antigen receptor T cells, are currently under development, including clinical evaluation at late stage trials for MPM and pancreatic adenocarcinoma.

The invention also provides bispecific antibodies that recognize CD47 and mesothelin.

The bispecific antibodies of the invention allow for simultaneous binding of the two antibody arms to two antigens on the surface of the cell (termed co-engagement), which results in additive or synergistic increase of affinity due to avidity mechanism. As a consequence, co-engagement confers high selectivity towards cells expressing both antigens as compared to cells that express just one single antigen. In addition, the affinities of the two arms of a bispecific antibody to their respective targets can be set up in a way that binding to target cells is principally driven by one of the antibody arms. In some embodiments, the bispecific antibody includes a first arm that binds CD47 and a second arm that binds mesothelin, where the second arm binds to mesothelin with high affinity, and the first arm binds to CD47 with low affinity, i.e., an affinity that is sufficient to inhibit CD47/SIRPα upon mesothelin co-engagement. This design allows the bispecific antibodies of the invention to preferentially inhibit CD47 in cancer versus normal cells. In the examples provided herein, a bispecific antibody with a first arm that binds CD47 with low affinity and a second arm that binds MSLN with high affinity (termed a CD47×MSLN bispecific) allow preferential inhibition of CD47 in cancer versus normal cells. Besides the two antigen-binding arms, the CD47×MSLN bispecific antibody requires a functional Fc portion to recruit macrophages and/or other immune effector cells. A fully human bispecific IgG format (such as the κλ-body format described herein) is well suited for the generation of dual targeting CD47×MSLN bispecific antibodies. The ability of dual targeting bispecific antibodies to co-engage CD47 and MSLN results in efficient and selective cancer cell killing mediated by the CD47×MSLN bispecific antibody, as demonstrated in the ADCC and ADCP experiments provided herein.

Exemplary bispecific antibodies of the invention in which at least one binding site is specific for CD47 and a second binding site is specific for mesothelin include, for example, bispecific antibodies in which the first arm comprises the 5A3 antibody, the 5A3M4 antibody, the 5A3M3 antibody, the 5A3M5 antibody, the KE8 antibody, the KE8-P6H5 antibody (also referred to herein as KE8H5), the KE8-P3B2 antibody (also referred to herein as KE8B2), the KE8-P2A2 antibody (also referred to herein as KE8A25), the KE8F2 antibody, the KE8G2 antibody, the KE84G9 antibody, the KE81G9 antibody, the KE81A3 antibody, the KE8E8 antibody, the KE8G6 antibody, the KE8H3 antibody, the KE8C7 antibody, the KE8A4 antibody, the KE8A8 antibody, the KE8G11 antibody, the KE8B7 antibody, the KE8F1 antibody, the KE8C4 antibody, the KE8A3 antibody, the KE86G9 antibody, the KE8H6 antibody, the KA3 antibody, the KA3-P5G2 antibody (also referred to herein as KA3G2), the KA3-P1A3 antibody (also referred to herein as KA3A3), the KA3-P5C5 antibody (also referred to herein as KA3C5), the KA3H8 antibody, the KA3B2 antibody, the KA3A2 antibody, the KA3D3 antibody, the KA3H3 antibody, the KC4 antibody, the KC4-P1G11KC4-P4C11 antibody, the KC4-P6B1KC4-P4F4 antibody, and the KC4-P2E2 antibody (also referred to herein as KC4E2), the KC4 antibody, the KC4F4 antibody, the KC4A1 antibody, the KC4C11 antibody, the KC4E10 antibody, the KC4B1 antibody, the KC4C3 antibody, the KC4A4 antibody, the KC4G11 antibody, or the KC4G9 antibody, as well as immunologically active and/or antigen-binding fragments thereof, and in which the second arm comprises the O25 antibody, the O30 antibody, the O32 antibody, the O35 antibody, the O37 antibody, the O38 antibody, or the O41 antibody, as well as immunologically active and/or antigen-binding fragments thereof.

In some embodiments, exemplary bispecific antibodies of the invention that include at least a first arm that binds CD47 include a combination of heavy chain and light chain complementarity determining regions (CDRs) selected from the CDR sequences shown in Tables 1, 2 and 3, where the CDRs shown in Tables 1, 2 and 3 are defined according to the IMGT nomenclature.

In some embodiments, exemplary bispecific antibodies of the invention that include at least a first arm that binds CD47 include the combination of heavy chain CDR sequences from Table 1 and two sets of light chain CDRs selected from the CDRL1, CDRL2 and CDRL3 sequences shown in Tables 2 and 3.

In some embodiments, exemplary bispecific antibodies of the invention that include at least a first arm that binds CD47 include the combination of heavy chain CDR sequences from Table 1 and a first set of light chain CDRs selected from the CDRL1, CDRL2 and CDRL3 sequences shown in Table 2 and a second set of light chain CDRs selected from the CDRL1, CDRL2 and CDRL3 sequences shown in Table 3.

In some embodiments, exemplary bispecific antibodies of the invention that include a first arm that binds CD47 and a second arm that binds MSLN, wherein the first arm includes the combination of heavy chain complementarity determining regions (CDRs) shown in Table 1 and a combination of the light chain CDRs selected from the CDR sequences shown in Table 2, and wherein the second arm includes the combination of heavy chain complementarity determining regions (CDRs) shown in Table 1 and a combination of the light chain CDRs selected from the CDR sequences shown in Table 4.

TABLE 1

Common Heavy Chain CDRs

| CDRH1 | CDRH2 | CDRH3 |
|---|---|---|
| GFTFSSYA (SEQ ID NO: 225) | ISGSGGST (SEQ ID NO: 226) | AKSYGAFDY (SEQ ID NO: 227) |

TABLE 2

Anti-CD47 Kappa Light Chain CDRs

| CDRL1 | CDRL2 | CDRL3 |
|---|---|---|
| QDINKY (SEQ ID NO: 228) | AAS (SEQ ID NO: 242) | QQKHPRGPRT (SEQ ID NO: 246) |
| QDINRY (SEQ ID NO: 229) | GAS (SEQ ID NO: 243) | QQFHKRAPQT (SEQ ID NO: 247) |
| QNIGKY (SEQ ID NO: 230) | NAS (SEQ ID NO: 244) | QQFHKRRPQT (SEQ ID NO: 248) |
| QSIARY (SEQ ID NO: 231) | SAS (SEQ ID NO: 245) | QQFHKRSPQT (SEQ ID NO: 249) |
| QSIASY (SEQ ID NO: 232) | | QQKHPRAPRT (SEQ ID NO: 250) |

TABLE 2-continued

Anti-CD47 Kappa Light Chain CDRs

| CDRL1 | CDRL2 | CDRL3 |
|---|---|---|
| QSIDKY (SEQ ID NO: 233) | | QQKHPRSPRT (SEQ ID NO: 251) |
| QSIDRY (SEQ ID NO: 234) | | QQKHPRYPRT (SEQ ID NO: 252) |
| QSIGKY (SEQ ID NO: 235) | | QQKHPRNPRT (SEQ ID NO: 253) |
| QSIGRY (SEQ ID NO: 236) | | QQMHPRAPKT (SEQ ID NO: 254) |
| QSINRY (SEQ ID NO: 237) | | QQMHPRGPKT (SEQ ID NO: 255) |
| QSISKY (SEQ ID NO: 238) | | QQMHPRSPKT (SEQ ID NO: 256) |
| QSISRY (SEQ ID NO: 239) | | QQRHPRAPRT (SEQ ID NO: 257) |
| QSISSY (SEQ ID NO: 240) | | QQRHKRSPQT (SEQ ID NO: 258) |
| QSIAKY (SEQ ID NO: 241) | | QQRHPRGPRT (SEQ ID NO: 259) |
| | | QQRHPRGPST (SEQ ID NO: 260) |
| | | QQRHPRGPTT (SEQ ID NO: 261) |

TABLE 3

Anti-CD47 Lambda Light Chain CDRs

| CDRL1 | CDRL2 | CDRL3 |
|---|---|---|
| SSDVGGYNY (SEQ ID NO: 262) | ENS (SEQ ID NO: 273) | SSYDWWFRPKV (SEQ ID NO: 281) |
| SSDVERKNY (SEQ ID NO: 263) | ESS (SEQ ID NO: 274) | |
| SSDVRANNY (SEQ ID NO: 264) | EVS (SEQ ID NO: 275) | |
| SSDVYYNKY (SEQ ID NO: 265) | KDS (SEQ ID NO: 276) | |
| SSDVGKANY (SEQ ID NO: 266) | KNS (SEQ ID NO: 277) | |
| SSDVRGNNY (SEQ ID NO: 267) | KSS (SEQ ID NO: 278) | |
| SSDVSARNY (SEQ ID NO: 268) | KTS (SEQ ID NO: 279) | |
| SSDVNSANY (SEQ ID NO: 269) | QDS (SEQ ID NO: 280) | |
| SSDVRAANY (SEQ ID NO: 270) | | |
| SSDVRRANY (SEQ ID NO: 271) | | |
| SSDVNNTNY (SEQ ID NO: 272) | | |

TABLE 4

Anti-CD47 Lambda Light Chain CDRs

| CDRL1 | CDRL2 | CDRL3 |
|---|---|---|
| KIGHRA (SEQ ID NO: 282) | YTY (SEQ ID NO: 288) | QVWDASRRDANVV (SEQ ID NO: 294) |
| SGISVKDYR (SEQ ID NO: 283) | YKSNSDM (SEQ ID NO: 289) | MIWHHGHGTSLV (SEQ ID NO: 295) |
| SSNIAHGP (SEQ ID NO: 284) | ATN (SEQ ID NO: 290) | AAYDLTGWFAYAV (SEQ ID NO: 296) |
| SGINVKDYR (SEQ ID NO: 285) | YKSESDK (SEQ ID NO: 291) | MIWHKDREGHAFV (SEQ ID NO: 297) |
| SGINVRDYR (SEQ ID NO: 286) | YKSASDK (SEQ ID NO: 292) | MIWHHDSEGHAFV (SEQ ID NO: 298) |
| SDIRVRDYR (SEQ ID NO: 287) | YKTDSDK (SEQ ID NO: 293) | MIWHRTTGTSLV (SEQ ID NO: 299) |
| | | QVWDWYSEGGVV (SEQ ID NO: 300) |

Each of the exemplary anti-CD47, anti-MSLN, monovalent and bispecific antibodies described herein include a common heavy chain (HC), one kappa chain or one lambda chain for anti-CD47 and anti-MSLN antibodies, one kappa and one lambda light chains (LC) for monovalent and bispecific antibodies, as shown in the amino acid and corresponding nucleic acid sequences listed below. Each of the exemplary anti-CD47, anti-MSLN, monovalent and bispecific antibodies described below includes a common variable heavy domain (VH), one kappa variable light domain or one lambda variable light domain for anti-CD47 and anti-MSLN antibodies, one kappa and one lambda variable light domains (VL) for monovalent and bispecific antibodies, as shown in the amino acid and corresponding nucleic acid sequences listed below.

While antibody sequences below are provided herein as examples, it is to be understood that these sequences can be used to generate bispecific antibodies using any of a variety of art-recognized techniques. Examples of bispecific formats include but are not limited to bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46.) or knob-into-hole (Ridgway J B et al., Protein Eng. 1996 9(7):617-21.) or other sets of mutations preventing homodimer formation (Von Kreudenstein T S et al., 2013 MAbs. 5(5):646-54.); fragment based bispecific formats such as tandem scFv (such asBiTEs) (Wolf E et al., 2005 Drug Discov. Today 10(18):1237-44.); bispecific tetravalent antibodies (Portner L M et al., 2012 Cancer Immunol Immunother. 61(10):1869-75.); dual affinity retargeting molecules (Moore P A et al., 2011 Blood. 117(17):4542-51), diabodies (Kontermann R E et al., Nat Biotechnol. 1997 15(7):629-31).

The exemplary anti-CD47, anti-MSLN, monovalent and bispecific antibodies include a common heavy chain (SEQ ID NO: 2) encoded by the nucleic acid sequence shown in SEQ ID NO: 1.

>COMMON-HC-NT (SEQ ID NO: 1)

GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

GGTGCTTTTGACTACTGGGGCCAGGGAACCCTGGTCACAGTCTCGAGCGC

CTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACAGTCTCGTGGAACTCAGGAGCCCTGACCAGCGGCGTGCA

CACCTTCCCGGCTGTCCTACAGTCCTCAGGACTCTACTCCCTCAGCAGCG

TGGTGACTGTGCCCTCCAGCAGCTTGGGCACCCAGACCTACATCTGCAAC

GTGAATCACAAGCCCAGCAACACCAAGGTGGACAAGAGAGTTGAGCCCAA

ATCTTGTGACAAAACTCACACATGCCCACCGTGCCCAGCACCTGAACTCC

TGGGGGGACCGTCAGTCTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAAGGGCAGCCCCGAGAACCACAGGTGTATACCCTG

CCCCCATCTCGGGAGGAGATGACCAAGAACCAGGTCAGCCTGACTTGCCT

GGTCAAAGGCTTCTATCCCAGCGACATCGCCGTGGAGTGGGAGAGCAACG

GGCAGCCGGAGAACAACTACAAGACCACGCCTCCCGTGCTGGACTCCGAC

GGCTCCTTCTTCCTCTATAGCAAGCTCACCGTGGACAAGTCCAGGTGGCA

GCAGGGGAACGTCTTCTCATGCTCCGTGATGCATGAGGCTCTGCACAACC

ACTACACGCAGAAGAGCCTCTCCCTGTCTCCGGGTTAA

>COMMON-HC-AA (SEQ ID NO: 2)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSY

GAFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG

The anti-CD47, anti-MSLN, monovalent and bispecific antibodies include a common variable heavy domain (SEQ ID NO: 114) encoded by the nucleic acid sequence shown in SEQ ID NO: 113.

>COMMON-VH-NT (SEQ ID NO: 113)
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

GGTGCTTTTGACTACTGGGGCCAGGGAACCCTGGTCACAGTCTCGAGC

>COMMON-VH-AA (SEQ ID NO: 114)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSY

GAFDYWGQGTLVTVSS

Anti-CD47 Antibodies

The 5A3 antibody includes a common heavy chain (SEQ ID NO: 2) encoded by the nucleic acid sequence shown in SEQ ID NO: 1 and includes a kappa light chain (SEQ ID NO: 4) encoded by the nucleic acid sequence shown in SEQ ID NO: 3.

>5A3-LC-NT (SEQ ID NO: 3)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCGGGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>5A3-LC-AA (SEQ ID NO: 4)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The 5A3 antibody includes a common variable heavy domain (SEQ ID NO: 114) encoded by the nucleic acid sequence shown in SEQ ID NO: 113 and includes a kappa variable light domain (SEQ ID NO: 116) encoded by the nucleic acid sequence shown in SEQ ID NO: 115.

```
>5A3-VL-NT
                                          (SEQ ID NO: 115)
GACATCCAGATGACCCAGTCTCCATCCTCCCTGTCTGCATCTGTAGGAGA
CAGAGTCACCATCACTTGCCAGGCGAGTCAGGACATTAATAAGTATTTAA
ATTGGTATCAGCAGAAACCAGGGAAAGCCCCTAAGCTCCTGATCTACGGT
GCATCCAGGTTGGAAACAGGGGTCCCATCAAGGTTCAGTGGAAGTGGATC
TGGGACAGATTTTACTTTCACCATCAGCAGCCTGCAGCCTGAAGATATTG
CAACATATTACTGTCAGCAGAAGCACCCCCGGGGGCCGAGGACCTTCGGC
CAAGGGACCAAGGTGGAAATCAAA

>5A3-VL-AA
                                          (SEQ ID NO: 116)
DIQMTQSPSSLSASVGDRVTITCQASQDINKYLNWYQQKPGKAPKLLIYG
ASRLETGVPSRFSGSGSGTDFTFTISSLQPEDIATYYCQQKHPRGPRTFG
QGTKVEIK
```

```
>5A3-M4-VL-NT
                                          (SEQ ID NO: 117)
GACATCCAGATGACCCAGTCTCCATCCTCCCTGTCTGCATCTGTAGGAGA
CAGAGTCACCATCACTTGCCAGGCGAGTCAGGACATTAATAAGTATTTAA
ATTGGTATCAGCAGAAACCAGGGAAAGCCCCTAAGCTCCTGATCTACGGT
GCATCCAGGTTGGAAACAGGGGTCCCATCAAGGTTCAGTGGAAGTGGATC
TGGGACAGATTTTACTTTCACCATCAGCAGCCTGCAGCCTGAAGATATTG
CAACATATTACTGTCAGCAGAAGCACCCCCGGAACCCGAGGACCTTCGGC
CAAGGGACCAAGGTGGAAATCAAA

>5A3-M4-VL-AA
                                          (SEQ ID NO: 118)
DIQMTQSPSSLSASVGDRVTITCQASQDINKYLNWYQQKPGKAPKLLIYG
ASRLETGVPSRFSGSGSGTDFTFTISSLQPEDIATYYCQQKHPRNPRTFG
QGTKVEIK
```

The 5A3-M4 antibody includes a common heavy chain (SEQ ID NO: 2) encoded by the nucleic acid sequence shown in SEQ ID NO: 1 and includes a kappa light chain (SEQ ID NO: 6) encoded by the nucleic acid sequence shown in SEQ ID NO: 5.

The 5A3-M3 antibody includes a common heavy chain (SEQ ID NO: 2) encoded by the nucleic acid sequence shown in SEQ ID NO: 1 and includes a kappa light chain (SEQ ID NO: 8) encoded by the nucleic acid sequence shown in SEQ ID NO: 7.

```
>5A3-M4-LC-NT
                                          (SEQ ID NO: 5)
GACATCCAGATGACCCAGTCTCCATCCTCCCTGTCTGCATCTGTAGGAGA
CAGAGTCACCATCACTTGCCAGGCGAGTCAGGACATTAATAAGTATTTAA
ATTGGTATCAGCAGAAACCAGGGAAAGCCCCTAAGCTCCTGATCTACGGT
GCATCCAGGTTGGAAACAGGGGTCCCATCAAGGTTCAGTGGAAGTGGATC
TGGGACAGATTTTACTTTCACCATCAGCAGCCTGCAGCCTGAAGATATTG
CAACATATTACTGTCAGCAGAAGCACCCCCGGAACCCGAGGACCTTCGGC
CAAGGGACCAAGGTGGAAATCAAACGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGTTAA

>5A3-M4-LC-AA
                                          (SEQ ID NO: 6)
DIQMTQSPSSLSASVGDRVTITCQASQDINKYLNWYQQKPGKAPKLLIYG
ASRLETGVPSRFSGSGSGTDFTFTISSLQPEDIATYYCQQKHPRNPRTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
```

```
>5A3-M3-LC-NT
                                          (SEQ ID NO: 7)
GACATCCAGATGACCCAGTCTCCATCCTCCCTGTCTGCATCTGTAGGAGA
CAGAGTCACCATCACTTGCCAGGCGAGTCAGTCCATTAGTAGTTATTTAA
ATTGGTATCAGCAGAAACCAGGGAAAGCCCCTAAGCTCCTGATCTACGCT
GCATCCTCGTTGGAAACAGGGGTCCCATCAAGGTTCAGTGGAAGTGGATC
TGGGACAGATTTTACTTTCACCATCAGCAGCCTGCAGCCTGAAGATATTG
CAACATATTACTGTCAGCAGAAGCACCCCCGGGGGCCGAGGACCTTCGGC
CAAGGGACCAAGGTGGAAATCAAACGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGTTAA

>5A3-M3-LC-AA
                                          (SEQ ID NO: 8)
DIQMTQSPSSLSASVGDRVTITCQASQSISSYLNWYQQKPGKAPKLLIYA
ASSLETGVPSRFSGSGSGTDFTFTISSLQPEDIATYYCQQKHPRGPRTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
```

The 5A3-M4 antibody includes a common variable heavy domain (SEQ ID NO: 114) encoded by the nucleic acid sequence shown in SEQ ID NO: 113 and includes a kappa variable light domain (SEQ ID NO: 118) encoded by the nucleic acid sequence shown in SEQ ID NO: 117.

The 5A3-M3 antibody includes a common variable heavy domain (SEQ ID NO: 114) encoded by the nucleic acid sequence shown in SEQ ID NO: 113 and includes a kappa variable light domain (SEQ ID NO: 120) encoded by the nucleic acid sequence shown in SEQ ID NO: 119.

>5A3-M3-VL-NT (SEQ ID NO: 119)

GACATCCAGATGACCCAGTCTCCATCCTCCCTGTCTGCATCTGTAGGAGA

CAGAGTCACCATCACTTGCCAGGCGAGTCAGTCCATTAGTAGTTATTTAA

ATTGGTATCAGCAGAAACCAGGGAAAGCCCCTAAGCTCCTGATCTACGCT

GCATCCTCGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCCGGGGGCCGAGGACCTTCGGC

CAAGGGACCAAGGTGGAAATCAAA

>5A3-M3-VL-AA (SEQ ID NO: 120)

DIQMTQSPSSLSASVGDRVTITCQASQSISSYLNWYQQKPGKAPKLLIYA

ASSLETGVPSRFSGSGSGTDFTFTISSLQPEDIATYYCQQKHPRGPRTFG

QGTKVEIK

The 5A3-M5 antibody includes a common heavy chain (SEQ ID NO: 2) encoded by the nucleic acid sequence shown in SEQ ID NO: 1 and includes a kappa light chain (SEQ ID NO: 10) encoded by the nucleic acid sequence shown in SEQ ID NO: 9.

>5A3-M5-LC-NT (SEQ ID NO: 9)

GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCCGGTACCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>5A3-M5-LC-AA (SEQ ID NO: 10)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRYPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The 5A3-M5 antibody includes a common variable heavy domain (SEQ ID NO: 114) encoded by the nucleic acid sequence shown in SEQ ID NO: 113 and includes a kappa variable light domain (SEQ ID NO: 122) encoded by the nucleic acid sequence shown in SEQ ID NO: 121.

>5A3-M5-VL-NT (SEQ ID NO: 121)

GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCCGGTACCCGAGGACCTTCGGC

CAAGGGACCAAGGTGGAAATCAAA

>5A3-M5-VL-AA (SEQ ID NO: 122)

DIQMTQSPSSLSASVGDRVTITCQASQDINKYLNWYQQKPGKAPKLLIYG

ASRLETGVPSRFSGSGSGTDFTFTISSLQPEDIATYYCQQKHPRYPRTFG

QGTKVEIK

The Ke8 antibody includes a common heavy chain (SEQ ID NO: 2) encoded by the nucleic acid sequence shown in SEQ ID NO: 1 and includes a kappa light chain (SEQ ID NO: 12) encoded by the nucleic acid sequence shown in SEQ ID NO: 11.

>Ke8-LC-NT (SEQ ID NO: 11)

GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCACAAGCGGCGGCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8-LC-AA (SEQ ID NO: 12)
DIQMTQSPSSLSASVGDRVTITCRASQSISSYLNWYQQKPGKAPKLLIYA

ASSLQSGVPSRFSGSGSGTDFTLTISSLQPEDFATYYCQQFHKRRPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8 antibody includes a common variable heavy domain (SEQ ID NO: 114) encoded by the nucleic acid sequence shown in SEQ ID NO: 113 and includes a kappa variable light domain (SEQ ID NO: 124) encoded by the nucleic acid sequence shown in SEQ ID NO: 123.

>Ke8-VL-NT (SEQ ID NO: 123)

GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCACAAGCGGCGGCCGCAGACCTTCGGC

CAAGGGACCAAGGTGGAAATCAAA

>KE8-VL-AA (SEQ ID NO: 124)

DIQMTQSPSSLSASVGDRVTITCRASQSISSYLNWYQQKPGKAPKLLIYA

ASSLQSGVPSRFSGSGSGTDFTLTISSLQPEDFATYYCQQFHKRRPQTFG

QGTKVEIK

The Ke8H5 antibody includes a common heavy chain (SEQ ID NO: 2) encoded by the nucleic acid sequence shown in SEQ ID NO: 1 and includes a kappa light chain (SEQ ID NO: 14) encoded by the nucleic acid sequence shown in SEQ ID NO: 13.

>KE8H5-LC-NT (SEQ ID NO: 13)

GACATCCAGATGACCCAGTCTCCATCCTCCCTGTCTGCATCTGTAGGAGA

CAGAGTCACCATCACTTGCCGGGCAAGTCAGAGCATTGCGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTGCGCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8H5-LC-AA (SEQ ID NO: 14)

DIQMTQSPSSLSASVGDRVTITCRASQSIARYLNWYQQKPGKAPKLLIYA

ASSLQSGVPSRFSGSGSGTDFTLTISSLQPEDFATYYCQQFHKRAPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8H5 antibody includes a common variable heavy domain (SEQ ID NO: 114) encoded by the nucleic acid sequence shown in SEQ ID NO: 113 and includes a kappa variable light domain (SEQ ID NO: 126) encoded by the nucleic acid sequence shown in SEQ ID NO: 125.

>KE8H5-VL-NT (SEQ ID NO: 125)

GACATCCAGATGACCCAGTCTCCATCCTCCCTGTCTGCATCTGTAGGAGA

CAGAGTCACCATCACTTGCCGGGCAAGTCAGAGCATTGCGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTGCGCCGCAGACCTTCGGC

CAAGGGACCAAGGTGGAAATCAAA

>KE8H5-VL-AA (SEQ ID NO: 126)

DIQMTQSPSSLSASVGDRVTITCRASQSIARYLNWYQQKPGKAPKLLIYA

ASSLQSGVPSRFSGSGSGTDFTLTISSLQPEDFATYYCQQFHKRAPQTFG

QGTKVEIK

The Ke8B2 antibody includes a common heavy chain (SEQ ID NO: 2) encoded by the nucleic acid sequence shown in SEQ ID NO: 1 and includes a kappa light chain (SEQ ID NO: 16) encoded by the nucleic acid sequence shown in SEQ ID NO: 15.

>KE8B2-LC-NT (SEQ ID NO: 15)

GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCACCCGCGTGCCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8B2-LC-AA (SEQ ID NO: 16)

DIQMTQSPSSLSASVGDRVTITCRASQSIGKYLNWYQQKPGKAPKLLIYA

ASRLQSGVPSRFSGSGSGTDFTLTISSLQPEDFATYYCQQKHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8B2 antibody includes a common variable heavy domain (SEQ ID NO: 114) encoded by the nucleic acid sequence shown in SEQ ID NO: 113 and includes a kappa variable light domain (SEQ ID NO: 128) encoded by the nucleic acid sequence shown in SEQ ID NO: 127.

>KE8B2-VL-NT (SEQ ID NO: 127)

GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCACCCGCGTGCCCCGCGGACCTTCGGC

CAAGGGACCAAGGTGGAAATCAAA

>KE8B2-VL-AA (SEQ ID NO: 128)

DIQMTQSPSSLSASVGDRVTITCRASQSIGKYLNWYQQKPGKAPKLLIYA

ASRLQSGVPSRFSGSGSGTDFTLTISSLQPEDFATYYCQQKHPRAPRTFG

QGTKVEIK

The Ke8A2 antibody includes a common heavy chain (SEQ ID NO: 2) encoded by the nucleic acid sequence shown in SEQ ID NO: 1 and includes a kappa light chain (SEQ ID NO: 18) encoded by the nucleic acid sequence shown in SEQ ID NO: 17.

>KE8A2-LC-NT (SEQ ID NO: 17)

GACATCCAGATGACCCAGTCTCCATCCTCCCTGTCTGCATCTGTAGGAGA

CAGAGTCACCATCACTTGCCGGGCAAGTCAGAGCATTGATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCCCGTGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A2-LC-AA (SEQ ID NO: 18)

DIQMTQSPSSLSASVGDRVTITCRASQSIDRYLNWYQQKPGKAPKLLIYA

ASSLQSGVPSRFSGSGSGTDFTLTISSLQPEDFATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8A2 antibody includes a common variable heavy domain (SEQ ID NO: 114) encoded by the nucleic acid sequence shown in SEQ ID NO: 113 and includes a kappa variable light domain (SEQ ID NO: 130) encoded by the nucleic acid sequence shown in SEQ ID NO: 129.

>KE8A2-VL-NT (SEQ ID NO: 129)

GACATCCAGATGACCCAGTCTCCATCCTCCCTGTCTGCATCTGTAGGAGA

CAGAGTCACCATCACTTGCCGGGCAAGTCAGAGCATTGATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCCCGTGGGCCGAGGACCTTCGGC

CAAGGGACCAAGGTGGAAATCAAA

>KE8A2-VL-AA (SEQ ID NO: 130)

DIQMTQSPSSLSASVGDRVTITCRASQSIDRYLNWYQQKPGKAPKLLIYA

ASSLQSGVPSRFSGSGSGTDFTLTISSLQPEDFATYYCQQKHPRGPRTFG

QGTKVEIK

The Ke8E8 antibody includes a common heavy chain (SEQ ID NO: 2) encoded by the nucleic acid sequence shown in SEQ ID NO: 1 and includes a kappa light chain (SEQ ID NO: 20) encoded by the nucleic acid sequence shown in SEQ ID NO: 19.

>KE8E8-LC-NT (SEQ ID NO: 19)

GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCCCGTGGGCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8E8-LC-AA (SEQ ID NO: 20)

DIQMTQSPSSLSASVGDRVTITCQASQDINKYLNWYQQKPGKAPKLLIYA

ASSLQSGVPSRFSGSGSGTDFTLTISSLQPEDFATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8E8 antibody includes a common variable heavy domain (SEQ ID NO: 114) encoded by the nucleic acid sequence shown in SEQ ID NO: 113 and includes a kappa variable light domain (SEQ ID NO: 132) encoded by the nucleic acid sequence shown in SEQ ID NO: 131.

>KE8E8-VL-NT
(SEQ ID NO: 131)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCCCGTGGCCCGCGGACCTTCGGC

CAAGGGACCAAGGTGGAAATCAAA

>KE8E8-VL-AA
(SEQ ID NO: 132)
DIQMTQSPSSLSASVGDRVTITCQASQDINKYLNWYQQKPGKAPKLLIYA

ASSLQSGVPSRFSGSGSGTDFTLTISSLQPEDFATYYCQQKHPRGPRTFG

QGTKVEIK

The Ke8H3 antibody includes a common heavy chain (SEQ ID NO: 2) encoded by the nucleic acid sequence shown in SEQ ID NO: 1 and includes a kappa light chain (SEQ ID NO: 22) encoded by the nucleic acid sequence shown in SEQ ID NO: 21.

>KE8H3-LC-NT
(SEQ ID NO: 21)
GACATCCAGATGACCCAGTCTCCATCCTCCCTGTCTGCATCTGTAGGAGA

CAGAGTCACCATCACTTGCCGGGCAAGTCAGAGCATTAATAGGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8H3-LC-AA
(SEQ ID NO: 22)
DIQMTQSPSSLSASVGDRVTITCRASQSINRYLNWYQQKPGKAPKLLIYA

ASRLQSGVPSRFSGSGSGTDFTLTISSLQPEDFATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8H3 antibody includes a common variable heavy domain (SEQ ID NO: 114) encoded by the nucleic acid sequence shown in SEQ ID NO: 113 and includes a kappa variable light domain (SEQ ID NO: 134) encoded by the nucleic acid sequence shown in SEQ ID NO: 133.

>KE8H3-VL-NT
(SEQ ID NO: 133)
GACATCCAGATGACCCAGTCTCCATCCTCCCTGTCTGCATCTGTAGGAGA

CAGAGTCACCATCACTTGCCGGGCAAGTCAGAGCATTAATAGGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGGGCCGAGGACCTTCGGC

CAAGGGACCAAGGTGGAAATCAAA

>KE8H3-VL-AA
(SEQ ID NO: 134)
DIQMTQSPSSLSASVGDRVTITCRASQSINRYLNWYQQKPGKAPKLLIYA

ASRLQSGVPSRFSGSGSGTDFTLTISSLQPEDFATYYCQQKHPRGPRTFG

QGTKVEIK

The Ke8G6 antibody includes a common heavy chain (SEQ ID NO: 2) encoded by the nucleic acid sequence shown in SEQ ID NO: 1 and includes a kappa light chain (SEQ ID NO: 24) encoded by the nucleic acid sequence shown in SEQ ID NO: 23.

>KE8G6-LC-NT
(SEQ ID NO: 23)
GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8G6-LC-AA
(SEQ ID NO: 24)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8G6 antibody includes a common variable heavy domain (SEQ ID NO: 114) encoded by the nucleic acid sequence shown in SEQ ID NO: 113 and includes a kappa variable light domain (SEQ ID NO: 136) encoded by the nucleic acid sequence shown in SEQ ID NO: 135.

>KE8G6-VL-NT (SEQ ID NO: 135)
GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCGCCGAAGACCTTCGGC

CAAGGGACCAAGGTGGAAATCAAA

>KE8G6-VL-AA (SEQ ID NO: 136)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRAPKTFG

QGTKVEIK

The Ke8A3 antibody includes a common heavy chain (SEQ ID NO: 2) encoded by the nucleic acid sequence shown in SEQ ID NO: 1 and includes a kappa light chain (SEQ ID NO: 26) encoded by the nucleic acid sequence shown in SEQ ID NO: 25.

>KE8A3-LC-NT (SEQ ID NO: 25)
GACATCCAGATGACCCAGTCTCCATCCTCCCTGTCTGCATCTGTAGGAGA

CAGAGTCACCATCACTTGCCGGGTAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCCCGTGGGCCGAGCACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A3-LC-AA (SEQ ID NO: 26)
DIQMTQSPSSLSASVGDRVTITCRVSQSISKYLNWYQQKPGKAPKLLIYA

ASSLQSGVPSRFSGSGSGTDFTLTISSLQPEDFATYYCQQRHPRGPSTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8A3 antibody includes a common variable heavy domain (SEQ ID NO: 114) encoded by the nucleic acid sequence shown in SEQ ID NO: 113 and includes a kappa variable light domain (SEQ ID NO: 138) encoded by the nucleic acid sequence shown in SEQ ID NO: 137.

>KE8A3-VL-NT (SEQ ID NO: 137)
GACATCCAGATGACCCAGTCTCCATCCTCCCTGTCTGCATCTGTAGGAGA

CAGAGTCACCATCACTTGCCGGGTAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCCCGTGGGCCGAGCACCTTCGGC

CAAGGGACCAAGGTGGAAATCAAA

>KE8A3-VL-AA (SEQ ID NO: 138)
DIQMTQSPSSLSASVGDRVTITCRVSQSISKYLNWYQQKPGKAPKLLIYA

ASSLQSGVPSRFSGSGSGTDFTLTISSLQPEDFATYYCQQRHPRGPSTFG

QGTKVEIK

The Ke81A3 antibody includes a common heavy chain (SEQ ID NO: 2) encoded by the nucleic acid sequence shown in SEQ ID NO: 1 and includes a kappa light chain (SEQ ID NO: 28) encoded by the nucleic acid sequence shown in SEQ ID NO: 27.

>KE81A3-LC-NT (SEQ ID NO: 27)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGCCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE81A3-LC-AA (SEQ ID NO: 28)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke81A3 antibody includes a common variable heavy domain (SEQ ID NO: 114) encoded by the nucleic acid sequence shown in SEQ ID NO: 113 and includes a kappa variable light domain (SEQ ID NO: 140) encoded by the nucleic acid sequence shown in SEQ ID NO: 139.

>KE81A3-VL-NT
(SEQ ID NO: 139)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGCCCCGCGGACCTTCGGC

CAAGGGACCAAGGTGGAAATCAAA

>KE81A3-VL-AA
(SEQ ID NO: 140)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRAPRTFG

QGTKVEIK

The Ke8A8 antibody includes a common heavy chain (SEQ ID NO: 2) encoded by the nucleic acid sequence shown in SEQ ID NO: 1 and includes a kappa light chain (SEQ ID NO: 30) encoded by the nucleic acid sequence shown in SEQ ID NO: 29.

>KE8A8-LC-NT
(SEQ ID NO: 29)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A8-LC-AA
(SEQ ID NO: 30)
DIQMTQSPSSLSASVGDRVTITCRASQSISKYLNWYQQKPGKAPKLLIYA

ASTLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8A8 antibody includes a common variable heavy domain (SEQ ID NO: 114) encoded by the nucleic acid sequence shown in SEQ ID NO: 113 and includes a kappa variable light domain (SEQ ID NO: 142) encoded by the nucleic acid sequence shown in SEQ ID NO: 141.

>KE8A8-VL-NT
(SEQ ID NO: 141)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCGCCGAAGACCTTCGGC

CAAGGGACCAAGGTGGAAATCAAA

>KE8A8-VL-AA
(SEQ ID NO: 142)
DIQMTQSPSSLSASVGDRVTITCRASQSISKYLNWYQQKPGKAPKLLIYA

ASTLQSGVPSRFSGSGSGTDFTLTISSLQPEDFATYYCQQMHPRAPKTFG

QGTKVEIK

The Ke8C7 antibody includes a common heavy chain (SEQ ID NO: 2) encoded by the nucleic acid sequence shown in SEQ ID NO: 1 and includes a kappa light chain (SEQ ID NO: 32) encoded by the nucleic acid sequence shown in SEQ ID NO: 31.

>KE8C7-LC-NT
(SEQ ID NO: 31)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGCGCCATCCGCGTGGCCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8C7-LC-AA
(SEQ ID NO: 32)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8C7 antibody includes a common variable heavy domain (SEQ ID NO: 114) encoded by the nucleic acid sequence shown in SEQ ID NO: 113 and includes a kappa variable light domain (SEQ ID NO: 144) encoded by the nucleic acid sequence shown in SEQ ID NO: 143.

>KE8C7-VL-NT (SEQ ID NO: 143)

GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGCGCCATCCGCGTGGCCCGAGGACCTTCGGC

CAAGGGACCAAGGTGGAAATCAAA

>KE8C7-VL-AA (SEQ ID NO: 144)

DIQMTQSPSSLSASVGDRVTITCQASQDINRYLNWYQQKPGKAPKLLIYA

ASSLQSGVPSRFSGSGSGTDFTLTISSLQPEDFATYYCQQRHPRGPRTFG

QGTKVEIK

The Ke8G2 antibody includes a common heavy chain (SEQ ID NO: 2) encoded by the nucleic acid sequence shown in SEQ ID NO: 1 and includes a kappa light chain (SEQ ID NO: 34) encoded by the nucleic acid sequence shown in SEQ ID NO: 33.

>KE8G2-LC-NT (SEQ ID NO: 33)

GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAACAGTCTGCAACCTGAAGATTTTG

CAACTTACTACTGTCAGCAGAAGCATCCCCGTGCGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8G2-LC-AA (SEQ ID NO: 34)

DIQMTQSPSSLSASVGDRVTITCRASQSIGRYLNWYQQKPGKAPKLLIYA

ASRLQSGVPSRFSGSGSGTDFTLTINSLQPEDFATYYCQQKHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8G2 antibody includes a common variable heavy domain (SEQ ID NO: 114) encoded by the nucleic acid sequence shown in SEQ ID NO: 113 and includes a kappa variable light domain (SEQ ID NO: 146) encoded by the nucleic acid sequence shown in SEQ ID NO: 145.

>KE8G2-VL-NT (SEQ ID NO: 145)

GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAACAGTCTGCAACCTGAAGATTTTG

CAACTTACTACTGTCAGCAGAAGCATCCCCGTGCGCCGAGGACCTTCGGC

CAAGGGACCAAGGTGGAAATCAAA

>KE8G2-VL-AA (SEQ ID NO: 146)

DIQMTQSPSSLSASVGDRVTITCRASQSIGRYLNWYQQKPGKAPKLLIYA

ASRLQSGVPSRFSGSGSGTDFTLTINSLQPEDFATYYCQQKHPRAPRTFG

QGTKVEIK

The Ke81G9 antibody includes a common heavy chain (SEQ ID NO: 2) encoded by the nucleic acid sequence shown in SEQ ID NO: 1 and includes a kappa light chain (SEQ ID NO: 36) encoded by the nucleic acid sequence shown in SEQ ID NO: 35.

>KE81G9-LC-NT (SEQ ID NO: 35)

GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGCGGCATAAGCGTTCCCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE81G9-LC-AA (SEQ ID NO: 36)

DIQMTQSPSSLSASVGDRVTITCRASQSIDKYLNWYQQKPGKAPKLLIYA

ASRLQSGVPSRFSGSGSGTDFTLTISSLQPEDFATYYCQQRHKRSPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke81G9 antibody includes a common variable heavy domain (SEQ ID NO: 114) encoded by the nucleic acid sequence shown in SEQ ID NO: 113 and includes a kappa variable light domain (SEQ ID NO: 148) encoded by the nucleic acid sequence shown in SEQ ID NO: 147.

\>KE81G9-VL-NT (SEQ ID NO: 147)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGCGGCATAAGCGTTCCCCGCAGACCTTCGGC

CAAGGGACCAAGGTGGAAATCAAA

\>KE81G9-VL-AA (SEQ ID NO: 148)
DIQMTQSPSSLSASVGDRVTITCRASQSIDKYLNWYQQKPGKAPKLLIYA

ASRLQSGVPSRFSGSGSGTDFTLTISSLQPEDFATYYCQQRHKRSPQTFG

QGTKVEIK

The Ke8F2 antibody includes a common heavy chain (SEQ ID NO: 2) encoded by the nucleic acid sequence shown in SEQ ID NO: 1 and includes a kappa light chain (SEQ ID NO: 38) encoded by the nucleic acid sequence shown in SEQ ID NO: 37.

\>KE8F2-LC-NT (SEQ ID NO: 37)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGCGCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

\>KE8F2-LC-AA (SEQ ID NO: 38)
DIQMTQSPSSLSASVGDRVTITCRASQSIDKYLNWYQQKPGKAPKLLIYA

ASSLQSGVPSRFSGSGSGTDFTLTISSLQPEDFATYYCQQKHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8F2 antibody includes a common variable heavy domain (SEQ ID NO: 114) encoded by the nucleic acid sequence shown in SEQ ID NO: 113 and includes a kappa variable light domain (SEQ ID NO: 150) encoded by the nucleic acid sequence shown in SEQ ID NO: 149.

\>KE8F2-VL-NT (SEQ ID NO: 149)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGCGCCGCGGACCTTCGGC

CAAGGGACCAAGGTGGAAATCAAA

\>KE8F2-VL-AA (SEQ ID NO: 150)
DIQMTQSPSSLSASVGDRVTITCRASQSIDKYLNWYQQKPGKAPKLLIYA

ASSLQSGVPSRFSGSGSGTDFTLTISSLQPEDFATYYCQQKHPRAPRTFG

QGTKVEIK

The Ke8B7 antibody includes a common heavy chain (SEQ ID NO: 2) encoded by the nucleic acid sequence shown in SEQ ID NO: 1 and includes a kappa light chain (SEQ ID NO: 40) encoded by the nucleic acid sequence shown in SEQ ID NO: 39.

\>KE8B7-LC-NT (SEQ ID NO: 39)
GACATCCAGATGACCCAGTCTCCATCCTCCCTGTCTGCATCTGTAGGAGA

CAGAGTCACCATCACTTGCCGGGCAAGTCAGAGCATTGGGAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTAGCCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

\>KE8B7-LC-AA (SEQ ID NO: 40)
DIQMTQSPSSLSASVGDRVTITCRASQSIGKYLNWYQQKPGKAPKLLIYA

ASSLQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8B7 antibody includes a common variable heavy domain (SEQ ID NO: 114) encoded by the nucleic acid sequence shown in SEQ ID NO: 113 and includes a kappa variable light domain (SEQ ID NO: 152) encoded by the nucleic acid sequence shown in SEQ ID NO: 151.

>KE8B7-VL-NT (SEQ ID NO: 151)
GACATCCAGATGACCCAGTCTCCATCCTCCCTGTCTGCATCTGTAGGAGA

CAGAGTCACCATCACTTGCCGGGCAAGTCAGAGCATTGGGAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTAGCCCGAAGACCTTCGGC

CAAGGGACCAAGGTGGAAATCAAA

>KE8B7-VL-AA (SEQ ID NO: 152)
DIQMTQSPSSLSASVGDRVTITCRASQSIGKYLNWYQQKPGKAPKLLIYA

ASSLQSGVPSRFSGSGSGTDFTLTISSLQPEDFATYYCQQMHPRSPKTFG

QGTKVEIK

The Ke8C4 antibody includes a common heavy chain (SEQ ID NO: 2) encoded by the nucleic acid sequence shown in SEQ ID NO: 1 and includes a kappa light chain (SEQ ID NO: 42) encoded by the nucleic acid sequence shown in SEQ ID NO: 41.

>KE8C4-LC-NT (SEQ ID NO: 41)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATGCT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8C4-LC-AA (SEQ ID NO: 42)
DIQMTQSPSSLSASVGDRVTITCRASQSISRYLNWYQQKPGKAPKLLIYA

ASNLQSGVPSRFSGSGSGTDFTLTISSLQPEDFATYYCQQMHPRGPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8C4 antibody includes a common variable heavy domain (SEQ ID NO: 114) encoded by the nucleic acid sequence shown in SEQ ID NO: 113 and includes a kappa variable light domain (SEQ ID NO: 154) encoded by the nucleic acid sequence shown in SEQ ID NO: 153.

>KE8C4-VL-NT (SEQ ID NO: 153)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATGCT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAA

>KE8C4-VL-AA (SEQ ID NO: 154)
DIQMTQSPSSLSASVGDRVTITCRASQSISRYLNWYQQKPGKAPKLLIYA

ASNLQSGVPSRFSGSGSGTDFTLTISSLQPEDFATYYCQQMHPRGPKTFG

QGTKVEIK

The Ke8F1 antibody includes a common heavy chain (SEQ ID NO: 2) encoded by the nucleic acid sequence shown in SEQ ID NO: 1 and includes a kappa light chain (SEQ ID NO: 44) encoded by the nucleic acid sequence shown in SEQ ID NO: 43.

>KE8F1-LC-NT (SEQ ID NO: 43)
GACATCCAGATGACCCAGTCTCCATCCTCCCTGTCTGCATCTGTAGGAGA

CAGAGTCACCATCACTTGCCGGGCAAGTCAGAGCATTGCTTCTTATGTAA

ATTGGTATCAGCAGAAACCAGGGAAAGCCCCTAAGCTCCTGATCTATGCT

GCATCCGGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTCGGCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8F1-LC-AA (SEQ ID NO: 44)
DIQMTQSPSSLSASVGDRVTITCRASQSIASYVNWYQQKPGKAPKLLIYA

ASGLQSGVPSRFSGSGSGTDFTLTISSLQPEDFATYYCQQFHKRRPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8F1 antibody includes a common variable heavy domain (SEQ ID NO: 114) encoded by the nucleic acid sequence shown in SEQ ID NO: 113 and includes a kappa variable light domain (SEQ ID NO: 156) encoded by the nucleic acid sequence shown in SEQ ID NO: 155.

\>KE8F1-VL-NT (SEQ ID NO: 155)
GACATCCAGATGACCCAGTCTCCATCCTCCCTGTCTGCATCTGTAGGAGA

CAGAGTCACCATCACTTGCCGGGCAAGTCAGAGCATTGCTTCTTATGTAA

ATTGGTATCAGCAGAAACCAGGGAAAGCCCCTAAGCTCCTGATCTATGCT

GCATCCGGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTCGGCCGCAGACCTTCGGC

CAAGGGACCAAGGTGGAAATCAAA

\>KE8F1-VL-AA (SEQ ID NO: 156)
DIQMTQSPSSLSASVGDRVTITCRASQSIASYVNWYQQKPGKAPKLLIYA

ASGLQSGVPSRFSGSGSGTDFTLTISSLQPEDFATYYCQQFHKRRPQTFG

QGTKVEIK

The Ke8G11 antibody includes a common heavy chain (SEQ ID NO: 2) encoded by the nucleic acid sequence shown in SEQ ID NO: 1 and includes a kappa light chain (SEQ ID NO: 46) encoded by the nucleic acid sequence shown in SEQ ID NO: 45.

\>KE8G11-LC-NT (SEQ ID NO: 45)
GACATCCAGATGACCCAGTCTCCATCCTCCCTGTCTGCATCTGTAGGAGA

CAGAGTCACCATCACTTGCCGGGCAAGTCAGAGCATTGGGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

\>KE8G11-LC-AA (SEQ ID NO: 46)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRGPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8G11 antibody includes a common variable heavy domain (SEQ ID NO: 114) encoded by the nucleic acid sequence shown in SEQ ID NO: 113 and includes a kappa variable light domain (SEQ ID NO: 158) encoded by the nucleic acid sequence shown in SEQ ID NO: 157.

\>KE8G11-VL-NT (SEQ ID NO: 157)
GACATCCAGATGACCCAGTCTCCATCCTCCCTGTCTGCATCTGTAGGAGA

CAGAGTCACCATCACTTGCCGGGCAAGTCAGAGCATTGGGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAA

\>KE8G11-VL-AA (SEQ ID NO: 158)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRGPKTFG

QGTKVEIK

The Ke8H6 antibody includes a common heavy chain (SEQ ID NO: 2) encoded by the nucleic acid sequence shown in SEQ ID NO: 1 and includes a kappa light chain (SEQ ID NO: 48) encoded by the nucleic acid sequence shown in SEQ ID NO: 47.

\>KE8H6-LC-NT (SEQ ID NO: 47)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGCGCACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

\>KE8H6-LC-AA (SEQ ID NO: 48)
DIQMTQSPSSLSASVGDRVTITCRASQSISKYLNWYQQKPGKAPKLLIYN

ASTLQSGVPSRFSGSGSGTDFTLTISSLQPEDFATYYCQQRHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8H6 antibody includes a common variable heavy domain (SEQ ID NO: 114) encoded by the nucleic acid sequence shown in SEQ ID NO: 113 and includes a kappa variable light domain (SEQ ID NO: 160) encoded by the nucleic acid sequence shown in SEQ ID NO: 159.

>KE8H6-VL-NT (SEQ ID NO: 159)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGCGCACCTTCGGC

CAAGGGACCAAGGTGGAAATCAAA

>KE8H6-VL-AA (SEQ ID NO: 160)
DIQMTQSPSSLSASVGDRVTITCRASQSISKYLNWYQQKPGKAPKLLIYN

ASTLQSGVPSRFSGSGSGTDFTLTISSLQPEDFATYYCQQRHPRGPRTFG

QGTKVEIK

The Ke84G9 antibody includes a common heavy chain (SEQ ID NO: 2) encoded by the nucleic acid sequence shown in SEQ ID NO: 1 and includes a kappa light chain (SEQ ID NO: 50) encoded by the nucleic acid sequence shown in SEQ ID NO: 49.

>KE84G9-LC-NT (SEQ ID NO: 49)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTAGCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE84G9-LC-AA (SEQ ID NO: 50)
DIQMTQSPSSLSASVGDRVTITCRASQSISKYLNWYQQKPGKAPKLLIYA

ASSLQSGVPSRFSGSGSGTDFTLTISSLQPEDFATYYCQQKHPRSPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke84G9 antibody includes a common variable heavy domain (SEQ ID NO: 114) encoded by the nucleic acid sequence shown in SEQ ID NO: 113 and includes a kappa variable light domain (SEQ ID NO: 162) encoded by the nucleic acid sequence shown in SEQ ID NO: 161.

>KE84G9-VL-NT (SEQ ID NO: 161)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTAGCCCGCGGACCTTCGGC

CAAGGGACCAAGGTGGAAATCAAA

>KE84G9-VL-AA (SEQ ID NO: 162)
DIQMTQSPSSLSASVGDRVTITCRASQSISKYLNWYQQKPGKAPKLLIYA

ASSLQSGVPSRFSGSGSGTDFTLTISSLQPEDFATYYCQQKHPRSPRTFG

QGTKVEIK

The Ke8A4 antibody includes a common heavy chain (SEQ ID NO: 2) encoded by the nucleic acid sequence shown in SEQ ID NO: 1 and includes a kappa light chain (SEQ ID NO: 52) encoded by the nucleic acid sequence shown in SEQ ID NO: 51.

>KE8A4-LC-NT (SEQ ID NO: 51)
GACATCCAGATGACCCAGTCTCCATCCTCCCTGTCTGCATCTGTAGGAGA

CAGAGTCACCATCACTTGCCGGGCAAGTCAGAGCATTGCTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTAGCCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A4-LC-AA (SEQ ID NO: 52)
DIQMTQSPSSLSASVGDRVTITCRASQSIAKYLNWYQQKPGKAPKLLIYA

ASSLQSGVPSRFSGSGSGTDFTLTISSLQPEDFATYYCQQFHKRSPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8A4 antibody includes a common variable heavy domain (SEQ ID NO: 114) encoded by the nucleic acid sequence shown in SEQ ID NO: 113 and includes a kappa variable light domain (SEQ ID NO: 164) encoded by the nucleic acid sequence shown in SEQ ID NO: 163.

>KE8A4-VL-NT
(SEQ ID NO: 163)
GACATCCAGATGACCCAGTCTCCATCCTCCCTGTCTGCATCTGTAGGAGA

CAGAGTCACCATCACTTGCCGGGCAAGTCAGAGCATTGCTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTAGCCCGCAGACCTTCGGC

CAAGGGACCAAGGTGGAAATCAAA

>KE8A4-VL-AA
(SEQ ID NO: 164)
DIQMTQSPSSLSASVGDRVTITCRASQSIAKYLNWYQQKPGKAPKLLIYA

ASSLQSGVPSRFSGSGSGTDFTLTISSLQPEDFATYYCQQFHKRSPQTFG

QGTKVEIK

The Ke86G9 antibody includes a common heavy chain (SEQ ID NO: 2) encoded by the nucleic acid sequence shown in SEQ ID NO: 1 and includes a kappa light chain (SEQ ID NO: 54) encoded by the nucleic acid sequence shown in SEQ ID NO: 53.

>KE86G9-LC-NT
(SEQ ID NO: 53)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGACCACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE86G9-LC-AA
(SEQ ID NO: 54)
DIQMTQSPSSLSASVGDRVTITCRASQSISKYLNWYQQKPGKAPKLLIYN

ASNLQSGVPSRFSGSGSGTDFTLTISSLQPEDFATYYCQQRHPRGPTTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke86G9 antibody includes a common variable heavy domain (SEQ ID NO: 114) encoded by the nucleic acid sequence shown in SEQ ID NO: 113 and includes a kappa variable light domain (SEQ ID NO: 166) encoded by the nucleic acid sequence shown in SEQ ID NO: 165.

>KE86G9-VL-NT
(SEQ ID NO: 165)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGACCACCTTCGGC

CAAGGGACCAAGGTGGAAATCAAA

>KE86G9-VL-AA
(SEQ ID NO: 166)
DIQMTQSPSSLSASVGDRVTITCRASQSISKYLNWYQQKPGKAPKLLIYN

ASNLQSGVPSRFSGSGSGTDFTLTISSLQPEDFATYYCQQRHPRGPTTFG

QGTKVEIK

The Ka3 antibody includes a common heavy chain (SEQ ID NO: 2) encoded by the nucleic acid sequence shown in SEQ ID NO: 1 and includes a kappa light chain (SEQ ID NO: 56) encoded by the nucleic acid sequence shown in SEQ ID NO: 55.

>KA3-LC-NT
(SEQ ID NO: 55)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGCGCCCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3-LC-AA
(SEQ ID NO: 56)
DIQMTQSPSSLSASVGDRVTITCRASQSISSYLNWYQQKPGKAPKLLIYA

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3 antibody includes a common variable heavy domain (SEQ ID NO: 114) encoded by the nucleic acid sequence shown in SEQ ID NO: 113 and includes a kappa variable light domain (SEQ ID NO: 168) encoded by the nucleic acid sequence shown in SEQ ID NO: 167.

>KA3-VL-NT
(SEQ ID NO: 167)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGCGCCCCGAAGACCTTCGGC

CAAGGGACCAAGGTGGAAATCAAA

>KA3-VL-AA
(SEQ ID NO: 168)
DIQMTQSPSSLSASVGDRVTITCRASQSISSYLNWYQQKPGKAPKLLIYA

ASSLQSGVPSRFSGSGSGTDFTLTISSLQPEDFATYYCQQMHPRAPKTFG

QGTKVEIK

The Ka3A2 antibody includes a common heavy chain (SEQ ID NO: 2) encoded by the nucleic acid sequence shown in SEQ ID NO: 1 and includes a kappa light chain (SEQ ID NO: 58) encoded by the nucleic acid sequence shown in SEQ ID NO: 57.

>KA3A2-LC-NT
(SEQ ID NO: 57)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3A2-LC-AA
(SEQ ID NO: 58)
DIQMTQSPSSLSASVGDRVTITCRASQSISKYLNWYQQKPGKAPKLLIYA

ASRLQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>KA3A2-VL-NT
(SEQ ID NO: 169)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAA

>KA3A2-VL-AA
(SEQ ID NO: 170)
DIQMTQSPSSLSASVGDRVTITCRASQSISKYLNWYQQKPGKAPKLLIYA

ASRLQSGVPSRFSGSGSGTDFTLTISSLQPEDFATYYCQQMHPRSPKTFG

QGTKVEIK

The Ka3H3 antibody includes a common heavy chain (SEQ ID NO: 2) encoded by the nucleic acid sequence shown in SEQ ID NO: 1 and includes a kappa light chain (SEQ ID NO: 60) encoded by the nucleic acid sequence shown in SEQ ID NO: 59.

>KA3H3-LC-NT
(SEQ ID NO: 59)
GACATCCAGATGACCCAGTCTCCATCCTCCCTGTCTGCATCTGTAGGAGA

CAGAGTCACCATCACTTGCCAGGCGAGTCAGGACATTGCTAAGTATTTAA

ATTGGTATCAGCAGAAACCAGGGAAAGCCCCTAAGCTCCTGATCTATGCT

GCATCCGCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3H3-LC-AA
(SEQ ID NO: 60)
DIQMTQSPSSLSASVGDRVTITCQASQDIAKYLNWYQQKPGKAPKLLIYA

ASALQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3A2 antibody includes a common variable heavy domain (SEQ ID NO: 114) encoded by the nucleic acid sequence shown in SEQ ID NO: 113 and includes a kappa variable light domain (SEQ ID NO: 170) encoded by the nucleic acid sequence shown in SEQ ID NO: 169.

The Ka3H3 antibody includes a common variable heavy domain (SEQ ID NO: 114) encoded by the nucleic acid sequence shown in SEQ ID NO: 113 and includes a kappa variable light domain (SEQ ID NO: 172) encoded by the nucleic acid sequence shown in SEQ ID NO: 171.

\>KA3H3-VL-NT
(SEQ ID NO: 171)
GACATCCAGATGACCCAGTCTCCATCCTCCCTGTCTGCATCTGTAGGAGA

CAGAGTCACCATCACTTGCCAGGCGAGTCAGGACATTGCTAAGTATTTAA

ATTGGTATCAGCAGAAACCAGGGAAAGCCCCTAAGCTCCTGATCTATGCT

GCATCCGCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAA

\>KA3H3-VL-AA
(SEQ ID NO: 172)
DIQMTQSPSSLSASVGDRVTITCQASQDIAKYLNWYQQKPGKAPKLLIYA

ASALQSGVPSRFSGSGSGTDFTLTISSLQPEDFATYYCQQMHPRSPKTFG

QGTKVEIK

The Ka3A3 antibody includes a common heavy chain (SEQ ID NO: 2) encoded by the nucleic acid sequence shown in SEQ ID NO: 1 and includes a kappa light chain (SEQ ID NO: 62) encoded by the nucleic acid sequence shown in SEQ ID NO: 61.

\>KA3A3-LC-NT
(SEQ ID NO: 61)
GACATCCAGATGACCCAGTCTCCATCCTCCCTGTCTGCATCTGTAGGAGA

CAGAGTCACCATCACTTGCCGGGCAAGTCAGAGCATTGCTAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

\>KA3A3-LC-AA
(SEQ ID NO: 62)
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3A3 antibody includes a common variable heavy domain (SEQ ID NO: 114) encoded by the nucleic acid sequence shown in SEQ ID NO: 113 and includes a kappa variable light domain (SEQ ID NO: 174) encoded by the nucleic acid sequence shown in SEQ ID NO: 173.

\>KA3A3-VL-NT
(SEQ ID NO: 173)
GACATCCAGATGACCCAGTCTCCATCCTCCCTGTCTGCATCTGTAGGAGA

CAGAGTCACCATCACTTGCCGGGCAAGTCAGAGCATTGCTAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAA

\>KA3A3-VL-AA
(SEQ ID NO: 174)
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRAPKTFG

QGTKVEIK

The Ka3H8 antibody includes a common heavy chain (SEQ ID NO: 2) encoded by the nucleic acid sequence shown in SEQ ID NO: 1 and includes a kappa light chain (SEQ ID NO: 64) encoded by the nucleic acid sequence shown in SEQ ID NO: 63.

\>KA3H8-LC-NT
(SEQ ID NO: 63)
GACATCCAGATGACCCAGTCTCCATCCTCCCTGTCTGCATCTGTAGGAGA

CAGAGTCACCATCACTTGCCGGGCAAGTCAGAGCATTGCGAGTTATTTAA

ATTGGTATCAGCAGAAACCAGGGAAAGCCCCTAAGCTCCTGATCTATGCG

GCATCCAGGTTGCAAAGTGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

\>KA3H8-LC-AA
(SEQ ID NO: 64)
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3H8 antibody includes a common variable heavy domain (SEQ ID NO: 114) encoded by the nucleic acid sequence shown in SEQ ID NO: 113 and includes a kappa variable light domain (SEQ ID NO: 176) encoded by the nucleic acid sequence shown in SEQ ID NO: 175.

>KA3H8-VL-NT (SEQ ID NO: 175)
GACATCCAGATGACCCAGTCTCCATCCTCCCTGTCTGCATCTGTAGGAGA

CAGAGTCACCATCACTTGCCGGGCAAGTCAGAGCATTGCGAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAA

>KA3H8-VL-AA (SEQ ID NO: 176)
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRSPKTFG

QGTKVEIK

The Ka3B2 antibody includes a common heavy chain (SEQ ID NO: 2) encoded by the nucleic acid sequence shown in SEQ ID NO: 1 and includes a kappa light chain (SEQ ID NO: 66) encoded by the nucleic acid sequence shown in SEQ ID NO: 65.

>KA3B2-LC-NT (SEQ ID NO: 65)
GACATCCAGATGACCCAGTCTCCATCCTCCCTGTCTGCATCTGTAGGAGA

CAGAGTCACCATCACTTGCCGGGCAAGTCAGAACATTGGTAAGTATTTAA

ATTGGTATCAGCAGAAACCAGGGAAAGCCCCTAAGCTCCTGATCTATAGT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3B2-LC-AA (SEQ ID NO: 66)
DIQMTQSPSSLSASVGDRVTITCRASQNIGKYLNWYQQKPGKAPKLLIYS

ASRLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3B2 antibody includes a common variable heavy domain (SEQ ID NO: 114) encoded by the nucleic acid sequence shown in SEQ ID NO: 113 and includes a kappa variable light domain (SEQ ID NO: 178) encoded by the nucleic acid sequence shown in SEQ ID NO: 177.

>KA3B2-VL-NT (SEQ ID NO: 177)
GACATCCAGATGACCCAGTCTCCATCCTCCCTGTCTGCATCTGTAGGAGA

CAGAGTCACCATCACTTGCCGGGCAAGTCAGAACATTGGTAAGTATTTAA

ATTGGTATCAGCAGAAACCAGGGAAAGCCCCTAAGCTCCTGATCTATAGT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAA

>KA3B2-VL-AA (SEQ ID NO: 178)
DIQMTQSPSSLSASVGDRVTITCRASQNIGKYLNWYQQKPGKAPKLLIYS

ASRLQSGVPSRFSGSGSGTDFTLTISSLQPEDFATYYCQQMHPRAPKTFG

QGTKVEIK

The Ka3C5 antibody includes a common heavy chain (SEQ ID NO: 2) encoded by the nucleic acid sequence shown in SEQ ID NO: 1 and includes a kappa light chain (SEQ ID NO: 68) encoded by the nucleic acid sequence shown in SEQ ID NO: 67.

>KA3C5-LC-NT (SEQ ID NO: 67)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATTCT

GCATCCTCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCCCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3C5-LC-AA (SEQ ID NO: 68)
DIQMTQSPSSLSASVGDRVTITCRASQSISRYLNWYQQKPGKAPKLLIYS

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3C5 antibody includes a common variable heavy domain (SEQ ID NO: 114) encoded by the nucleic acid sequence shown in SEQ ID NO: 113 and includes a kappa variable light domain (SEQ ID NO: 180) encoded by the nucleic acid sequence shown in SEQ ID NO: 179.

>KA3C5-VL-NT (SEQ ID NO: 179)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATTCT

GCATCCTCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCCCCGAAAACCTTCGGC

CAAGGGACCAAGGTGGAAATCAAA

>KA3C5-VL-AA (SEQ ID NO: 180)
DIQMTQSPSSLSASVGDRVTITCRASQSISRYLNWYQQKPGKAPKLLIYS

ASSLQSGVPSRFSGSGSGTDFTLTISSLQPEDFATYYCQQMHPRAPKTFG

QGTKVEIK

The Ka3G2 antibody includes a common heavy chain (SEQ ID NO: 2) encoded by the nucleic acid sequence shown in SEQ ID NO: 1 and includes a kappa light chain (SEQ ID NO: 70) encoded by the nucleic acid sequence shown in SEQ ID NO: 69.

>KA3G2-LC-NT (SEQ ID NO: 69)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGGGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3G2-LC-AA (SEQ ID NO: 70)
DIQMTQSPSSLSASVGDRVTITCRASQSIDKYLNWYQQKPGKAPKLLIYA

ASRLQSGVPSRFSGSGSGTDFTLTISSLQPEDFATYYCQQMHPRGPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3G2 antibody includes a common variable heavy domain (SEQ ID NO: 114) encoded by the nucleic acid sequence shown in SEQ ID NO: 113 and includes a kappa variable light domain (SEQ ID NO: 182) encoded by the nucleic acid sequence shown in SEQ ID NO: 181.

>KA3G2-VL-NT (SEQ ID NO: 181)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGGGCCGAAAACCTTCGGC

CAAGGGACCAAGGTGGAAATCAAA

>KA3G2-VL-AA (SEQ ID NO: 182)
DIQMTQSPSSLSASVGDRVTITCRASQSIDKYLNWYQQKPGKAPKLLIYA

ASRLQSGVPSRFSGSGSGTDFTLTISSLQPEDFATYYCQQMHPRGPKTFG

QGTKVEIK

The Ka3D3 antibody includes a common heavy chain (SEQ ID NO: 2) encoded by the nucleic acid sequence shown in SEQ ID NO: 1 and includes a kappa light chain (SEQ ID NO: 72) encoded by the nucleic acid sequence shown in SEQ ID NO: 71.

>KA3D3-LC-NT (SEQ ID NO: 71)
GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3D3-LC-AA (SEQ ID NO: 72)
DIQMTQSPSSLSASVGDRVTITCRASQSIGKYLNWYQQKPGKAPKLLIYA

ASRLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3D3 antibody includes a common variable heavy domain (SEQ ID NO: 114) encoded by the nucleic acid sequence shown in SEQ ID NO: 113 and includes a kappa variable light domain (SEQ ID NO: 184) encoded by the nucleic acid sequence shown in SEQ ID NO: 183.

>KA3D3-VL-NT
(SEQ ID NO: 183)
GACATCCAGATGACCCAGTCTCCATCCTCCCTGTCTGCATCTGTAGGAGA
CAGAGTCACCATCACTTGCCGGGCAAGTCAGAGCATTGGTAAGTATTTAA
ATTGGTATCAGCAGAAACCAGGGAAAGCCCCTAAGCTCCTGATCTATGCT
GCATCCAGGTTGCAAAGTGGGGTCCCATCAAGGTTCAGTGGCAGTGGATC
TGGGACAGATTTCACTCTCACCATCAGCAGTCTGCAACCTGAAGATTTTG
CAACTTACTACTGTCAGCAGATGCATCCTCGCGCGCCGAAAACCTTCGGC
CAAGGGACCAAGGTGGAAATCAAA

>KA3D3-VL-AA
(SEQ ID NO: 184)
DIQMTQSPSSLSASVGDRVTITCRASQSIGKYLNWYQQKPGKAPKLLIYA
ASRLQSGVPSRFSGSGSGTDFTLTISSLQPEDFATYYCQQMHPRAPKTFG
QGTKVEIK

The Kc4 antibody includes a common heavy chain (SEQ ID NO: 2) encoded by the nucleic acid sequence shown in SEQ ID NO: 1 and includes a lambda light chain (SEQ ID NO: 74) encoded by the nucleic acid sequence shown in SEQ ID NO: 73.

>KC4-LC-NT
(SEQ ID NO: 73)
CAGTCTGCCCTGACTCAGCCTGCCTCCGTGTCTGGGTCTCCTGGACAGTC
GATCACCATCTCCTGCACTGGAACCAGCAGTGACGTTGGTGGTTATAACT
ATGTCTCCTGGTACCAACAGCACCCAGGCAAAGCCCCCAAACTCATGATT
TATGAGGTCAGTAATCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4-LC-AA
(SEQ ID NO: 74)
QSALTQPASVSGSPGQSITISCTGTSSDVGGYNYVSWYQQHPGKAPKLMI
YEVSNRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4 antibody includes a common variable heavy domain (SEQ ID NO: 114) encoded by the nucleic acid sequence shown in SEQ ID NO: 113 and includes a lambda variable light domain (SEQ ID NO: 186) encoded by the nucleic acid sequence shown in SEQ ID NO: 185.

>KC4-VL-NT
(SEQ ID NO: 185)
CAGTCTGCCCTGACTCAGCCTGCCTCCGTGTCTGGGTCTCCTGGACAGTC
GATCACCATCTCCTGCACTGGAACCAGCAGTGACGTTGGTGGTTATAACT
ATGTCTCCTGGTACCAACAGCACCCAGGCAAAGCCCCCAAACTCATGATT
TATGAGGTCAGTAATCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4-VL-AA
(SEQ ID NO: 186)
QSALTQPASVSGSPGQSITISCTGTSSDVGGYNYVSWYQQHPGKAPKLMI
YEVSNRPSGVSNRFSGSKSGNTASLTISGLQAEDEADYYCSSYDWWFRPK
VFGGGTKLTVL

The Kc4G11 antibody includes a common heavy chain (SEQ ID NO: 2) encoded by the nucleic acid sequence shown in SEQ ID NO: 1 and includes a lambda light chain (SEQ ID NO: 76) encoded by the nucleic acid sequence shown in SEQ ID NO: 75.

>KC4G11-LC-NT
(SEQ ID NO: 75)
CAGTCTGCCCTGACTCAGCCTGCCTCCGTGTCTGGGTCTCCTGGACAGTC
GATCACCATCTCCTGCACTGGAACCAGCAGTGACGTTGGGAAGGCGAACT
ATGTCTCCTGGTACCAACAGCACCCAGGCAAAGCCCCCAAACTCATGATT
TATAAGGATAGTGATCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4G11-LC-AA
(SEQ ID NO: 76)
QSALTQPASVSGSPGQSITISCTGTSSDVGKANYVSWYQQHPGKAPKLMI
YKDSDRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4G11 antibody includes a common variable heavy domain (SEQ ID NO: 114) encoded by the nucleic acid sequence shown in SEQ ID NO: 113 and includes a lambda variable light domain (SEQ ID NO: 188) encoded by the nucleic acid sequence shown in SEQ ID NO: 187.

>KC4G11-VL-NT
(SEQ ID NO: 187)
CAGTCTGCCCTGACTCAGCCTGCCTCCGTGTCTGGGTCTCCTGGACAGTC
GATCACCATCTCCTGCACTGGAACCAGCAGTGACGTTGGGAAGGCGAACT
ATGTCTCCTGGTACCAACAGCACCCAGGCAAAGCCCCCAAACTCATGATT
TATAAGGATAGTGATCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4G11-VL-AA
(SEQ ID NO: 188)
QSALTQPASVSGSPGQSITISCTGTSSDVGKANYVSWYQQHPGKAPKLMI
YKDSDRPSGVSNRFSGSKSGNTASLTISGLQAEDEADYYCSSYDWWFRPK
VFGGGTKLTVL

The Kc4C11 antibody includes a common heavy chain (SEQ ID NO: 2) encoded by the nucleic acid sequence shown in SEQ ID NO: 1 and includes a lambda light chain (SEQ ID NO: 78) encoded by the nucleic acid sequence shown in SEQ ID NO: 77.

>KC4C11-LC-NT
(SEQ ID NO: 77)
CAGTCTGCCCTGACTCAGCCTGCCTCCGTGTCTGGGTCTCCTGGACAGTC
GATCACCATCTCCTGCACTGGAACCAGCAGTGACGTTAGGGGGAATAACT
ATGTCTCCTGGTACCAACAGCACCCAGGCAAAGCCCCCAAACTCATGATT
TATGAGAATAGTAAGCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4C11-LC-AA
(SEQ ID NO: 78)
QSALTQPASVSGSPGQSITISCTGTSSDVRGNNYVSWYQQHPGKAPKLMI
YENSKRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4C11 antibody includes a common variable heavy domain (SEQ ID NO: 114) encoded by the nucleic acid sequence shown in SEQ ID NO: 113 and includes a lambda variable light domain (SEQ ID NO: 190) encoded by the nucleic acid sequence shown in SEQ ID NO: 189.

>KC4C11-VL-NT
(SEQ ID NO: 189)
CAGTCTGCCCTGACTCAGCCTGCCTCCGTGTCTGGGTCTCCTGGACAGTC
GATCACCATCTCCTGCACTGGAACCAGCAGTGACGTTAGGGGGAATAACT
ATGTCTCCTGGTACCAACAGCACCCAGGCAAAGCCCCCAAACTCATGATT
TATGAGAATAGTAAGCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4C11-VL-AA
(SEQ ID NO: 190)
QSALTQPASVSGSPGQSITISCTGTSSDVRGNNYVSWYQQHPGKAPKLMI
YENSKRPSGVSNRFSGSKSGNTASLTISGLQAEDEADYYCSSYDWWFRPK
VFGGGTKLTVL

The Kc4A1 antibody includes a common heavy chain (SEQ ID NO: 2) encoded by the nucleic acid sequence shown in SEQ ID NO: 1 and includes a lambda light chain (SEQ ID NO: 80) encoded by the nucleic acid sequence shown in SEQ ID NO: 79.

>KC4A1-LC-NT
(SEQ ID NO: 79)
CAGTCTGCCCTGACTCAGCCTGCCTCCGTGTCTGGGTCTCCTGGACAGTC
GATCACCATCTCCTGCACTGGAACCAGCAGTGACGTTAGTGCGAGGAACT
ATGTCTCCTGGTACCAACAGCACCCAGGCAAAGCCCCCAAACTCATGATT
TATGAGAGTAGTAAGCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4A1-LC-AA
(SEQ ID NO: 80)
QSALTQPASVSGSPGQSITISCTGTSSDVSARNYVSWYQQHPGKAPKLMI
YESSKRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4A1 antibody includes a common variable heavy domain (SEQ ID NO: 114) encoded by the nucleic acid sequence shown in SEQ ID NO: 113 and includes a lambda variable light domain (SEQ ID NO: 192) encoded by the nucleic acid sequence shown in SEQ ID NO: 191.

>KC4A1-VL-NT
(SEQ ID NO: 191)
CAGTCTGCCCTGACTCAGCCTGCCTCCGTGTCTGGGTCTCCTGGACAGTC
GATCACCATCTCCTGCACTGGAACCAGCAGTGACGTTAGTGCGAGGAACT
ATGTCTCCTGGTACCAACAGCACCCAGGCAAAGCCCCCAAACTCATGATT
TATGAGAGTAGTAAGCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4A1-VL-AA
(SEQ ID NO: 192)
QSALTQPASVSGSPGQSITISCTGTSSDVSARNYVSWYQQHPGKAPKLMI
YESSKRPSGVSNRFSGSKSGNTASLTISGLQAEDEADYYCSSYDWWFRPK
VFGGGTKLTVL

The Kc4A4 antibody includes a common heavy chain (SEQ ID NO: 2) encoded by the nucleic acid sequence shown in SEQ ID NO: 1 and includes a lambda light chain (SEQ ID NO: 82) encoded by the nucleic acid sequence shown in SEQ ID NO: 81.

>KC4A4-LC-NT
(SEQ ID NO: 81)
CAGTCTGCCCTGACTCAGCCTGCCTCCGTGTCTGGGTCTCCTGGACAGTC
GATCACCATCTCCTGCACTAGAACCAGCAGTGACGTTAATAATACTAACT
ATGTCTCCTGGTACCAACAGCACCCAGGCAAAGCCCCCAAACTCATGATT
TATAAGACTAGTGGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4A4-LC-AA
(SEQ ID NO: 82)
QSALTQPASVSGSPGQSITISCTRTSSDVNNTNYVSWYQQHPGKAPKLMI
YKTSGRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPKQSNNKYAASSYLSLTPEQWKSHRSYSCQV
THEGSTVEKTVAPTECS

The Kc4A4 antibody includes a common variable heavy domain (SEQ ID NO: 114) encoded by the nucleic acid sequence shown in SEQ ID NO: 113 and includes a lambda variable light domain (SEQ ID NO: 194) encoded by the nucleic acid sequence shown in SEQ ID NO: 193.

>KC4A4-VL-NT
(SEQ ID NO: 193)
CAGTCTGCCCTGACTCAGCCTGCCTCCGTGTCTGGGTCTCCTGGACAGTC
GATCACCATCTCCTGCACTAGAACCAGCAGTGACGTTAATAATACTAACT
ATGTCTCCTGGTACCAACAGCACCCAGGCAAAGCCCCCAAACTCATGATT
TATAAGACTAGTGGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4A4-VL-AA
(SEQ ID NO: 194)
QSALTQPASVSGSPGQSITISCTRTSSDVNNTNYVSWYQQHPGKAPKLMI
YKTSGRPSGVSNRFSGSKSGNTASLTISGLQAEDEADYYCSSYDWWFRPK
VFGGGTKLTVL

The Kc4E10 antibody includes a common heavy chain (SEQ ID NO: 2) encoded by the nucleic acid sequence shown in SEQ ID NO: 1 and includes a lambda light chain (SEQ ID NO: 84) encoded by the nucleic acid sequence shown in SEQ ID NO: 83.

>KC4E10-LC-NT
(SEQ ID NO: 83)
CAGTCTGCCCTGACTCAGCCTGCCTCCGTGTCTGGGTCTCCTGGACAGTC
GATCACCATCTCCTGCACTGGAACCAGCAGTGACGTTAATTCTGCTAACT
ATGTCTCCTGGTACCAACAGCACCCAGGCAAAGCCCCCAAACTCATGATT
TATAAGAGTAGTAGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4E10-LC-AA
(SEQ ID NO: 84)
QSALTQPASVSGSPGQSITISCTGTSSDVNSANYVSWYQQHPGKAPKLMI
YKSSSRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPKQSNNKYAASSYLSLTPEQWKSHRSYSCQV
THEGSTVEKTVAPTECS

The Kc4E10 antibody includes a common variable heavy domain (SEQ ID NO: 114) encoded by the nucleic acid sequence shown in SEQ ID NO: 113 and includes a lambda variable light domain (SEQ ID NO: 196) encoded by the nucleic acid sequence shown in SEQ ID NO: 195.

>KC4E10-VL-NT
(SEQ ID NO: 195)
CAGTCTGCCCTGACTCAGCCTGCCTCCGTGTCTGGGTCTCCTGGACAGTC

GATCACCATCTCCTGCACTGGAACCAGCAGTGACGTTAATTCTGCTAACT

ATGTCTCCTGGTACCAACAGCACCCAGGCAAAGCCCCCAAACTCATGATT

TATAAGAGTAGTAGTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4E10-VL-AA
(SEQ ID NO: 196)
QSALTQPASVSGSPGQSITISCTGTSSDVNSANYVSWYQQHPGKAPKLMI

YKSSSRPSGVSNRFSGSKSGNTASLTISGLQAEDEADYYCSSYDWWFRPK

VFGGGTKLTVL

The Kc4G9 antibody includes a common heavy chain (SEQ ID NO: 2) encoded by the nucleic acid sequence shown in SEQ ID NO: 1 and includes a lambda light chain (SEQ ID NO: 86) encoded by the nucleic acid sequence shown in SEQ ID NO: 85.

>KC4G9-LC-NT
(SEQ ID NO: 85)
CAGTCTGCCCTGACTCAGCCTGCCTCCGTGTCCGGGTCTCCTGGACAGTC

GATCACCATCTCCTGCACTGGAACCAGCAGTGACGTTGAGAGGAAGAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4G9-LC-AA
(SEQ ID NO: 86)
QSALTQPASVSGSPGQSITISCTGTSSDVERKNYVSWYQQHPGKAPKLMI

YKNSTRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4G9 antibody includes a common variable heavy domain (SEQ ID NO: 114) encoded by the nucleic acid sequence shown in SEQ ID NO: 113 and includes a lambda variable light domain (SEQ ID NO: 198) encoded by the nucleic acid sequence shown in SEQ ID NO: 197.

>KC4G9-VL-NT
(SEQ ID NO: 197)
CAGTCTGCCCTGACTCAGCCTGCCTCCGTGTCCGGGTCTCCTGGACAGTC

GATCACCATCTCCTGCACTGGAACCAGCAGTGACGTTGAGAGGAAGAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4G9-VL-AA
(SEQ ID NO: 198)
QSALTQPASVSGSPGQSITISCTGTSSDVERKNYVSWYQQHPGKAPKLMI

YKNSTRPSGVSNRFSGSKSGNTASLTISGLQAEDEADYYCSSYDWWFRPK

VFGGGTKLTVL

The Kc4C3 antibody includes a common heavy chain (SEQ ID NO: 2) encoded by the nucleic acid sequence shown in SEQ ID NO: 1 and includes a lambda light chain (SEQ ID NO: 88) encoded by the nucleic acid sequence shown in SEQ ID NO: 87.

>KC4C3-LC-NT
(SEQ ID NO: 87)
CAGTCTGCCCTGACTCAGCCTGCCTCCGTGTCTGGGTCTCCTGGACAGTC

GATCACCATCTCCTGCACTGGAACCAGCAGTGACGTTAGGGCGGCTAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4C3-LC-AA
(SEQ ID NO: 88)
QSALTQPASVSGSPGQSITISCTGTSSDVRAANYVSWYQQHPGKAPKLMI

YKNSTRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4C3 antibody includes a common variable heavy domain (SEQ ID NO: 114) encoded by the nucleic acid sequence shown in SEQ ID NO: 113 and includes a lambda variable light domain (SEQ ID NO: 200) encoded by the nucleic acid sequence shown in SEQ ID NO: 199.

>KC4C3-VL-NT (SEQ ID NO: 199)

CAGTCTGCCCTGACTCAGCCTGCCTCCGTGTCTGGGTCTCCTGGACAGTC

GATCACCATCTCCTGCACTGGAACCAGCAGTGACGTTAGGGCGGCTAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4C3-VL-AA (SEQ ID NO: 200)

QSALTQPASVSGSPGQSITISCTGTSSDVRAANYVSWYQQHPGKAPKLMI

YKNSTRPSGVSNRFSGSKSGNTASLTISGLQAEDEADYYCSSYDWWFRPK

VFGGGTKLTVL

The Kc4F4 antibody includes a common heavy chain (SEQ ID NO: 2) encoded by the nucleic acid sequence shown in SEQ ID NO: 1 and includes a lambda light chain (SEQ ID NO: 90) encoded by the nucleic acid sequence shown in SEQ ID NO: 89.

>KC4F4-LC-NT (SEQ ID NO: 89)

CAGTCTGCCCTGACTCAGCCTGCCTCCGTGTCTGGGTCTCCTGGACAGTC

GATCACCATCTCCTGCACTGGAACCAGCAGTGACGTTAGGAGGGCTAACT

ATGTCTCCTGGTACCAACAGCACCCAGGCAAAGCCCCCAAACTCATGATT

TATCAGGATAGTAGTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4F4-LC-AA (SEQ ID NO: 90)

QSALTQPASVSGSPGQSITISCTGTSSDVRRANYVSWYQQHPGKAPKLMI

YQDSSRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4F4 antibody includes a common variable heavy domain (SEQ ID NO: 114) encoded by the nucleic acid sequence shown in SEQ ID NO: 113 and includes a lambda variable light domain (SEQ ID NO: 202) encoded by the nucleic acid sequence shown in SEQ ID NO: 201.

>KC4F4-VL-NT (SEQ ID NO: 201)

CAGTCTGCCCTGACTCAGCCTGCCTCCGTGTCTGGGTCTCCTGGACAGTC

GATCACCATCTCCTGCACTGGAACCAGCAGTGACGTTAGGAGGGCTAACT

ATGTCTCCTGGTACCAACAGCACCCAGGCAAAGCCCCCAAACTCATGATT

TATCAGGATAGTAGTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4F4-VL-AA (SEQ ID NO: 202)

QSALTQPASVSGSPGQSITISCTGTSSDVRRANYVSWYQQHPGKAPKLMI

YQDSSRPSGVSNRFSGSKSGNTASLTISGLQAEDEADYYCSSYDWWFRPK

VFGGGTKLTVL

The Kc4B1 antibody includes a common heavy chain (SEQ ID NO: 2) encoded by the nucleic acid sequence shown in SEQ ID NO: 1 and includes a lambda light chain (SEQ ID NO: 92) encoded by the nucleic acid sequence shown in SEQ ID NO: 91.

>KC4B1-LC-NT (SEQ ID NO: 91)

CAGTCTGCCCTGACTCAGCCTGCCTCCGTGTCTGGGTCTCCTGGACAGTC

GATCACCATCTCCTGCACTGGAACCAGCAGTGACGTTAGGGCTAATAACT

ATGTCTCCTGGTACCAACAGCACCCAGGCAAAGCCCCCAAACTCATGATT

TATGAGAGTAGTGCGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4B1-LC-AA (SEQ ID NO: 92)

QSALTQPASVSGSPGQSITISCTGTSSDVRANNYVSWYQQHPGKAPKLMI

YESSARPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4B1 antibody includes a common variable heavy domain (SEQ ID NO: 114) encoded by the nucleic acid sequence shown in SEQ ID NO: 113 and includes a lambda variable light domain (SEQ ID NO: 204) encoded by the nucleic acid sequence shown in SEQ ID NO: 203.

>KC4B1-VL-NT (SEQ ID NO: 203)

CAGTCTGCCCTGACTCAGCCTGCCTCCGTGTCTGGGTCTCCTGGACAGTC

GATCACCATCTCCTGCACTGGAACCAGCAGTGACGTTAGGGCTAATAACT

ATGTCTCCTGGTACCAACAGCACCCAGGCAAAGCCCCCAAACTCATGATT

TATGAGAGTAGTGCGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4B1-VL-AA (SEQ ID NO: 204)

QSALTQPASVSGSPGQSITISCTGTSSDVRANNYVSWYQQHPGKAPKLMI

YESSARPSGVSNRFSGSKSGNTASLTISGLQAEDEADYYCSSYDWWFRPK

VFGGGTKLTVL

The Kc4E2 antibody includes a common heavy chain (SEQ ID NO: 2) encoded by the nucleic acid sequence shown in SEQ ID NO: 1 and includes a lambda light chain (SEQ ID NO: 94) encoded by the nucleic acid sequence shown in SEQ ID NO: 93.

>KC4E2-LC-NT (SEQ ID NO: 93)

CAGTCTGCCCTGACTCAGCCTGCCTCCGTGTCTGGGTCTCCTGGACAGTC

GATCACCATCTCCTGCACTGGAACCAGCAGTGACGTTTATTATAATAAGT

ATGTCTCCTGGTACCAACAGCACCCAGGCAAAGCCCCCAAACTCATGATT

TATGAGAGTAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4E2-LC-AA (SEQ ID NO: 94)

QSALTQPASVSGSPGQSITISCTGTSSDVYYNKYVSWYQQHPGKAPKLMI

YESSKRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4E2 antibody includes a common variable heavy domain (SEQ ID NO: 114) encoded by the nucleic acid sequence shown in SEQ ID NO: 113 and includes a lambda variable light domain (SEQ ID NO: 96) encoded by the nucleic acid sequence shown in SEQ ID NO: 95.

>KC4E2-VL-NT (SEQ ID NO: 95)

CAGTCTGCCCTGACTCAGCCTGCCTCCGTGTCTGGGTCTCCTGGACAGTC

GATCACCATCTCCTGCACTGGAACCAGCAGTGACGTTTATTATAATAAGT

ATGTCTCCTGGTACCAACAGCACCCAGGCAAAGCCCCCAAACTCATGATT

TATGAGAGTAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4E2-VL-AA (SEQ ID NO: 96)

QSALTQPASVSGSPGQSITISCTGTSSDVYYNKYVSWYQQHPGKAPKLMI

YESSKRPSGVSNRFSGSKSGNTASLTISGLQAEDEADYYCSSYDWWFRPK

VFGGGTKLTVL

Anti-Mesothelin (Anti-MSLN) Antibodies

The O25 antibody includes a common heavy chain (SEQ ID NO: 2) encoded by the nucleic acid sequence shown in SEQ ID NO: 1 and includes a lambda light chain (SEQ ID NO: 98) encoded by the nucleic acid sequence shown in SEQ ID NO: 97. The variable region of the lambda light chain is bolded in the amino acid sequence below.

>O25-LC-NT (SEQ ID NO: 97)

CAGCCTGTGCTGACTCAGCCGGCTTCCCTCTCTGCATCTCCTGGAGCATC

AGCCAGTCTCACCTGCACCTTGCACAGTGGCATCTCTGTTAAGGATTACA

GGATATACTGGTACCAGCAGAAGCCAGGGCGTCCTCCCCAGTATCTCCTG

AGGTACAAGTCTAATTCAGATATGCAGCAGGGATCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CATGGCCATGGGACTAGTCTTGTGTTCGGCGGAGGGACCAAGCTGACCGT

CCTAGGTCAGCCCAAGGCTGCCCCCTCGGTCACTCTGTTCCCGCCCTCCT

CTGAGGAGCTTCAAGCCAACAAGGCCACACTGGTGTGTCTCATAAGTGAC

TTCTACCCGGGAGCCGTGACAGTGGCTTGGAAAGCAGATAGCAGCCCCGT

CAAGGCGGGAGTGGAGACCACCACACCCTCCAAACAAAGCAACAACAAGT

ACGCGGCCAGCAGCTATCTGAGCCTGACGCCTGAGCAGTGGAAGTCCCAC

AGAAGCTACAGCTGCCAGGTCACGCATGAAGGGAGCACCGTGGAGAAGAC

AGTGGCCCCTACAGAATGTTCATAA

>O25-LC-AA (SEQ ID NO: 98)

QPVLTQPASLSASPGASASLTCTLHSGISVKDYRIYWYQQKPGRPPQYLL

RYKSNSDMQQGSGVPSRFSGSKDASANAGILLISGLQSEDEADYYCMIWH

HGHGTSLVFGGGTKLTVLGQPKAAPSVTLFPPSSEELQANKATLVCLISD

FYPGAVTVAWKADSSPVKAGVETTTPSKQSNNKYAASSYLSLTPEQWKSH

RSYSCQVTHEGSTVEKTVAPTECS

The O25 antibody includes a common variable heavy domain (SEQ ID NO: 114) encoded by the nucleic acid sequence shown in SEQ ID NO: 113 and includes a lambda variable light domain (SEQ ID NO: 212) encoded by the nucleic acid sequence shown in SEQ ID NO: 211.

>O25-VH-NT (SEQ ID NO: 211)
CAGCCTGTGCTGACTCAGCCGGCTTCCCTCTCTGCATCTCCTGGAGCATC

AGCCAGTCTCACCTGCACCTTGCACAGTGGCATCTCTGTTAAGGATTACA

GGATATACTGGTACCAGCAGAAGCCAGGGCGTCCTCCCCAGTATCTCCTG

AGGTACAAGTCTAATTCAGATATGCAGCAGGGATCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CATGGCCATGGGACTAGTCTTGTGTTCGGCGGAGGGACCAAGCTGACCGT

CCTA

>O25-VH-AA (SEQ ID NO: 212)
QPVLTQPASLSASPGASASLTCTLHSGISVKDYRIYWYQQKPGRPPQYLL

RYKSNSDMQQGSGVPSRFSGSKDASANAGILLISGLQSEDEADYYCMIWH

HGHGTSLVFGGGTKLTVL

The O30 antibody includes a common heavy chain (SEQ ID NO: 2) encoded by the nucleic acid sequence shown in SEQ ID NO: 1 and includes a lambda light chain (SEQ ID NO: 100) encoded by the nucleic acid sequence shown in SEQ ID NO: 99. The variable region of the lambda light chain is bolded in the amino acid sequence below.

>O30-LC-NT (SEQ ID NO: 99)
CAGTCTGTGCTGACTCAGCCACCCTCAGCGTCTGGGACCCCCGGGCAGAG

GGTCACCATCTCTTGTTCTGGAAGCAGCTCCAACATCGCGCATGGGCCTG

TAAACTGGTACCAGCAGCTCCCAGGAACGGCCCCCAAACTCCTCATCTAT

GCTACTAATCATCGGCCCTCAGGGGTCCCTGACCGATTTTCTGGCTCCAA

GTCTGGCACCACAGCCTCCCTGACCATCAGTGGGCTCCAGTCTGAGGATG

AGGCTGATTATTACTGTGCTGCATATGATCTTACGGGCTGGTTTGCGTAT

GCTGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>O30-LC-AA (SEQ ID NO: 100)
QSVLTQPPSASGTPGQRVTISCSGSSSNIAHGPVNWYQQLPGTAPKLLIY

ATNHRPSGVPDRFSGSKSGTTASLTISGLQSEDEADYYCAAYDLTGWFAY

AVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS

The O30 antibody includes a common variable heavy domain (SEQ ID NO: 114) encoded by the nucleic acid sequence shown in SEQ ID NO: 113 and includes a lambda variable light domain (SEQ ID NO: 214) encoded by the nucleic acid sequence shown in SEQ ID NO: 213.

>O30-VL-NT (SEQ ID NO: 213)
CAGTCTGTGCTGACTCAGCCACCCTCAGCGTCTGGGACCCCCGGGCAGAG

GGTCACCATCTCTTGTTCTGGAAGCAGCTCCAACATCGCGCATGGGCCTG

TAAACTGGTACCAGCAGCTCCCAGGAACGGCCCCCAAACTCCTCATCTAT

GCTACTAATCATCGGCCCTCAGGGGTCCCTGACCGATTTTCTGGCTCCAA

GTCTGGCACCACAGCCTCCCTGACCATCAGTGGGCTCCAGTCTGAGGATG

AGGCTGATTATTACTGTGCTGCATATGATCTTACGGGCTGGTTTGCGTAT

GCTGTGTTCGGCGGAGGGACCAAGCTGACCGTCCTAGGTCAGCCCAAGGC

TGCCCCCTCGGTCACTCTG

>O30-VL-AA (SEQ ID NO: 214)
QSVLTQPPSASGTPGQRVTISCSGSSSNIAHGPVNWYQQLPGTAPKLLIY

ATNHRPSGVPDRFSGSKSGTTASLTISGLQSEDEADYYCAAYDLTGWFAY

AVFGGGTKLTVLGQPKAAPSVTL

The O32 antibody includes a common heavy chain (SEQ ID NO: 2) encoded by the nucleic acid sequence shown in SEQ ID NO: 1 and includes a lambda light chain (SEQ ID NO: 102) encoded by the nucleic acid sequence shown in SEQ ID NO: 101. The variable region of the lambda light chain is bolded in the amino acid sequence below.

>O32-LC-NT (SEQ ID NO: 101)
TCCTATGTGCTGACTCAGCCACCCTCAGTGTCAGTGGCCCCAGGAAAGAC

GGCCAGGATTACCTGTGGGGGAAACAAGATTGGACACCGCCGTGCACT

GGTACCAGCAGAAGCCAGGCCAGGCCCCTGTGCTGGTCATCTATTATACC

TATGATCGGCCCTCAGGGATTCCTGAGCGATTCTCTGGCTCCAACTCTGG

GAACACGGCCACCCTGACCATCAGCAGGGTCGAAGCCGGGGATGAGGCCG

ACTATTACTGTCAGGTGTGGGATGCGTCTAGGCGCGACGCGAATGTTGTG

TTCGGCGGAGGGACCAAGCTGACCGTCCTAGGTCAGCCCAAGGCTGCCCC

CTCGGTCACTCTGTTCCCGCCCTCCTCTGAGGAGCTTCAAGCCAACAAGG

CCACACTGGTGTGTCTCATAAGTGACTTCTACCCGGGAGCCGTGACAGTG

GCTTGGAAAGCAGATAGCAGCCCCGTCAAGGCGGGAGTGGAGACCACCAC

ACCCTCCAAACAAAGCAACAACAAGTACGCGGCCAGCAGCTATCTGAGCC

TGACGCCTGAGCAGTGGAAGTCCCACAGAAGCTACAGCTGCCAGGTCACG

CATGAAGGGAGCACCGTGGAGAAGACAGTGGCCCCTACAGAATGTTCATA

A

>O32-LC-AA (SEQ ID NO: 102)
SYVLTQPPSVSVAPGKTARITCGGNKIGHRAVHWYQQKPGQAPVLVIYYT

YDRPSGIPERFSGSNSGNTATLTISRVEAGDEADYYCQVWDASRRDANVV

FGGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPTECS

The O32 antibody includes a common variable heavy domain (SEQ ID NO: 114) encoded by the nucleic acid sequence shown in SEQ ID NO: 113 and includes a lambda variable light domain (SEQ ID NO: 216) encoded by the nucleic acid sequence shown in SEQ ID NO: 215.

>O32-VL-NT
(SEQ ID NO: 215)
TCCTATGTGCTGACTCAGCCACCCTCAGTGTCAGTGGCCCCAGGAAAGAC

GGCCAGGATTACCTGTGGGGGAAACAAGATTGGACACCGCGCCGTGCACT

GGTACCAGCAGAAGCCAGGCCAGGCCCCTGTGCTGGTCATCTATTATACC

TATGATCGGCCCTCAGGGATTCCTGAGCGATTCTCTGGCTCCAACTCTGG

GAACACGGCCACCCTGACCATCAGCAGGGTCGAAGCCGGGGATGAGGCCG

ACTATTACTGTCAGGTGTGGGATGCGTCTAGGCGCGACGCGAATGTTGTG

TTCGGCGGAGGGACCAAGCTGACCGTCCTAGGTCAGCCCAAGGCTGCCCC

CTCGGTCACTCTG

>O32-VL-AA
(SEQ ID NO: 216)
SYVLTQPPSVSVAPGKTARITCGGNKIGHRAVHWYQQKPGQAPVLVIYYT

YDRPSGIPERFSGSNSGNTATLTISRVEAGDEADYYCQVWDASRRDANVV

FGGGTKLTVLGQPKAAPSVTL

The O35 antibody includes a common heavy chain (SEQ ID NO: 2) encoded by the nucleic acid sequence shown in SEQ ID NO: 1 and includes a lambda light chain (SEQ ID NO: 104) encoded by the nucleic acid sequence shown in SEQ ID NO: 103. The variable region of the lambda light chain is bolded in the amino acid sequence below.

>O35-LC-NT
(SEQ ID NO: 103)
CAGCCTGTGCTGACTCAGCCGGTTTCCCTCTCTGCATCTCCTGGAGCATC

AGTCAGTCTCACCTGCACCTTGCGCAGTGACATCAGGGTTAGAGATTACA

GGATATTCTGGTACCAGCAGAAGCCAGGGAGTCCTCCCCAGTATCTCCTG

AGGTACAAAACCGACTCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CGCACCACGGGCACTAGTCTTGTGTTCGGCGGAGGGACCAAGCTGACCGT

CCTAGGTCAGCCCAAGGCTGCCCCCTCGGTCACTCTGTTCCCGCCCTCCT

CTGAGGAGCTTCAAGCCAACAAGGCCACACTGGTGTGTCTCATAAGTGAC

TTCTACCCGGGAGCCGTGACAGTGGCTTGGAAAGCAGATAGCAGCCCGT

CAAGGCGGGAGTGGAGACCACCACACCCTCCAAACAAAGCAACAACAAGT

ACGCGGCCAGCAGCTATCTGAGCCTGACGCCTGAGCAGTGGAAGTCCCAC

AGAAGCTACAGCTGCCAGGTCACGCATGAAGGGAGCACCGTGGAGAAGAC

AGTGGCCCCTACAGAATGTTCATAA

>O35-LC-AA
(SEQ ID NO: 104)
QPVLTQPVSLSASPGASVSLTCTLRSDIRVRDYRIFWYQQKPGSPPQYLL

RYKTDSDKQQGSGVPSRFSGSKDASANAGILLISGLQSEDEADYYCMIWH

RTTGTSLVFGGGTKLTVLGQPKAAPSVTLFPPSSEELQANKATLVCLISD

FYPGAVTVAWKADSSPVKAGVETTTPSKQSNNKYAASSYLSLTPEQWKSH

RSYSCQVTHEGSTVEKTVAPTECS

The O35 antibody includes a common variable heavy domain (SEQ ID NO: 114) encoded by the nucleic acid sequence shown in SEQ ID NO: 113 and includes a lambda variable light domain (SEQ ID NO: 218) encoded by the nucleic acid sequence shown in SEQ ID NO: 217.

>O35-VL-NT
(SEQ ID NO: 217)
CAGCCTGTGCTGACTCAGCCGGTTTCCCTCTCTGCATCTCCTGGAGCATC

AGTCAGTCTCACCTGCACCTTGCGCAGTGACATCAGGGTTAGAGATTACA

GGATATTCTGGTACCAGCAGAAGCCAGGGAGTCCTCCCCAGTATCTCCTG

AGGTACAAAACCGACTCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CGCACCACGGGCACTAGTCTTGTGTTCGGCGGAGGGACCAAGCTGACCGT

CCTA

>O35-VL-AA
(SEQ ID NO: 218)
QPVLTQPVSLSASPGASVSLTCTLRSDIRVRDYRIFWYQQKPGSPPQYLL

RYKTDSDKQQGSGVPSRFSGSKDASANAGILLISGLQSEDEADYYCMIWH

RTTGTSLVFGGGTKLTVL

The O37 antibody includes a common heavy chain (SEQ ID NO: 2) encoded by the nucleic acid sequence shown in SEQ ID NO: 1 and includes a lambda light chain (SEQ ID NO: 106) encoded by the nucleic acid sequence shown in SEQ ID NO: 105. The variable region of the lambda light chain is bolded in the amino acid sequence below.

>O37-LC-NT
(SEQ ID NO: 105)
CAGCCTGTGCTGACTCAGCCGGCTTCCCTCTCTGCATCTCCTGGAGCATC

AGCCAGTCTCACCTGCACCTTGCGCAGTGGCATCAACGTTAAGGATTACA

GGATATTCTGGTACCAGCAGAAGCAGGGAGTCCTCCCCAGTATCTCCTG

AGGTACAAAAGCGAATCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

AAGGATCGGGAGGGGCATGCTTTTGTGTTCGGCGGAGGGACCAAGCTGAC

CGTCCTAGGTCAGCCCAAGGCTGCCCCCTCGGTCACTCTGTTCCCGCCCT

CCTCTGAGGAGCTTCAAGCCAACAAGGCCACACTGGTGTGTCTCATAAGT

GACTTCTACCCGGGAGCCGTGACAGTGGCTTGGAAAGCAGATAGCAGCCC

CGTCAAGGCGGGAGTGGAGACCACCACACCCTCCAAACAAAGCAACAACA

AGTACGCGGCCAGCAGCTATCTGAGCCTGACGCCTGAGCAGTGGAAGTCC

CACAGAAGCTACAGCTGCCAGGTCACGCATGAAGGGAGCACCGTGGAGAA

GACAGTGGCCCCTACAGAATGTTCATAA

>O37-LC-AA
(SEQ ID NO: 106)
QPVLTQPASLSASPGASASLTCTLRSGINVKDYRIFWYQQKPGSPPQYLL

RYKSESDKQQGSGVPSRFSGSKDASANAGILLISGLQSEDEADYYCMIWH

KDREGHAFVFGGGTKLTVLGQPKAAPSVTLFPPSSEELQANKATLVCLIS

DFYPGAVTVAWKADSSPVKAGVETTTPSKQSNNKYAASSYLSLTPEQWKS

HRSYSCQVTHEGSTVEKTVAPTECS

The O37 antibody includes a common variable heavy domain (SEQ ID NO: 114) encoded by the nucleic acid sequence shown in SEQ ID NO: 113 and includes a lambda variable light domain (SEQ ID NO: 220) encoded by the nucleic acid sequence shown in SEQ ID NO: 219.

>O37-VL-NT
(SEQ ID NO: 219)
CAGCCTGTGCTGACTCAGCCGGCTTCCCTCTCTGCATCTCCTGGAGCATC
AGCCAGTCTCACCTGCACCTTGCGCAGTGGCATCAACGTTAAGGATTACA
GGATATTCTGGTACCAGCAGAAGCCAGGGAGTCCTCCCCAGTATCTCCTG
AGGTACAAAAGCGAATCAGATAAGCAGCAGGGCTCTGGAGTCCCCAGCCG
CTTCTCTGGGTCCAAAGATGCTTCGGCCAATGCAGGGATTTTACTCATCT
CTGGGCTCCAGTCTGAGGATGAGGCTGACTATTACTGTATGATTTGGCAC
AAGGATCGGGAGGGGCATGCTTTTGTGTTCGGCGGAGGGACCAAGCTGAC
CGTCCTA

>O37-VL-AA
(SEQ ID NO: 220)
QPVLTQPASLSASPGASASLTCTLRSGINVKDYRIFWYQQKPGSPPQYLL
RYKSESDKQQGSGVPSRFSGSKDASANAGILLISGLQSEDEADYYCMIWH
KDREGHAFVFGGGTKLTVL

The O38 antibody includes a common heavy chain (SEQ ID NO: 2) encoded by the nucleic acid sequence shown in SEQ ID NO: 1 and includes a lambda light chain (SEQ ID NO: 108) encoded by the nucleic acid sequence shown in SEQ ID NO: 107. The variable region of the lambda light chain is bolded in the amino acid sequence below.

>O38-LC-NT
(SEQ ID NO: 107)
CAGCCTGTGCTGACTCAGCCGGCTTCCCTCTCTGCATCTCCTGGGCATC
AGCCAGTCTCACCTGCACCTTGCGCAGTGGCATCAACGTTAGAGATTACA
GGATATTCTGGTACCAGCAGAAGCCAGGGAGTCCTCCCCAGTATCTCCTG
AGGTACAAAAGCGCATCAGATAAGCAGCAGGGCTCTGGAGTCCCCAGCCG
CTTCTCTGGGTCCAAAGATGCTTCGGCCAATGCAGGGATTTTACTCATCT
CTGGGCTCCAGTCTGAGGATGAGGCTGACTATTACTGTATGATTTGGCAC
CACGATTCGGAGGGGCATGCTTTTGTGTTCGGCGGAGGGACCAAGCTGAC
CGTCCTAGGTCAGCCCAAGGCTGCCCCCTCGGTCACTCTGTTCCCGCCCT
CCTCTGAGGAGCTTCAAGCCAACAAGGCCACACTGGTGTGTCTCATAAGT
GACTTCTACCCGGGAGCCGTGACAGTGGCTTGGAAAGCAGATAGCAGCCC
CGTCAAGGCGGGAGTGGAGACCACCACACCCTCCAAACAAAGCAACAACA
AGTACGCGGCCAGCAGCTATCTGAGCCTGACGCCTGAGCAGTGGAAGTCC
CACAGAAGCTACAGCTGCCAGGTCACGCATGAAGGGAGCACCGTGGAGAA
GACAGTGGCCCCTACAGAATGTTCATAA

>O38-LC-AA
(SEQ ID NO: 108)
QPVLTQPASLSASPGASASLTCTLRSGINVRDYRIFWYQQKPGSPPQYLL
RYKSASDKQQGSGVPSRFSGSKDASANAGILLISGLQSEDEADYYCMIWH
HDSEGHAFVFGGGTKLTVLGQPKAAPSVTLFPPSSEELQANKATLVCLIS
DFYPGAVTVAWKADSSPVKAGVETTTPSKQSNNKYAASSYLSLTPEQWKS
HRSYSCQVTHEGSTVEKTVAPTECS

The O38 antibody includes a common variable heavy domain (SEQ ID NO: 114) encoded by the nucleic acid sequence shown in SEQ ID NO: 113 and includes a lambda variable light domain (SEQ ID NO: 222) encoded by the nucleic acid sequence shown in SEQ ID NO: 221.

>O38-VL-NT
(SEQ ID NO: 221)
CAGCCTGTGCTGACTCAGCCGGCTTCCCTCTCTGCATCTCCTGGGCATC
AGCCAGTCTCACCTGCACCTTGCGCAGTGGCATCAACGTTAGAGATTACA
GGATATTCTGGTACCAGCAGAAGCCAGGGAGTCCTCCCCAGTATCTCCTG
AGGTACAAAAGCGCATCAGATAAGCAGCAGGGCTCTGGAGTCCCCAGCCG
CTTCTCTGGGTCCAAAGATGCTTCGGCCAATGCAGGGATTTTACTCATCT
CTGGGCTCCAGTCTGAGGATGAGGCTGACTATTACTGTATGATTTGGCAC
CACGATTCGGAGGGGCATGCTTTTGTGTTCGGCGGAGGGACCAAGCTGAC
CGTCCTA

>O38-VL-AA
(SEQ ID NO: 222)
QPVLTQPASLSASPGASASLTCTLRSGINVRDYRIFWYQQKPGSPPQYLL
RYKSASDKQQGSGVPSRFSGSKDASANAGILLISGLQSEDEADYYCMIWH
HDSEGHAFVFGGGTKLTVL

The O41 antibody includes a common heavy chain (SEQ ID NO: 2) encoded by the nucleic acid sequence shown in SEQ ID NO: 1 and includes a lambda light chain (SEQ ID NO: 110) encoded by the nucleic acid sequence shown in SEQ ID NO: 109. The variable region of the lambda light chain is bolded in the amino acid sequence below.

>O41-LC-NT
(SEQ ID NO: 109)
TCCTATGTGCTGACTCAGCCACCCTCAGTGTCAGTGGCCCCAGGAAAGAC
GGCCAGGATTACCTGTGGGGGAAACAAAATTGGACACCGCGCCGTGCACT
GGTACCAGCAGAAGCCAGGCCAGGCCCCTGTGCTGGTCATCTATTATACC
TATGAGCGGCCCTCAGGGATTCCTGAGCGATTCTCTGGCTCCAACTCTGG
GAACACGGCCACCCTGACCATCAGCAGGGTCGAAGCCGGGGATGAGGCCG
ACTATTACTGTCAGGTGTGGGATTGGTACAGCGAGGGGGGGGTTGTGTTC
GGCGGAGGGACCAAGCTGACCGTCCTAGGTCAGCCCAAGGCTGCCCCCTC
GGTCACTCTGTTCCCGCCCTCCTCTGAGGAGCTTCAAGCCAACAAGGCCA
CACTGGTGTGTCTCATAAGTGACTTCTACCCGGGAGCCGTGACAGTGGCT
TGGAAAGCAGATAGCAGCCCCGTCAAGGCGGGAGTGGAGACCACCACACC
CTCCAAACAAAGCAACAACAAGTACGCGGCCAGCAGCTATCTGAGCCTGA
CGCCTGAGCAGTGGAAGTCCCACAGAAGCTACAGCTGCCAGGTCACGCAT
GAAGGGAGCACCGTGGAGAAGACAGTGGCCCCTACAGAATGTTCATAA

>O41-LC-AA
(SEQ ID NO: 110)
SYVLTQPPSVSVAPGKTARITCGGNKIGHRAVHWYQQKPGQAPVLVIYYT
YERPSGIPERFSGSNSGNTATLTISRVEAGDEADYYCQVWDWYSEGGVVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

The O41 antibody includes a common variable heavy domain (SEQ ID NO: 114) encoded by the nucleic acid sequence shown in SEQ ID NO: 113 and includes a lambda variable light domain (SEQ ID NO: 224) encoded by the nucleic acid sequence shown in SEQ ID NO: 223.

>O41-VL-NT
(SEQ ID NO: 223)
TCCTATGTGCTGACTCAGCCACCCTCAGTGTCAGTGGCCCCAGGAAA

GACGGCCAGGATTACCTGTGGGGGAAACAAAATTGGACACCGCGCC

GTGCACTGGTACCAGCAGAAGCCAGGCCAGGCCCCTGTGCTGGTCA

TCTATTATACCTATGAGCGGCCCTCAGGGATTCCTGAGCGATTCTCTG

GCTCCAACTCTGGGAACACGGCCACCCTGACCATCAGCAGGGTCGA

AGCCGGGGATGAGGCCGACTATTACTGTCAGGTGTGGGATTGGTACA

GCGAGGGGGGGTTGTGTTCGGCGGAGGGACCAAGCTGACCGTCCT

AGGTCAGCCCAAGGCTGCCCCCTCGGTCACTCTG

>O41-VL-AA
(SEQ ID NO: 224)
SYVLTQPPSVSVAPGKTARITCGGNKIGHRAVHWYQQKPGQAPVLVIYYT

YERPSGIPERFSGSNSGNTATLTISRVEAGDEADYYCQVWDWYSEGGVVF

GGGTKLTVLGQPKAAPSVTL

Dummy Light Chains

The Dummy light chain 1 (SEQ ID NO: 112) is encoded by the nucleic acid sequence shown in SEQ ID NO: 111.

>DUMMY-LC1-NT
(SEQ ID NO: 111)
CAGTCTGTGTTGACGCAGCCGCCCTCAGTGTCTGCGGCCCCAGGACAGAA

GGTCACCATCTCCTGCTCTGGAAGCAGCTCCAATATTGAGACTGGTTCTG

TATCCTGGTACCAGCAGCTCCCAGGAACAGCCCCCAAACTCCTCATTTAT

GACAATAATAAGCGACCCTCAGGGATTCCTGACCGATTCTCTGGCTCCAA

GTCTGGCACGTCAGCCACCCTGGGCATCACCGGACTCCAGACTGGGACG

AGGCCGATTATTACTGCGGAACATGGGATGACAGCCTGCCTGGATGGGTG

TTCGGCGGAGGGACCAAGCTGACCGTCCTAGGTCAGCCCAAGGCTGCCCC

CTCGGTCACTCTGTTCCCGCCCTCCTCTGAGGAGCTTCAAGCCAACAAGG

CCACACTGGTGTGTCTCATAAGTGACTTCTACCCGGGAGCCGTGACAGTG

GCTTGGAAAGCAGATAGCAGCCCCGTCAAGGCGGGAGTGGAGACCACCAC

ACCCTCCAAACAAAGCAACAACAAGTACGCGGCCAGCAGCTATCTGAGCC

TGACGCCTGAGCAGTGGAAGTCCCACAGAAGCTACAGCTGCCAGGTCACG

CATGAAGGGAGCACCGTGGAGAAGACAGTGGCCCCTACAGAATGTTCATA

A

>DUMMY-LC1-AA
(SEQ ID NO: 112)
QSVLTQPPSVSAAPGQKVTISCSGSSSNIETGSVSWYQQLPGTAPKLLIY

DNNKRPSGIPDRFSGSKSGTSATLGITGLQTGDEADYYCGTWDDSLPGWV

FGGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPTECS

The Dummy variable light domain 1 (SEQ ID NO: 206) is encoded by the nucleic acid sequence shown in SEQ ID NO: 205.

>DUMMY-VL1-NT
(SEQ ID NO: 205)
CAGTCTGTGTTGACGCAGCCGCCCTCAGTGTCTGCGGCCCCAGGACAGAA

GGTCACCATCTCCTGCTCTGGAAGCAGCTCCAATATTGAGACTGGTTCTG

TATCCTGGTACCAGCAGCTCCCAGGAACAGCCCCCAAACTCCTCATTTAT

GACAATAATAAGCGACCCTCAGGGATTCCTGACCGATTCTCTGGCTCCAA

GTCTGGCACGTCAGCCACCCTGGGCATCACCGGACTCCAGACTGGGACG

AGGCCGATTATTACTGCGGAACATGGGATGACAGCCTGCCTGGATGGGTG

TTCGGCGGAGGGACCAAGCTGACCGTCCTA

>DUMMY-VL1-AA
(SEQ ID NO: 206)
QSVLTQPPSVSAAPGQKVTISCSGSSSNIETGSVSWYQQLPGTAPKLLIY

DNNKRPSGIPDRFSGSKSGTSATLGITGLQTGDEADYYCGTWDDSLPGWV

FGGGTKLTVL

The Dummy light chain 2 (SEQ ID NO: 208) is encoded by the nucleic acid sequence shown in SEQ ID NO: 207.

>DUMMY-LC2-NT
(SEQ ID NO: 207)
GAAATAGTGATGACGCAGTCTCCAGCCACCCTGTCTGTGTCTCCAGGGGA

AAGAGCCACCCTCTCCTGCAGGGCCAGTCAGACGGTTAAGAATAATTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAACAACTGGTTGCCCATCAACCCCTAT

ACCTTCGGCCAAGGGACCAAGGTGGAAATCAAACGTACGGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAA

>DUMMY-LC2-AA
(SEQ ID NO: 208)
EIVMTQSPATLSVSPGERATLSCRASQTVKNNLAWYQQKPGQAPRLLIYG

ASTRATGIPARFSGSGSGTEFTLTISSLQSEDFAVYYCQQYNNWLPINPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The Dummy variable light domain 2 (SEQ ID NO: 210) is encoded by the nucleic acid sequence shown in SEQ ID NO: 209.

>DUMMY-VL2-NT
(SEQ ID NO: 209)
GAAATAGTGATGACGCAGTCTCCAGCCACCCTGTCTGTGTCTCCAGGGGA

AAGAGCCACCCTCTCCTGCAGGGCCAGTCAGACGGTTAAGAATAATTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAACAACTGGTTGCCCATCAACCCCTAT

ACCTTCGGCCAAGGGACCAAGGTGGAAATCAAA

>DUMMY-VL2-AA
(SEQ ID NO: 210)
EIVMTQSPATLSVSPGERATLSCRASQTVKNNLAWYQQKPGQAPRLLIYG

ASTRATGIPARFSGSGSGTEFTLTISSLQSEDFAVYYCQQYNNWLPINPY

TFGQGTKVEIK

Bispecific Antibodies

In some embodiments, the bispecific antibody Ka3×O25 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 283, a CDRL2 comprising the amino acid sequence of SEQ ID NO: 289, and a CDRL3 comprising the amino acid sequence of SEQ ID NO: 295.

In some embodiments, the bispecific antibody Ka3×O25 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 212) encoded by the nucleic acid sequence shown in SEQ ID NO: 211.

In some embodiments, the bispecific antibody Ka3×O25 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 98) encoded by the nucleic acid sequence shown in SEQ ID NO: 97.

In some embodiments, the bispecific antibody Ka3×O30 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 284, a CDRL2 comprising the amino acid sequence of SEQ ID NO: 290, and a CDRL3 comprising the amino acid sequence of SEQ ID NO: 296.

In some embodiments, the bispecific antibody Ka3×O30 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 214) encoded by the nucleic acid sequence shown in SEQ ID NO: 213.

In some embodiments, the bispecific antibody Ka3×O30 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 100) encoded by the nucleic acid sequence shown in SEQ ID NO: 99.

In some embodiments, the bispecific antibody Ka3×O32 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 282, a CDRL2 comprising the amino acid sequence of SEQ ID NO: 288, and a CDRL3 comprising the amino acid sequence of SEQ ID NO: 294.

In some embodiments, the bispecific antibody Ka3×O32 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 216) encoded by the nucleic acid sequence shown in SEQ ID NO: 215.

In some embodiments, the bispecific antibody Ka3×O32 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 102) encoded by the nucleic acid sequence shown in SEQ ID NO: 101.

In some embodiments, the bispecific antibody Ka3×O35 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 287, a CDRL2 comprising the amino acid sequence of SEQ ID NO: 293, and a CDRL3 comprising the amino acid sequence of SEQ ID NO: 299.

In some embodiments, the bispecific antibody Ka3×O35 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 218) encoded by the nucleic acid sequence shown in SEQ ID NO: 217.

In some embodiments, the bispecific antibody Ka3×O35 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 104) encoded by the nucleic acid sequence shown in SEQ ID NO: 103.

In some embodiments, the bispecific antibody Ka3×O37 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 285, a CDRL2 comprising the amino acid sequence of SEQ ID NO: 291, and a CDRL3 comprising the amino acid sequence of SEQ ID NO: 297.

In some embodiments, the bispecific antibody Ka3×O37 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 220) encoded by the nucleic acid sequence shown in SEQ ID NO: 219.

In some embodiments, the bispecific antibody Ka3×O37 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 106) encoded by the nucleic acid sequence shown in SEQ ID NO: 105.

In some embodiments, the bispecific antibody Ka3×O38 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 286, a CDRL2 comprising the amino acid sequence of SEQ ID NO: 292, and a CDRL3 comprising the amino acid sequence of SEQ ID NO: 298.

In some embodiments, the bispecific antibody Ka3×O38 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 222) encoded by the nucleic acid sequence shown in SEQ ID NO: 221.

In some embodiments, the bispecific antibody Ka3×O38 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 108) encoded by the nucleic acid sequence shown in SEQ ID NO: 109.

In some embodiments, the bispecific antibody Ka3×O41 includes a common heavy chain comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227, a kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and a lambda light chain comprising a CDRL1 comprising the amino acid sequence of SEQ ID NO: 282, a CDRL2 comprising the amino acid sequence of SEQ ID NO: 288, and a CDRL3 comprising the amino acid sequence of SEQ ID NO: 300.

In some embodiments, the bispecific antibody Ka3×O41 includes a common heavy chain variable region (SEQ ID NO: 114) encoded by the nucleic acid sequence shown in SEQ ID NO: 113, a kappa light chain variable region (SEQ ID NO: 168) encoded by the nucleic acid sequence shown in SEQ ID NO: 167, and a lambda light chain variable region (SEQ ID NO: 224) encoded by the nucleic acid sequence shown in SEQ ID NO: 223.

In some embodiments, the bispecific antibody Ka3×O41 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55, and a lambda light chain (SEQ ID NO: 112) encoded by the nucleic acid sequence shown in SEQ ID NO: 111.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is the to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is the to specifically bind to its target, when the equilibrium binding constant ($K_d$) is 1 µM, e.g., ≤100 nM, preferably ≤10 nM, and more preferably ≤1 nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Various procedures known within the art may be used for the production of polyclonal or monoclonal antibodies directed against a given target, such as, for example, CD47, a tumor associated antigen or other target, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

In some embodiments, the antibodies of the invention are monoclonal antibodies. Monoclonal antibodies are generated, for example, by using the procedures set forth in the Examples provided herein. Antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')2 or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Bispecific antibodies are antibodies that have binding specificities for at least two different antigens. In the present case, one of the binding specificities is for a target such as CD47 or any fragment thereof. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Bispecific and/or monovalent antibodies of the invention can be made using any of a variety of art-recognized techniques, including those disclosed in co-pending application WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the invention by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of techniques are well-known in the art for producing xenogenic non-human animals. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The methods disclosed in co-pending application WO 2012/023053 overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in co-pending applications WO 2010/135558 and WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the invention. The bispecific antibodies of the invention can be of different Isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the invention. (see for example Strohl, W R Curr Opin Biotechnol 2009 (6):685-91; U.S. Pat. No. 6,528,624; PCT/US2009/0191199 filed Jan. 9, 2009). The methods of the invention can also be used to generate bispecific antibodies and antibody mixtures in a F(ab')2 format that lacks the Fc portion.

The common heavy chain and two different light chains are co-expressed into a single cell to allow for the assembly of a bispecific antibody of the invention. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore, a means to modulate the relative expression of the different polypeptides is used to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Sarnow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CaptureSelect Fab Kappa and CaptureSelect Fab Lambda affinity matrices (BAC BV, Holland). This multi-step affinity chromatography purification approach is efficient and generally applicable to antibodies of the invention. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

Other suitable purification methods include those disclosed in co-pending application PCT/IB2012/003028, filed on Oct. 19, 2012, published as WO2013/088259, the contents of which are hereby incorporated by reference in their entirety.

In other embodiments of producing bispecific antibodies, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer and/or other diseases and disorders associated with aberrant CD47 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{122}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030, 719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Anti-CD47×Anti-MSLN Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an antibody of the invention, are used to treat or alleviate a symptom associated with a cancer, such as, by way of non-limiting example, leukemias, lymphomas, breast cancer, colon cancer, ovarian cancer, bladder cancer, prostate cancer, glioma, lung & bronchial cancer, colorectal cancer, pancreatic cancer, esophageal cancer, liver cancer, urinary bladder cancer, kidney and renal pelvis cancer, oral cavity & pharynx cancer, uterine corpus cancer, and/or melanoma The present invention also provides methods of treating or alleviating a symptom associated with a cancer. A therapeutic regimen is carried out by identifying a subject, e.g., a human patient suffering from (or at risk of developing) a cancer, using standard methods.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against a target such as CD47, mesothelin, or a combination thereof (or a fragment thereof), may be used in methods known within the art relating to the localization and/or quantitation of these targets, e.g., for use in measuring levels of these targets within appropriate physiological samples, for use in diagnostic methods, for use in imaging the protein, and the like). In a given embodiment, antibodies specific any of these targets, or derivative, fragment, analog or homolog thereof, that contain the antibody derived antigen binding domain, are utilized as pharmacologically active compounds (referred to hereinafter as "Therapeutics").

An antibody of the invention can be used to isolate a particular target using standard techniques, such as immunoaffinity, chromatography or immunoprecipitation. Antibodies of the invention (or a fragment thereof) can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $_{125}I$, $^{131}I$, $^{35}S$ or $^{3}H$.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and neutralizes or otherwise inhibits the interaction between CD47 and SIRPα.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a given target (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies of the invention (also referred to herein as "active compounds"), and derivatives, fragments, analogs and homologs thereof, can be incorporated into pharmaceutical compositions suitable for administration. Such compositions typically comprise the antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: Affinity Measurements

MSLN arm. The affinity of various anti-MSLN sequences, referred to herein as MSLN arms, was determined using the Bio-Layer Interferometry (BLI) technology. An OctetRED96 instrument and Protein A biosensors were used (Pall, Basel, Switzerland). After hydration and a baseline step, biosensors were loaded for 2 min with the IgG at 1 µg/mL in running buffer (PBS, NaCl, Tween 20, BSA, ProClin00). A control IgG was loaded on additional biosensors for referencing. Then, biosensors were dipped into a serial dilution of human MSLN. MSLN concentrations were adapted according to the expected $K_D$ of each candidate. Biosensors were regenerated using 10 mM glycine pH 1.7. The affinity was measured applying a 1:1 global fitting model on double referenced curves. The results are shown below in Table 5.

TABLE 5

Affinity value of MSLN arms (n = 2)

| MSLN Arm | $K_D$ [nM] |
|---|---|
| O25 | 106 ± 9 |
| O30 | 0.48 ± 0.03 |
| O32 | 529 ± 49 |
| O35 | 22.7 ± 0.5 |
| O37 | 313 ± 74 |
| O38 | 168 ± 23 |
| O41 | 19 ± 2 |

Example 2: Cloning and Expression of Cynomolgus Mesothelin Full Length at the Cell Surface Cloning.

The sequence corresponding to the full-length protein Cynomolgus mesothelin (cMSLN) was synthesized and provided by Eurofins in the pEX-K4 vector. DNA was prepared and digested using HindIII and EcoRI restriction enzymes. The insert was gel-purified twice and cloned into the pEAK8 EF1 mammalian expression vector (Edge Biosystems, Gaithersburg, Md.). The construct was verified by DNA sequencing.

Expression.

The plasmid was then transfected into mammalian cells using a liposome based transfection reagent such as Lipofectamine 2000 (Thermo Fisher Scientific, Waltham, Mass.). The transfection step requires only small quantities of DNA and cells, typically 2 µg of plasmid DNA and 2×10⁵ cells per well and the transfection carried out in a 6-well plate. Although different mammalian cell lines can be used, in the examples given below, transformed human embryo kidney monolayer epithelial cells (PEAK cells) were transfected. These cells stably express the EBNA-1 gene, further supporting the episomal replication process, are semi-adherent and can be grown under standard conditions cell culture incubator (5% $CO_2$; 37° C. in DMEM medium supplemented with 10% fetal calf serum). After 24 h, cells were placed under selective conditions by adding medium containing 0.5-1 µg/mL puromycin, as cells harboring the episomal vector are resistant to this antibiotic.

Cells were split in complete medium containing puromycin for the generation of semi-stable cell lines expressing cMSLN. Cell lines were used for phage display selection and cell-based assay such as Fluorescence Associated Cell Sorting (FACS).

Example 3: Expression and Purification of Bispecific Antibodies Carrying a Lambda and a Kappa Light Chain The simultaneous expression of one heavy chain and two light chains in the same cell can lead to the assembly of three different antibodies. Simultaneous expression can be achieved in different ways such as the transfection of multiple vectors expressing one of the chains to be co-expressed or by using vectors that drive multiple gene expression. A vector pNovi κHλ was previously generated to allow for the co-expression of one heavy chain, one Kappa light chain and one Lambda light chain as described in US 2012/0184716 and WO 2012/023053, each of which is hereby incorporated by reference in its entirety. The expression of the three genes is driven by human cytomegalovirus promoters (hCMV), and the vector also contains a glutamine synthetase gene (GS) that enables the selection and establishment of stable cell lines. The VL genes of the anti-hMSLN IgGλ or the anti-hCD47 IgGκ were cloned in the vector pNovi κHλ, for transient expression in mammalian cells. Peak cells were amplified and split in T175 flasks at a concentration of 8×10⁶ cells per flask in 45 mL culture media containing fetal bovine serum. 30 µg of plasmid DNA were transfected into the cells using Lipofectamine 2000 transfection reagent according to manufacturer's instructions. Antibody concentration in the serum-containing supernatant of transfected cells was measured at several time points during the production using the Bio-Layer Interferometry (BLI) technology. An OctetRED96 instrument and Protein A biosensors were used for quantitation (Pall, Basel, Switzerland). 200 µL of supernatant were used to determine IgG concentration; biosensors were pre-conditioned and regenerated using 10 mM glycine pH 1.7 and IgG calibrators diluted in conditioned PEAK cell medium were prepared for standard curve generation. Concentrations were determined using the dose response 5PL weighted Y standard curve equation and an initial slope binding rate equation. According to antibody concentration, supernatants were harvested 7 to 10 days after transfection and clarified by centrifugation at 1300 g for 10 min. The purification process was composed of three affinity steps. First, the CaptureSelect™ IgG-CH1 affinity matrix (Thermo Fisher Scientific, Waltham, Mass.) was washed with PBS and then added in the clarified supernatant. After incubation overnight at +4° C., supernatants were centrifuged at 1000 g for 10 min, flow through was stored and resin washed twice with PBS. Then, the resin was transferred on spin columns and a solution containing 50 mM glycine at pH 2.7 was used for elution. Several elution fractions were generated, pooled and desalted against 25 mM Histidine/125 mM NaCl pH6.0 buffer using 50 kDa Amicon® Ultra Centrifugal filter units (Merck KGaA, Darmstadt, Germany). The final product, containing total human IgGs from the supernatant, was quantified using a Nanodrop spectrophotometer (NanoDrop Technologies, Wilmington, Del.) and incubated for 30 min at RT and 20 rpm with the appropriate volume of CaptureSelect™ LC-kappa (Hu) affinity matrix (Thermo Fisher Scientific, Waltham, Mass.). Incubation, resin recovery, elution and desalting steps were performed as described previously. The last affinity purification step was performed using the CaptureSelect™ LC-lambda (Hu) affinity matrix (Thermo Fisher Scientific, Waltham, Mass.) applying the same process as for the two previous purifications. The final product was quantified using the Nanodrop. Purified bispecific antibodies were analyzed by electrophoresis in denaturing and reducing conditions. The Agilent 2100 Bioanalyzer was used with the Protein 80 kit as described by the manufacturer (Agilent Technologies, Santa Clara, Calif., USA). 4 µL of purified samples were mixed with sample buffer supplemented with dithiothreitol (DTT; Sigma Aldrich, St. Louis, Mo.). Samples were heated at 95° C. for 5 min and then loaded on the chip. An aliquot from the first purification step (containing the bispecific antibody and both monospecific mAbs) and an aliquot of the final product were loaded on an IsoElectric Focusing (IEF) gel to evaluate the purity of the final purified bispecific antibody (absence of mAb contamination). The aggregate level was determined by SEC-HPLC. Finally, binding of the bispecific antibodies on both targets was assessed using the OctetRED96. Briefly, biotinylated targets (hMSLN, hCD47 and an irrelevant target) were loaded on a streptavidin biosensor. Then this biosensor was dipped into a solution containing the bispecific antibody and binding was monitored in real time. All samples were tested for endotoxin contamination using the Limulus Amebocyte Lysate test (LAL; Charles River Laboratories, Wilmington, Mass.).

Example 4: Cloning, Expression and Purification of Human Mesothelin Cloning

The sequence corresponding to the extracellular domain of human mesothelin (hMSLN), amino acids 296 to 580, followed by an Avitag™ (Avidity, Denver Colo.) and an hexa-histidine tag at the C-terminus, was synthesized and provided by Eurofins in the pEX-K vector. Tags allow for single site biotinylation of the protein and purification by IMAC (Immobilized Metal Ion Affinity Chromatography), respectively. DNA was prepared and digested using HindIII and EcoRI restriction enzymes. The insert was gel-purified twice and cloned into the pEAK8 EF1 mammalian expression vector (Edge Biosystems, Gaithersburg, Md.). The construct was verified by DNA sequencing.

Expression.

The plasmid was then transfected into mammalian cells using a liposome based transfection reagent such as Lipofectamine 2000 (Thermo Fisher Scientific, Waltham, Mass.). The transfection step requires only small quantities of DNA and cells, typically $2\times10^5$ cells and 2 µg of plasmid DNA per well and the transfection carried out in a 6-well plate. Although different mammalian cell lines can be used, in the examples given below, transformed human embryo kidney monolayer epithelial cells (PEAK cells) were transfected. These cells stably express the EBNA-1 gene, further supporting the episomal replication process, are semi-adherent and can be grown under standard conditions cell culture incubator (5% $CO_2$; 37° C. in DMEM medium supplemented with 10% fetal calf serum). After 24 h, cells were placed under selective conditions by adding medium containing 0.5-1 µg/mL puromycin, as cells harboring the episomal vector are resistant to this antibiotic.

Two to three weeks after transfection, cells were used to seed disposable CELLine bioreactors for the production step. To produce in vivo biotinylated proteins, 50 µM of biotin were added into the culture medium. The CELLine is a two-compartment bioreactor that can be used in a standard cell culture incubator. The smaller compartment (15 mL) contains the cells in serum-free medium and is separated from a larger (one liter) complete medium containing compartment by a semi-permeable membrane with a cut-off size of 10 kDa (Bruce et al. 2002, McDonald et al. 2005). This system allows for the diffusion of nutrients, gazes and metabolic waste products, while retaining cells and secreted proteins in the smaller compartment. The culture was maintained for 7-10 days before harvest of the supernatant. As the medium contains serum, the cells maintain good viability and several production runs can be generated using the same cells and containers.

Purification.

After harvest, the supernatant retrieved from the cell compartment of the CELLine bioreactor contains concentrated recombinant protein and reduced levels of contaminants as they cannot cross the 10 kDa membrane separating the two chambers of the reactor. This increased recombinant protein to contaminant ratio greatly enhances the efficiency of purification using IMAC. This supernatant was clarified by centrifugation and filtered through a 0.22 µm membrane. The concentrated supernatant was then supplemented with 100 mM imidazole and loaded on Ni-NTA affinity chromatography resin (Qiagen). The relatively high concentration of imidazole minimizes binding of contaminants to the resin. After washing of the column, proteins are eluted at a flow rate of 2 mL/min using a 30 mL imidazole gradient (20-400 mM imidazole) on an AKTA Prime chromatography system (GE Healthcare, Little Chalfont, UK). The eluted fractions can be analyzed by SDS-PAGE or ELISA to determine their content in recombinant protein. The fractions of interest are pooled and desalted on PD-10 columns (GE Healthcare) equilibrated with phosphate buffered saline or another appropriate buffer. The desalted proteins can then be quantified using various techniques and their purity analyzed by SDS-PAGE. Recombinant hMSLN was biotinylated in vitro using biotin ligase (Avidity, Denver Colo.) according to manufacturer's instructions. After desalting the biotinylation level was evaluated by pull-down assays using streptavidin magnetic beads and SDS-PAGE analysis.

Example 5: Fixed VH Candidates Reformatting into IgG and Transient Expression in Mammalian Cells After screening, scFv candidates against hMSLN or hCD47 were reformatted into IgG and expressed by transient transfection into PEAK cells. The VL sequences of selected scFv were amplified with specific oligonucleotides and cloned into an expression vector containing the common heavy chain and the light chain constant region. The constructions were verified by sequencing. Mammalian Peak cells were grown in T75 flasks at a concentration of $3\times10^6$ cells per flask in 25 mL culture medium containing fetal bovine serum, at 37° C. and 5% $CO_2$ in a humidified incubator. One day following cell split, the expression vectors were transfected using Lipofectamine 2000 Transfection Reagent (Thermo Fisher Scientific, Waltham, Mass.), according to manufacturer's instructions. Antibody concentration in the serum-containing supernatant of transfected cells was measured at several time points during the production using the Bio-Layer Interferometry (BLI) technology. An OctetRED96 instrument and Protein A biosensors were used for quantitation (Pall, Basel, Switzerland). 200 µL of supernatant were used to determine IgG concentration; biosensors were pre-conditioned and regenerated using 10 mM glycine pH 1.7 and IgG calibrators diluted in conditioned Peak cell medium were prepared for standard curve generation. Concentrations were determined using the dose response 5PL unweighted standard curve equation and an initial slope binding rate equation. Following 6-7 days culture period, the supernatant was harvested for IgG purification on FcXL affinity chromatography resin (Thermo Fisher Scientific, Waltham, Mass.) according to manufacturer's instructions. Briefly, supernatants from transfected cells were incubated overnight at +4° C. with the resin. Samples were then centrifuged and the resin was transferred on a column filter for elution. The eluted IgG fraction was then desalted against PBS and the IgG content quantified by absorption at 280 nm. Purity and IgG integrity were verified by electrophoresis.

Example 6: Binding of MSLN Monoclonal Antibodies and MSLN/CD47 Bispecific Antibodies to Human and Cynomolgus Mesothelin The ability of MSLN monoclonal antibodies and MSLN/CD47 bispecific antibodies to bind cell surface expressed human and cynomolgus monkey mesothelin was tested by flow cytometry. CHO cells stably expressing human MSLN (CHO-huMSLN cells) or cynomolgus monkey MSLN (CHO-huMSLN cells) were used for this purpose, since the anti-human CD47 antibody arm of the biAbs does not recognize the hamster mesothelin ortholog. In brief, increasing concentrations of MSLN Mabs and biAbs were incubated with CHO-huMSLN cells or CHO-cyMSLN cells for 30 minutes at 4° C. After two washes, bound antibody was detected using PE-conjugated anti-human Fc secondary antibody (Southern Biotech #9042-09). Non-transfected CHO cells were used as control. FIG. 1 shows strong binding of the MSLN monoclonal and bispecific antibodies to mesothelin expressed at the surface of mesothelin-transfected CHO cells. All MSLN antibodies show a high level of species cross-reactivity, as the MFI/antibody concentration curves obtained with human and cynomolgus MSLN-expressing CHO cells look very similar.

Example 7: ADCP Induced by Bispecific Antibodies Targeting MSLN and CD47

The ability of dual targeting CD47/MSLN κλ bodies to co-engage CD47 and MSLN on the cell surface allows MSLN-dependent neutralization of the CD47-SIRPα interaction. This, in turn, translates into efficient and selective cancer cell killing mediated by CD47/MSLN κλ bodies, as demonstrated in ADCP experiments described in this example. ADCP of three tumor cell lines expressing different levels of CD47 and MSLN was tested: NCI-N87, HPAC and Caov-3. The levels of cell surface expression of CD47 and Mesothelin for NCI-N87 cells were 43,000 and 27,000, respectively. The levels of cell surface expression of CD47 and Mesothelin for HPAC cells were 105,000 and 13,000, respectively. The levels of cell surface expression of CD47 and Mesothelin for Caov-3 cells were 220,000 and 38,000, respectively. ADCP experiments were performed with human macrophages differentiated from peripheral blood monocytes. Two different assay formats were used to assess phagocytosis. In the experiments shown in FIG. 2 macrophages were co-incubated with CFSE-labeled target cells (effector: target ratio 3:1) for 2.5 hours at 37° C. in the presence of increasing concentrations of antibody. At the end of the incubation period, biotinylated anti-human CD14 antibody and Strep-Cy5 were added to label the macrophages. The cells were then washed and subjected to FACS analysis. Phagocytosis was evidenced by double-positive events. In the experiments shown in FIG. 3, macrophages adhering to microplate wells were co-incubated with Calcein AM-labeled target cells (effector: target ratio 1:1) for 2.5 hours at 37° C. in the presence of increasing concentrations of antibody. At the end of the incubation period, supernatants were replaced by complete culture medium and the microplates were imaged with the CellInsight CX5 High Content Screening Platform. 1500 macrophages were acquired and analyzed per well. Phagocytosis was evidenced as double-positive events and the phagocytosis indexes were calculated by the software.

Dose-response experiments in FIG. 2 demonstrate that the CD47/MSLN BsAbs phagocytose NCI-N87 and HPAC cells in a MSLN-dependent manner, given that the CD47 monovalent antibody (i.e., a la body lacking the anti-MSLN arm) was much less efficient. FIG. 2 also shows that the CD47/MSLN BsAbs induce more potent ADCP than the benchmark antibodies, the high-affinity anti-human CD47 monoclonal antibody B6H12-huIgG1 or the monoclonal anti-MSLN antibody amatuximab (KEGG ID: D09767, PubChem SID: 124490507). FIG. 3 shows ADCP with CD47/MSLN κλ bodies compared to the corresponding anti-CD47 and anti MSLN monovalent antibodies and the anti MSLN mAb. CD47/MSLN κλ bodies induce significantly higher levels of NCI-N87 and Caov-3 target cell phagocytosis, confirming that dual-target engagement and MSLN-mediated CD47 blockade are key for in vitro efficacy.

Example 8: ADCC Induced by Bispecific Antibodies Targeting MSLN and CD47

Figure 5A:
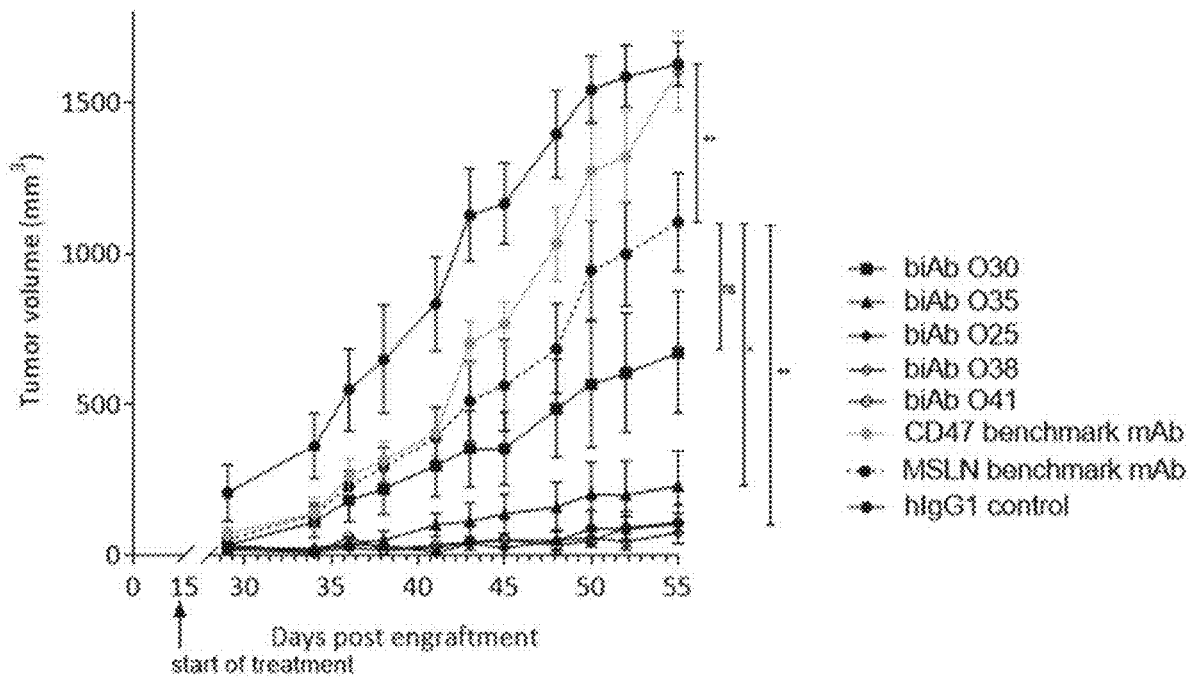
FIGS. 5A and 5B show the anti-tumor activity of 5 of the CD47/MSLN κλ bodies to the corresponding CD47 monovalent antibody and benchmark monoclonal antibodies, the CD47 Mab B6H12 (on human IgG1 background) and the MSLN mAb amatuximab.
Figure 5B:
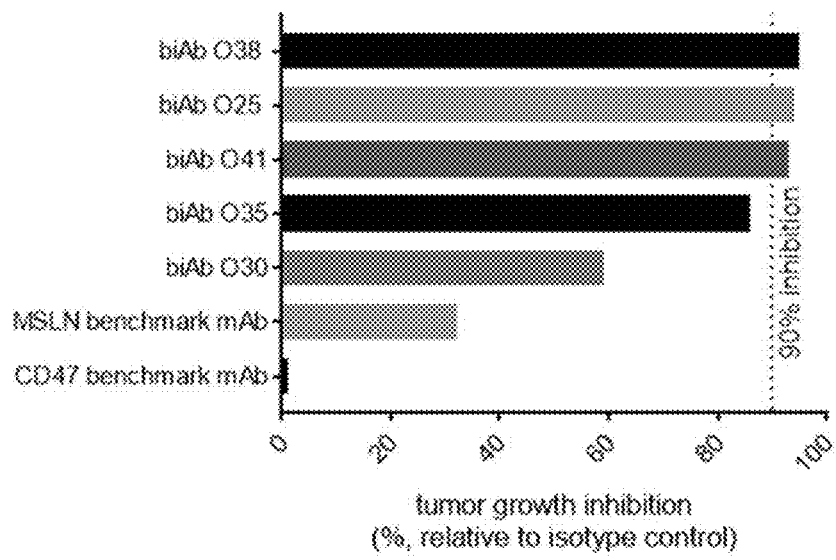
Figure 6A:
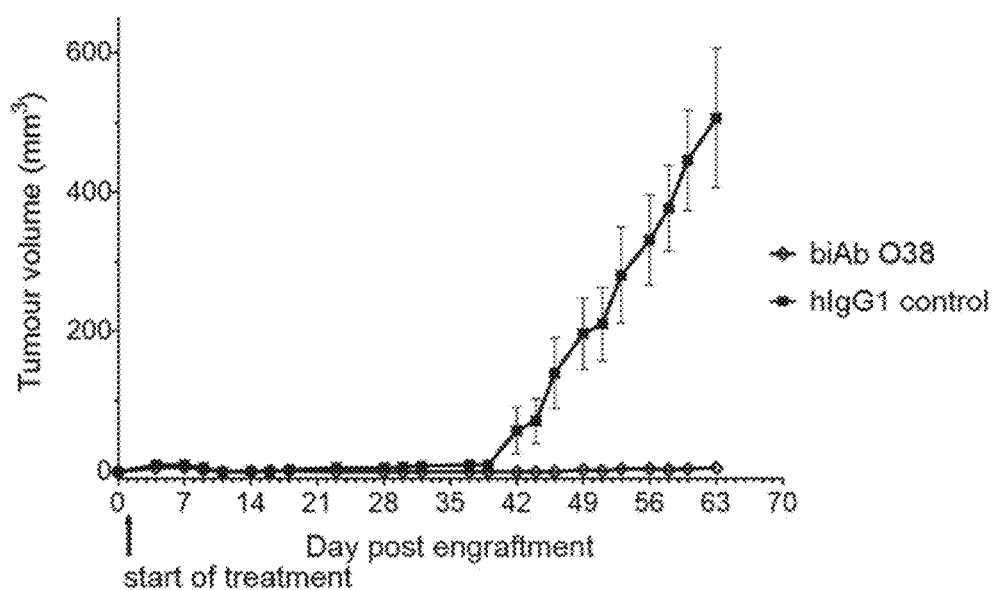
FIGS. 6A and 6B show the anti-tumor activity of biAbO38 with two MSLN-expressing ovarian cancer cell lines.
Figure 6B:
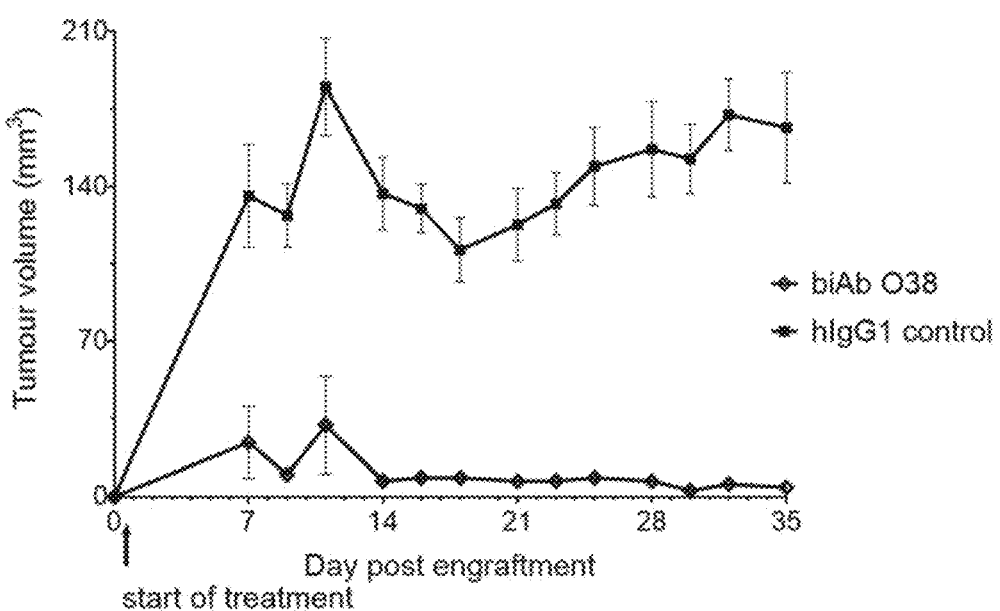

Antibody-dependent cell-mediated cytotoxicity (ADCC) of four CD47/MSLN κλ bodies (K2O25, K2O35, K2O38 and K2O41) was evaluated using a Cr51-release cell based assay. ADCC of three tumor cell lines expressing different levels of CD47 and MSLN was tested: NCI-N87, NCI-H226 and HepG2-MSLN. The levels of cell surface expression of CD47 and Mesothelin for NCI-N87 cells were 43,000 and 27,000, respectively. The levels of cell surface expression of CD47 and Mesothelin for NCI-H226 cells were 200,000 and 250,000, respectively. The levels of cell surface expression of CD47 and Mesothelin for HepG2-MSLN cells (obtained by stable transfection of human mesothelin in the human liver hepatocarcinoma cell line HepG2) were 22,000 and 120,000, respectively. The ADCC experiments were performed with whole human PBMCs as effector cells and Cr51-loaded MSLN-positive target cell lines. In brief, target cells were loaded with Cr51 for 1 h at 37° C. After washing, cells were opsonized with CD47/MSLN κλ bodies or the MSLN benchmark mAb amatuximab for 30 min at 37° C. 5,000 Cr51-loaded target cells were then mixed with 250,000 IL-2 activated PBMC effector cells to obtain the final 50:1 ratio between effector and target cells (E:T ratio=50) and incubated for 4 h at 37° C. After a brief centrifugation (10 min at 1500 rpm) the cell-free supernatant was counted in a γ-counter. Negative control (spontaneous Cr51 release) consisted of Cr51-loaded target cells incubated with medium in the absence of effector cells. Total lysis control consisted of Cr51-loaded target cells incubated with cell lysis solution (Triton X-100). Nonspecific lysis control (baseline) consisted of Cr51-loaded target cells incubated with effector cells, without any antibody addition. ADCC reaction was done in triplicates. The Ab specific ADCC percentage was calculated using the following formula: % ADCC=((sample cpm−nonspecific lysis control cpm)/(total lysis control cpm−negative control cpm))×100%. The experiment shown in FIG. 4 compared the effect of four CD47/MSLN κλ bodies and the MSLN benchmark mAb amatuximab. All the CD47/MSLN κλ bodies tested exhibited a approximately similar ADCC efficacy with the three cell lines. In all cases, ADCC induced by the CD47/MSLN κλ bodies was significantly higher than with amatuximab Example 9: In Vivo Antitumor Activity of Bispecific Antibodies The anti-tumor activity of five CD47/MSLN κλ bodies (biAb025, biAb030, biAb035, biAb038 and biAb041) was evaluated in xenograft models. In the experiment shown in FIG. 5, $3 \times 10^6$ HepG2-MSLN cells were implanted subcutaneously in NOD/SCID mice and let grow for 15 days. Subsequently, mice were randomized into 6 groups (7 mice per group) and the antibody treatment was initiated. Antibody was injected i.v. once a week until the end of the experiment (d55). In the experiment shown in FIG. 6A, $3 \times 10^6$ OVCAR3 cells were implanted subcutaneously in NOD/SCID mice. The following day, mice were randomized into 2 groups (7 mice per group) and the antibody treatment was initiated. Antibody was injected i.v. once a week until d56. In the experiment shown in FIG. 6B, $3 \times 10^6$ CAOV3 cells were implanted subcutaneously in NOD/SCID mice. The following day, mice were randomized into 2 groups (6 or 7 mice per group) and the antibody treatment was initiated. Antibody was injected i.v. once a week until d18. All the antibodies were administered at 60 mg/kg per injection. Tumor volumes were measured 2 to 3 times per week and calculated using the following formula: ((length× width2)/2). The experiment shown in FIG. 5 compared the effect of CD47/MSLN κλ bodies to the benchmark monoclonal antibodies, the CD47 mAb B6H12-hIgG1 and the MSLN mAb amatuximab. For statistical analyses at endpoint (FIG. 5A), one-way ANOVA was performed followed by multiple comparison test (Tukey's multiple comparison) using GraphPad Prism. p-value: *p<0.05, **p<0.01; ns, not significant. Percentage of tumor growth inhibition (TGI) in comparison with the isotype control group was also determined (FIG. 5B), using the formula: % TGI={1−[(Tt−T0)/(Vt−V0)]}×100; with Tt=median tumor volume of treated at time t; T0=median tumor volume of treated at time 0; Vt=median tumor volume of control at time t and V0=median tumor volume of control at time=O. As shown in FIG. 5, treatment with the five CD47/MSLN κλ-bodies and amatuximab, but not with the CD47 mAb B6H12-hIgG1, significantly reduced tumor growth as compared to hIgG1 control. Moreover, the anti-tumor efficacy of four of the five CD47/MSLN κλ-bodies tested (all but biAb030) was superior to amatuximab, with three biAbs displaying a TGI>90% (biAb025, biAb038 and biAb041). The experiments shown in FIG. 6 shows that the biAbO38 CD47/MSLN κλ body prevented tumor growth.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated bispecific antibody comprising a first arm that specifically binds CD47 and a second arm that binds mesothelin (MSLN), wherein the bispecific antibody comprises two heavy chains each comprising a CDRH1 comprising the amino acid sequence of SEQ ID NO: 225, a CDRH2 comprising the amino acid sequence of SEQ ID NO: 226, a CDRH3 comprising the amino acid sequence of SEQ ID NO: 227,
one kappa light chain comprising a CDRL1 comprising the amino acid sequence of SEQ ID NO: 240, a CDRL2 comprising the amino acid sequence of SEQ ID NO: 242, and a CDRL3 comprising the amino acid sequence of SEQ ID NO: 254, and
one lambda light chain comprising a combination of a CDRL1 amino acid sequence, a CDRL2 amino acid sequence, and a CDRL3 amino acid sequence selected from the group consisting of:
(a) a CDRL1 comprising the amino acid sequence of SEQ ID NO: 286, a CDRL2 comprising the amino acid sequence of SEQ ID NO: 292, and a CDRL3 comprising the amino acid sequence of SEQ ID NO: 298;
(b) a CDRL1 comprising the amino acid sequence of SEQ ID NO: 282, a CDRL2 comprising the amino acid sequence of SEQ ID NO: 288, and a CDRL3 comprising the amino acid sequence of SEQ ID NO: 294;
(c) a CDRL1 comprising the amino acid sequence of SEQ ID NO: 283, a CDRL2 comprising the amino acid sequence of SEQ ID NO: 289, and a CDRL3 comprising the amino acid sequence of SEQ ID NO: 295;
(d) a CDRL1 comprising the amino acid sequence of SEQ ID NO: 284, a CDRL2 comprising the amino acid sequence of SEQ ID NO: 290, and a CDRL3 comprising the amino acid sequence of SEQ ID NO: 296;
(e) a CDRL1 comprising the amino acid sequence of SEQ ID NO: 285, a CDRL2 comprising the amino acid sequence of SEQ ID NO: 291, and a CDRL3 comprising the amino acid sequence of SEQ ID NO: 297;
(f) a CDRL1 comprising the amino acid sequence of SEQ ID NO: 287, a CDRL2 comprising the amino acid sequence of SEQ ID NO: 293, and a CDRL3 comprising the amino acid sequence of SEQ ID NO: 299; and
(g) a CDRL1 comprising the amino acid sequence of SEQ ID NO: 282, a CDRL2 comprising the amino acid sequence of SEQ ID NO: 288, and a CDRL3 comprising the amino acid sequence of SEQ ID NO: 300.

2. The isolated bispecific antibody of claim 1, wherein the bispecific antibody inhibits interaction between human CD47 and human signal-regulatory protein alpha (SIRPα).

3. The isolated bispecific antibody of claim 1, wherein the first arm comprises a variable heavy chain comprising the amino acid sequence of SEQ ID NO: 114 and a variable light chain comprising the amino acid sequence of SEQ ID NO: 168.

4. The isolated bispecific antibody of claim 1, wherein the first arm comprises a heavy chain comprising the amino acid sequence of SEQ ID NO: 2 and a light chain comprising the amino acid sequence of SEQ ID NO: 56.

5. The isolated bispecific antibody of claim 1, wherein isolated bispecific antibody comprises a variable heavy chain comprising the amino acid sequence of SEQ ID NO: 114, a kappa variable light chain comprising the amino acid sequence of SEQ ID NO: 168, and a lambda variable light chain comprising an amino acid sequence selected from the group consisting of SEQ ID NO: 212, 214, 216, 218, 220, 222, and 224.

6. The isolated bispecific antibody of claim 1, wherein isolated bispecific antibody comprises a variable heavy chain comprising the amino acid sequence of SEQ ID NO: 114, and a combination of a kappa variable light chain and a lambda light chain selected from the group consisting of
(a) a kappa variable light chain comprising the amino acid sequence of SEQ ID NO: 168, and a lambda variable light chain comprising the amino acid sequence of SEQ ID NO: 212;
(b) a kappa variable light chain comprising the amino acid sequence of SEQ ID NO: 168, and a lambda variable light chain comprising the amino acid sequence of SEQ ID NO: 214;
(c) a kappa variable light chain comprising the amino acid sequence of SEQ ID NO: 168, and a lambda variable light chain comprising the amino acid sequence of SEQ ID NO: 216;
(d) a kappa variable light chain comprising the amino acid sequence of SEQ ID NO: 168, and a lambda variable light chain comprising the amino acid sequence of SEQ ID NO: 218;
(e) a kappa variable light chain comprising the amino acid sequence of SEQ ID NO: 168, and a lambda variable light chain comprising the amino acid sequence of SEQ ID NO: 220;
(f) a kappa variable light chain comprising the amino acid sequence of SEQ ID NO: 168, and a lambda variable light chain comprising the amino acid sequence of SEQ ID NO: 222; and
(g) a kappa variable light chain comprising the amino acid sequence of SEQ ID NO: 168, and a lambda variable light chain comprising the amino acid sequence of SEQ ID NO: 224.

7. The isolated bispecific antibody of claim 1, wherein isolated bispecific antibody comprises a heavy chain comprising the amino acid sequence of SEQ ID NO: 2, a kappa light chain comprising the amino acid sequence of SEQ ID NO: 56, and a lambda light chain comprising an amino acid sequence selected from the group consisting of SEQ ID NO: 98, 100, 102, 104, 106, 108, and 110.

8. The isolated bispecific antibody of claim 1, wherein isolated bispecific antibody comprises a heavy chain comprising the amino acid sequence of SEQ ID NO: 2, and a combination of a kappa light chain and a lambda light chain selected from the group consisting of
- (a) a kappa light chain comprising the amino acid sequence of SEQ ID NO: 56, and a lambda light chain comprising the amino acid sequence of SEQ ID NO: 98;
- (b) a kappa light chain comprising the amino acid sequence of SEQ ID NO: 56, and a lambda light chain comprising the amino acid sequence of SEQ ID NO: 100;
- (c) a kappa light chain comprising the amino acid sequence of SEQ ID NO: 56, and a lambda light chain comprising the amino acid sequence of SEQ ID NO: 102;
- (d) a kappa light chain comprising the amino acid sequence of SEQ ID NO: 56, and a lambda light chain comprising the amino acid sequence of SEQ ID NO: 104;
- (e) a kappa light chain comprising the amino acid sequence of SEQ ID NO: 56, and a lambda light chain comprising the amino acid sequence of SEQ ID NO: 106;
- (f) a kappa light chain comprising the amino acid sequence of SEQ ID NO: 56, and a lambda light chain comprising the amino acid sequence of SEQ ID NO: 108; and
- (g) a kappa light chain comprising the amino acid sequence of SEQ ID NO: 56, and a lambda light chain comprising the amino acid sequence of SEQ ID NO: 110.

9. The isolated bispecific antibody of claim 1, wherein the bispecific antibody comprises two copies of a single heavy chain polypeptide and a first light chain and a second light chain, wherein the first and second light chains are different.

10. The isolated bispecific antibody of claim 9, wherein at least a portion of the first light chain is of the Kappa type and at least a portion of the second light chain is of the Lambda type.

11. The isolated bispecific antibody of claim 10, wherein the first light chain comprises at least a Kappa constant region.

12. The isolated bispecific antibody of claim 11, wherein the first light chain further comprises a Kappa variable region.

13. The isolated bispecific antibody of claim 11, wherein the first light chain further comprises a Lambda variable region.

14. The isolated bispecific antibody of claim 10, wherein the second light chain comprises at least a Lambda constant region.

15. The isolated bispecific antibody of claim 14, wherein the second light chain further comprises a Lambda variable region.

16. The isolated bispecific antibody of claim 14, wherein the second light chain further comprises a Kappa variable region.

17. The isolated bispecific antibody of claim 10, wherein the first light chain comprises a Kappa constant region and a Kappa variable region, and wherein the second light chain comprises a Lambda constant region and a Lambda variable region.

18. The isolated bispecific antibody of claim 1, wherein the constant and variable framework region sequences are human.

* * * * *